US009107884B2

(12) United States Patent
Chedotal et al.

(10) Patent No.: US 9,107,884 B2
(45) Date of Patent: Aug. 18, 2015

(54) USE OF SEMAPHORIN 6A FOR PROMOTING MYELINATION AND OLIGODENDROCYTE DIFFERENTIATION

(75) Inventors: Alain Chedotal, La Reine (FR); Sha Mi, Belmont, MA (US); Frederic Bernard, Colmar (FR)

(73) Assignees: BIOGEN MA INC., Cambridge, MA (US); CENTRE NATIONAL DE RECHERCHE SCIENTIFIQUE, Paris (FR)

( * ) Notice: Subject to any disclaimer, the term of this patent is extended or adjusted under 35 U.S.C. 154(b) by 1689 days.

(21) Appl. No.: 12/525,514

(22) PCT Filed: Feb. 4, 2008

(86) PCT No.: PCT/US2008/001444
§ 371 (c)(1),
(2), (4) Date: Mar. 29, 2010

(87) PCT Pub. No.: WO2008/097503
PCT Pub. Date: Aug. 14, 2008

(65) Prior Publication Data
US 2010/0189713 A1    Jul. 29, 2010

Related U.S. Application Data

(60) Provisional application No. 60/898,992, filed on Feb. 2, 2007.

(51) Int. Cl.
| | |
|---|---|
| A61K 38/16 | (2006.01) |
| A61K 38/17 | (2006.01) |
| A01K 67/027 | (2006.01) |
| C07K 14/705 | (2006.01) |
| C12N 5/0793 | (2010.01) |
| C12N 5/079 | (2010.01) |
| A61K 35/12 | (2015.01) |

(52) U.S. Cl.
CPC ......... *A61K 38/1709* (2013.01); *A01K 67/0276* (2013.01); *C07K 14/705* (2013.01); *C12N 5/0619* (2013.01); *C12N 5/0622* (2013.01); *A01K 2217/072* (2013.01); *A01K 2227/105* (2013.01); *A61K 35/12* (2013.01); *C12N 2501/998* (2013.01); *C12N 2502/08* (2013.01); *C12N 2510/00* (2013.01)

(58) Field of Classification Search
None
See application file for complete search history.

(56) References Cited

U.S. PATENT DOCUMENTS 5,574,009 A    11/1996    Cohen et al.

FOREIGN PATENT DOCUMENTS

WO    WO 03/100041 A1    12/2003
WO    WO 03/102584 A1    12/2003

OTHER PUBLICATIONS

Rudinger. In Peptide Hormones. J.A. PArsons, ed. University Park Press, Baltimore, 1976, pp. 1-7.*
NCBI Entrez, Swiss-Prot Report, Accession No. O35464, Entry Date May 30, 2000.
NCBI Entrez, GenBank Report, Accession No. EAW48934.1, Entry Date Feb. 4, 2010.
Baumann, N. and Pham-Dinh, D., "Biology of Oligodendrocyte and Myelin in the Mammalian Central Nervous System," *Physiological Reviews 81*:871-927, American Physiological Society (2001).
Behar, O., et al., "Semaphorin 3A Growth Cone Collapse Requires a Sequence Homologous to Tarantula Hanatoxin," *Proceedings of the National Academy of Sciences 96*:13501-13505, National Academy of Sciences (1999).
Bernard, F., et al., "Identification of Living Oligodendrocyte Developmental Stages by Fractal Analysis of Cell Morphology," *The Journal of Neuroscience Research 65*:439-445, Wiley-Liss, Inc. (2001).
Besnard, F., et al., "Effects of Acidic and Basic Fibroblast Growth Factors on Proliferation and Maturation of Cultured Rat Oligodendrocytes," *International Journal of Developmental Neuroscience 7*:401-409, Pergamon Press (1989).
Bogler, O., et al., "Cooperation between two Growth Factors Promotes Extended Selfrenewal and Inhibits Differentiation of Oligodendrocyte-type-2 Astrocyte (O-2A) Progenitor Cells," *Proceedings of the National Academy of Sciences 87*:6368-6372, National Academy of Sciences (1990).
Le Bras, B., et al., "Oligodendrocyte Development in the Embryonic Brain: the Contribution of the plp Lineage," *International Journal of Developmental Biology 49*:209-220, UBC Press (2005).
Brown, C., et al., "PlexinA2 and Semaphorin Signaling During Cardiac Neural Crest Development," *Development 128*:3071-3080, The Company of Biologists Limited (2001).
Castellani, V., et al., "*Cis* and *Trans* Interactions of L1 with Neuropilin-1 Control Axonal Responses to Semaphorin 3A," *The EMBO Journal 21*:6348-6357, Nature Publishing Group (2002).
Chang, A., et al., "Premyelinating Oligodendrocytes in Chronic Lesions of Multiple Sclerosis," *The New England Journal of Medicine 346*:165-173, Massachusetts Medical Society (2002).
Chedotal, A., "Multiple Functions for Slits and Semaphorins in the Nervous System," *Journal of Neurochemistry 98*:42, International Society for Neurochemistry (2006).

(Continued)

*Primary Examiner* — Jeffrey Stucker
*Assistant Examiner* — Stephen Gucker
(74) *Attorney, Agent, or Firm* — Sterne, Kessler, Goldstein & Fox P.L.L.C.

(57)    ABSTRACT

The invention provides methods of treating diseases, disorsers or injuries involving demyelination and dysmyelination, including multiple sclerosis, by the administration of a Sema6A polypeptide.

14 Claims, 9 Drawing Sheets

(56) References Cited

OTHER PUBLICATIONS

Chen, C. and Okayama, H., "High-Efficiency Transformation of Mammalian Cells by Plasmid DNA," *Molecular and Cellular Biology* 7:2745-2752, American Society for Microbiology (1987).

Culotti, J. and Kolodkin, A., "Functions of Netrins and Semaphorins in Axon Guidance," *Current Opinion in Neurobiology* 6:81-88, Elsevier Science (1996).

De Winter, F., et al., "Expression of Class-3 Semaphorins and Their Receptors in the Neonatal and Adult Rat Retina," *Investigative Ophthalmology and Visual Science* 45:4554-4562, Association for Research in Vision and Ophthalmology (2004).

Durand, B., et al., "Accumulation of the Cyclin-Dependent Kinase Inhibitor p27/Kip1 and the Timing of Oligodendrocyte Differentiation," *The EMBO Journal* 16:306-317, Oxford University Press (1997).

Evan, G., et al., "Isolation of Monoclonal Antibodies Specific for Human *c-myc* Proto-Oncogene Product," *Molecular and Cellular Biology* 5:3610-3616, American Society for Microbiology (1985).

Fiore, R. and Püschel, A., "The Function of Semaphorins During Nervous System Development," *Frontiers in Bioscience* 8:s484-499, Frontiers in Bioscience (2003).

Flanagan, J. and Leder, P., "The *kit* Ligand: A Cell Surface Molecule Altered in Steel Mutant Fibroblasts," *Cell* 63:185-194, Cell Press (1990).

Flanagan, J., et al., "Alkaline Phosphatase Fusions of Ligands or Receptors as in Situ Probes for Staining of Cells, Tissues, and Embryos," in *Methods in Enzymology*, Thorner, J. et al. eds., 327, Academic Press, pp. 19-35 (2000).

Gautier, G., et al., "The Class 6 Semaphorin SEMA6A is Induced by Interferon-γ and Defines an Activation Status of Langerhans Cells Observed in Pathological Situations," *American Journal of Pathology* 168:453-465, American Society for Investigative Pathology (2006).

Hamblet, N., et al., "Dishevelled 2 is Essential for Cardiac Outflow Tract Development, Somite Segmentation and Neural Tube Closure," *Development* 129:5827-5838, The Company of Biologists Limited (2002).

Hu, R., et al., "Gene Expression Profiling in the Human Hypothalamus-pituitary-adrenal Axis and Full-length cDNA Cloning," *Proceedings of the National Academy of Sciences* 97:9543-9548, National Academy of Sciences (2000).

Kameyama, T., et al., "Identification of Plexin Family Molecules in Mice," *Biochemical and Biophysical Research Communications* 226:396-402, National Center for Biotechnology Information (1996).

Kameyama, T., et al., "Identification of a Neuronal Cell Surface Molecule, Plexin, in Mice," *Biochemical and Biophysical Research Communications* 226:524-529, Academic Press Inc. (1996).

Katoh, K., et al., "Improved Mammalian Vector for High Expression of G418 Resistance," *Cell Structure and Function* 12:575-580, Japan Society for Cell Biology (1987).

Kerjan, G., et al., "The Transmembrane Semaphorin Sema6A Controls Cerebellar Granule Cell Migration," *Nature Neuroscience* 8:1516-1524, Nature Publishing Group (2005).

Kikuchi, K., et al., "In Vitro and in Vivo Characterization of a Novel Semaphorin 3A Inhibitor, SM-216289 or Xanthofulvin," *The Journal of Biological Chemistry* 278:42985-42991, The American Society for Biochemistry and Molecular Biology, Inc. (2003).

Klostermann, A., et al., "The Orthologous Human and Murine Semaphorin 6A-1 Proteins (SEMA6A-1/Sema6A-1) Bind to the Enabled/Vasodilator-stimulated Phosphoprotein-like Protein (EVL) via a Novel Carboxyl-terminal Zyxin-like Domain," *The Journal of Biological Chemistry* 275:39647-39653, The American Society for Biochemistry and Molecular Biology, Inc. (2000).

Kreibich, T., et al., "The Neurotransmitter Glutamate Reduces Axonal Responsiveness to Multiple Repellents through the Activation of Metabotropic Glutamate Receptor 1," *The Journal of Neuroscience* 24:7085-7095, The Society for Neuroscience (2004).

Leighton, P., et al., "Defining Brain Wiring Patterns and Mechanisms Through Gene Trapping in Mice," *Nature* 410:174-179, Nature Publishing Group (2001).

Love, C., et al., "The Ligand-binding Face of the Semaphorins Revealed by the High-resolution Crystal Structure of SEMA4D," *Nature Structural Biology* 10:843-848, Nature Publishing Group (2003).

Maestrini, E., et al., "A Family of Transmembrane Proteins with Homology to the MET-hepatocyte Growth Factor Receptor," *Proceedings of the National Academy of Sciences* 93:674-678, National Academy of Sciences (1996).

Matsushima, G. and Morell, P., "The Neurotoxicant, Cuprizone, as a Model to Study Demyelination and Remyelination in the Central Nervous System," *Brain Pathology* 11: 107-116, Wiley InterScience (2001).

Molyneaux, B., et al., "*Fezl* Is Required for the Birth and Specification of Corticospinal Motor Neurons," *Neuron* 47:817-831, Elsevier Inc. (2005).

Morris, D., et al., "Animal Knockout and Human Studies Identify SEMA6A and PLXNA2 as Schizophrenia Candidate Genes," *XIV World Congress on Psychiatric Genetics* 141B:737, Wiley-Liss, Inc. (2006).

Murakami, Y., et al., "Differential Expression of Plexin-A Subfamily Members in the Mouse Nervous System," *Developmental Dynamics* 220:246-258, Wiley-Liss Inc. (2001).

Nagase, T., et al., "Prediction of the Coding Sequences of Unidentified Human Genes. XVI. The Complete Sequences of 150 New cDNA Clones from Brain Which Code for Large Proteins in vitro," *DNA Research* 7:65-73, Oxford University Press (2000).

Nakayama, M., et al., "Protein-Protein Interactions between Large Proteins: Two-Hybrid Screening Using a Functionally Classified Library Composed of Long cDNAs," *Genome Research* 12:1773-1784, Cold Spring Harbor Laboratory Press (2002).

Okada, A., et al., "Plexin-A4 is Expressed in Oligodendrocyte Precursor Cells and Acts as a Mediator of Semaphorin Signals," *Biochemical and Biophysical Research Communications* 352:158-163, Elsevier Inc. (2006).

Pashenkov, M., et al., "Two Subsets of Dendritic Cells are Present in Human Cerebrospinal Fluid," *Brain* 124:480-492, Oxford University Press (2001).

Prislei, S., et al., "From Plasma Membrane to Cytoskeleton: A Novel Function for Semaphorin 6A," *Molecular Cancer Therapeutics* 7:233-241, American Association for Cancer Research (2007).

Renaud, J., et al., "Plexin-A2 and its Ligand, Sema6A, Control Nucleus-centrosome Coupling in Migrating Granule Cells," *Nature Neuroscience* 11:440-449, Nature Publishing Group (2008).

Sasaki, Y., et al., "Fyn and Cdk5 Mediate Semaphorin-3A Signaling, Which is Involved in Regulation of Dendrite Orientation in Cerebral Cortex," *Neuron* 35:907920, Cell Press (2002).

Shi, M., et al., "The Crystal Structure of the Plexin-Semaphorin-Integrin Domain/Hybrid Domain/I-EGF1 Segment from the Human Integrin $\beta_2$ Subunit at 1.8-Å Resolution," *The Journal of Biological Chemistry* 34:30586-30593, The American Society for Biochemistry and Molecular Biology, Inc. (2005).

Siebold, C., et al., "High-resolution Structure of the Catalytic Region of MICAL (molecule interacting with CasL), a Multidomain Flavoenzyme-signaling Molecule," *Proceedings of the National Academy of Sciences* 102:16836-16841, National Academy of Sciences (2005).

Strausberg, R., et al., "Generation and Initial Analysis of More Than 15,000 Full-length Human and Mouse cDNA Sequences," *Proceedings of the National Academy of Sciences* 99:16899-16903, National Academy of Sciences (2002).

Suto, F., et al., "Identification and Characterization of a Novel Mouse Plexin, Plexin-A4,", *Mechanisms of Development* 120:385-396, Elsevier Science Ireland Ltd. (2003).

Suto, F., et al., "Plexin-A4 Mediates Axon-Repulsive Activities of Both Secreted and Transmembrane Semaphorins and Plays Roles in Nerve Fiber Guidance," *The Journal of Neuroscience* 25:3628-3637, Society of Neuroscience (2005).

Suto, F., et al., "Interactions Between Plexin-A2, Plexin-A4 and Semaphorin 6A Control Lamina-Restricted Projection of Hippocampal Mossy Fibers," *Neuron* 53:535-547, Cell Press (2007).

(56) References Cited

OTHER PUBLICATIONS

Takahashi, T. and Strittmatter, S., "PlexinA1 Autoinhibition by the Plexin Sema Domain," *Neuron* 29:429-439, Cell Press (2001).

Tamagnone, L., et al., "Plexins are a Large Family of Receptors for Transmembrane, Secreted, and GPI-anchored Semaphorins in Vertebrates" *Cell* 99: 71-80, Cell Press (1999).

Terman, J., et al., "MICALs, a Family of Conserved Flavoprotein Oxidoreductases, Function in Plexin-Mediated Axonal Repulsion," *Cell* 109:887-900 Cell Press (2002).

Theaudin, M., et al., "Oligodendrocyte Guidance Molecules in Multiple Sclerosis Lesions," *European Journal of Neurology* 11:121-122, Wiley-Blackwell (2004).

Toyofuku, T., et al., "Dual Roles of Sema6D in Cardiac Morphogenesis Through Region-specific Association of its Receptor Plexin-A1, with Off tack and Vascular Endothelial Growth Factor Receptor Type 2," *Genes and Development* 18:435-477, Cold Spring Harbor Laboratory Press (2004).

Usui, H., et al., "Plexin-A1 and Plexin-B1 Specifically Interact at their Cytoplasmic Domains," *Biochemical and Biophysical Research Communications* 300:927-931, Elsevier Science (2003).

Xu, X., et al., "The Transmembrane Protein Semaphorin 6A Repels Embryonic Sympathetic Axons," *The Journal of Neuroscience* 20:2638-2648, Society for Neuroscience (2000).

Yamamoto, M., et al., "Plexin-A4 Negatively Regulates T Lymphocyte Responses," *International Immunology* 20:1-8, Oxford University Press (2008).

Yamamura, T., et al., "Monoclonal Antibodies Against Myelin Proteolipid Protein: Identification and Characterization of Two Major Determinants," *Journal of Neurochemistry* 57:1671-1680, Raven Press Ltd. (1991).

Yokoo, H., et al., "Anti-Human Olig2 Antibody as a Useful Immunohistochemical Marker of Normal Oligodendrocytes and Gliomas," *The American Journal of Pathology* 164:1717-1725, American Society for Investigative Pathology (2004).

NCBI Entrez, GenBank Report, Accession No. AAH28744, Entry Date Oct. 1, 2007.

NCBI Entrez, GenBank Report, Accession No. AAH68155.1, Entry Date Jan. 30, 2008.

NCBI Entrez, GenBank Report, Accession No. BAC56599.1, Entry Date Feb. 25, 2003.

NCBI Entrez, GenBank Report, Accession No. EAL24077.1, Entry Date Aug. 10, 2004.

NCBI Entrez, GenBank Report, Accession No. EAW48935.1, Entry Date Dec. 18, 2006.

NCBI Entrez, GenBank Report, Accession No. EAW48937.1, Entry Date Dec. 18, 2006.

NCBI Entrez, GenBank Report, Accession No. EAW83795.1, Entry Date Dec. 18, 2006.

NCBI Entrez, GenBank Report, Accession No. EAW83796.1, Entry Date Dec. 18, 2006.

NCBI Entrez, GenBank Report, Accession No. EDL12937.1, Entry Date Jun. 7, 2007.

NCBI Entrez, GenBank Report, Accession No. EDL12938.1, Entry Date Jun. 7, 2007.

NCBI Entrez, GenBank Report, Accession No. EDL13704.1, Entry Date Jun. 7, 2007.

NCBI Entrez, GenBank Report, Accession No. EDL13705.1, Entry Date Jun. 7, 2007.

NCBI Entrez, GenBank Report, Accession No. NP_032908.2, Entry Date Oct. 18, 2009.

NCBI Entrez, GenBank Report, Accession No. NP_065847.1, Entry Date Dec. 7, 2009.

NCBI Entrez, GenBank Report, Accession No. NP_079455.3, Entry Date Oct. 18, 2009.

NCBI Entrez, GenBank Report, Accession No. NP_786926.2, Entry Date Oct. 18, 2009.

NCBI Entrez, GenBank Report, Accession No. NP_001099013.1, Entry Date Oct. 18, 2009.

NCBI Entrez, GenBank Report, Accession No. XP_001150634, Entry Date Sep. 15, 2006.

NCBI Entrez, GenBank Report, Accession No. XP_001150706, Entry Date Sep. 15, 2006.

NCBI Entrez, GenBank Report, Accession No. XP_001150901, Entry Date Sep. 15, 2006.

NCBI Entrez, GenBank Report, Accession No. XP_001150971, Entry Date Sep. 15, 2006.

NCBI Entrez, GenBank Report, Accession No. XP_001151041, Entry Date Sep. 15, 2006.

NCBI Entrez, GenBank Report, Accession No. XP_001151109, Entry Date Sep. 15, 2006.

NCBI Entrez, GenBank Report, Accession No. XP_001151177, Entry Date Sep. 15, 2006.

NCBI Entrez, GenBank Report, Accession No. XP_517889, Entry Date Sep. 15, 2006.

NCBI Entrez, GenBank Report, Accession No. XP_538552, Entry Date Aug. 30, 2005.

NCBI Entrez, GenBank Report, Accession No. XP_858843, Entry Date Aug. 30, 2005.

NCBI Entrez, GenBank Report, Accession No. XP_858886, Entry Date Aug. 30, 2005.

NCBI Entrez, GenBank Report, Accession No. XP_858921, Entry Date Aug. 30, 2005.

NCBI Entrez, GenBank Report, Accession No. XP_858964, Entry Date Aug. 30, 2005.

NCBI Entrez, GenBank Report, Accession No. XP_859002, Entry Date Aug. 30, 2005.

International Search Report for International Application No. PCT/US2008/001444, European Patent Office, Netherlands, mailed Nov. 13, 2008.

NCBI Entrez, GenBank Report, Accession No. AF288666, Entry Date Dec. 11, 2000.

* cited by examiner

Mouse Sema6A Isoforms

Sema6A expression

FIG. 5: Arrested differentiation of Sema6A−/− oligos in culture

Myelination in mixed DRG/Oligodendrocytecultures

Sema6A expression after cuprizone treatment

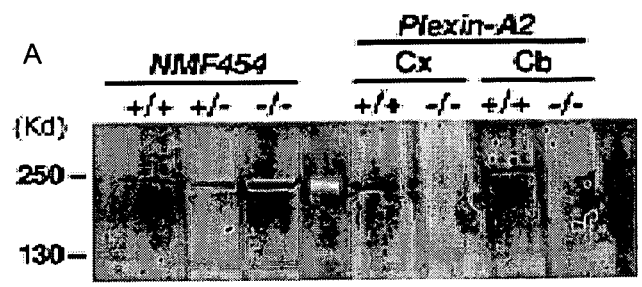
FIG. 9A
FIG. 9B
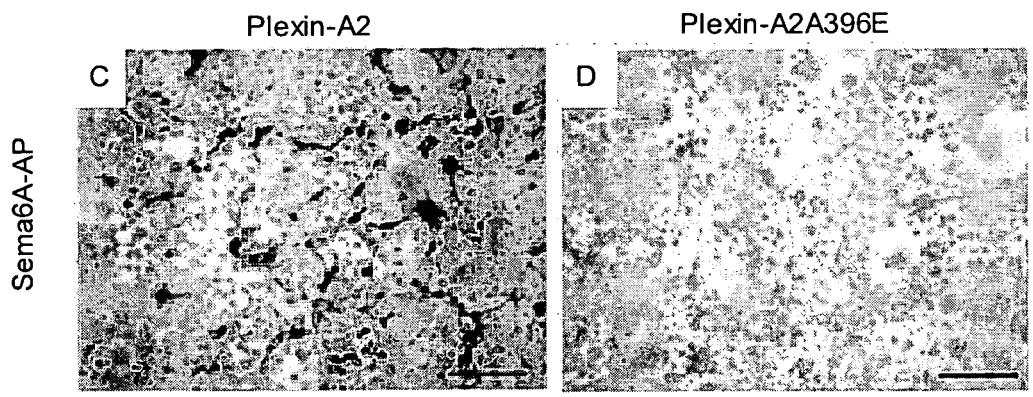
FIG. 9C          FIG. 9D

SEQUENCE LISTING

<160> NUMBER OF SEQ ID NOS: 19

<210> SEQ ID NO 1
<211> LENGTH: 3862
<212> TYPE: DNA

<213> ORGANISM: Homo sapiens

<400> SEQUENCE: 1

```
ggcacgaggc tgcagccaac tccgctcccc gcgcactcgg ctgcccaggc gctcggaacc      60
cagcagcggc gctcctccgc ggtgccggtc gcccgcgatg cccgcttagc agcgtgtagc     120
agcggccagc atcaccacac ccgcggcacc gcgctgccgg ccgcagagcc gggccagagc     180
cttgccccc tccccagcc cccaccccgc ccccgccct gaaatgactt gttaatcggc        240
gcagacacca ccaaggggac tcaccgaagt ggaatccaag tggaatttgg atttggagaa     300
gagtttcttg aacatttacc ctcttccttg ttggttttct ttttcttttt cttcttttttt    360
tttttggctt ctttttttcct ctccccttct ccgctcgtca ttggagatga acacatcgcg    420
tttgcatccc agaaagtagt cgccgcgact atttccccca agagacaag cacacatgta      480
ggaatgacaa aggcttgcga aggagagagc cgcagccgcg gcccggagag atcccctcga     540
taatggatta ctaaatggga tacacgctgt accagttcgc tccgagcccc ggccgcctgt     600
ccgtcgatgc accgaaaagg gtgaagtaga gaaataaagt ctccccgctg aactactatg     660
aggtcagaag ccttgctgct atatttcaca ctgctacact ttgctggggc tggtttccca     720
gaagattctg agccaatcag tatttcgcat ggcaactata caaaacagta tccggtgttt     780
gtgggccaca gccaggacg aacaccaca cagaggcaca ggctggacat ccagatgatt       840
atgatcatga acggaaccct ctacattgct gctagggacc atatttatac tgttgatata     900
gacacatcac acacggaaga aatttattgt agcaaaaaac tgacatggaa atctagacag     960
gccgatgtag acacatgcag aatgaaggga aaacataagg atgagtgcca caactttatt    1020
aaagttcttc taaagaaaaa cgatgatgca ttgtttgtct gtggaactaa tgccttcaac    1080
ccttcctgca gaaactataa gatggataca ttggaaccat cggggatga attcagcgga     1140
atggccagat gcccatatga tgccaaacat gccaacgttg cactgtttgc agatggaaaa    1200
ctatactcag ccacagtgac tgacttcctt gccattgacg cagtcatttta ccggagtctt    1260
ggagaaagcc ctaccctgcg gaccgtcaag cacgattcaa aatggttgaa agaaccatac    1320
tttgttcaag ccgtggatta cggagattat atctacttct tcttcaggga aatagcagtg    1380
gagtataaca ccatgggaaa ggtagttttc ccaagagtgg ctcaggtttg taagaatgat    1440
atgggaggat ctcaaagagt cctggagaaa cagtggacgt cgttcctgaa ggcgcgcttg    1500
aactgctcag ttcctggaga ctctcatttt tatttcaaca ttctccaggc agttacagat    1560
gtgattcgta tcaacgggcg tgatgttgtc ctggcaacgt tttctacacc ttataacagc    1620
atccctgggt ctgcagtctg tgcctatgac atgcttgaca ttgccagtgt ttttactggg    1680
agattcaagg aacagaagtc tcctgattcc acctggacac cagttcctga tgaacgagtt    1740
cctaagccca ggccaggttg ctgtgctggc tcatcctcct tagaaagata tgcaacctcc    1800
aatgagttcc ctgatgatac cctgaacttc atcaagacgc accgctcat ggatgaggca    1860
gtgccctcca tcttcaacag gccatggttc ctgaacacaa tggtcagata ccgccttacc    1920
aaaattgcag tggacacagc tgctgggcca tatcagaatc acactgtggt ttttctggga    1980
tcagagaagg gaatcatctt gaagtttttg gccagaatag gaaatagtgg tttttctaaat    2040
gacagccttt tcctggagga tgagtgtgt tacaactctg aaaaatgcag ctatgatgga    2100
gtcgaagaca aaaggatcat gggcatgcag ctgacagag caagcagctc tctgtatgtt    2160
gcgttctcta cctgtgtgat aaaggttccc cttggccggt gtgaacgaca tgggaagtgt    2220
aaaaaaaacct gtattgcctc cagagaccca tattgtggat ggataaagga aggtggtgcc    2280
```

```
tgcagccatt tatcacccaa cagcagactg acttttgagc aggacataga gcgtggcaat    2340
acagatggtc tgggggactg tcacaattcc tttgtggcac tgaatgggca ttccagttcc    2400
ctcttgccca gcacaaccac atcagattcg acggctcaag aggggtatga gtctagggga    2460
ggaatgctgg actggaagca tctgcttgac tcacctgaca gcacagaccc tttggggca    2520 gtgtcttccc ataatcacca agacaagaag ggagtgattc gggaaagtta cctcaaaggc    2580
cacgaccagc tggttcccgt caccctcttg gccattgcag tcatcctggc tttcgtcatg    2640
ggggccgtct tctcgggcat caccgtctac tgcgtctgtg atcatcggcg caaagacgtg    2700
gctgtggtga gcgcaagga gaaggagctc acccactcgc gccggggctc catgagcagc    2760
gtcaccaagc tcagcggcct ctttggggac actcaatcca agacccaaa gccggaggcc    2820 atcctcacgc cactcatgca aacggcaag ctcgccactc ccggcaacac ggccaagatg    2880
ctcattaaag cagaccagca ccacctggac ctgacggccc tccccacccc agagtcaacc    2940
ccaacgctgc agcagaagcg gaagcccagc cgcggcagcc gcgagtggga gaggaaccag    3000
aacctcatca atgcctgcac aaaggacatg cccccatgg gctcccctgt gattcccacg    3060
gacctgcccc tgcgggcctc ccccagccac atccccagcg tggtggtcct gcccatcacg    3120
cagcagggct accagcatga gtacgtggac cagcccaaaa tgagcgaggt ggcccagatg    3180
gcgctggagg accaggccgc cacactggag tataagacca tcaaggaaca tctcagcagc    3240
aagagtccca accatggggt gaaccttgtg agaacctgg acagcctgcc ccccaaagtt    3300
ccacagcggg aggcctccct gggtcccccg ggagcctccc tgtctcagac cggtctaagc    3360
aagcggctgg aaatgcacca ctcctcttcc tacggggttg actataagag gagctacccc    3420
acgaactcgc tcacgagaag ccaccaggcc accactctca aaagaaacaa cactaactcc    3480
tccaattcct ctcacctctc cagaaaccag agctttggca ggggagacaa cccgccgccc    3540
gccccgcaga gggtggactc catccaggtg cacagctccc agccatctgg ccaggccgtg    3600
actgtctcga ggcagcccag cctcaacgcc tacaactcac tgacaaggtc ggggctgaag    3660
cgtacgccct cgctaaagcc ggacgtaccc cccaaaccat cctttgctcc cctttccaca    3720
tccatgaagc ccaatgatgc gtgtacataa tcccaggggg aggggtcag gtgtcgaacc    3780 agcaggcaag gcgaggtgcc cgctcagctc agcaaggttc tcaactgcct cgagtaccca    3840
ccagaccaag aaggcctgcg gc                                            3862

<210> SEQ ID NO 2
<211> LENGTH: 1030
<212> TYPE: PRT
<213> ORGANISM: Homo sapiens

<400> SEQUENCE: 2

Met Arg Ser Glu Ala Leu Leu Tyr Phe Thr Leu Leu His Phe Ala
1               5                   10                  15

Gly Ala Gly Phe Pro Glu Asp Ser Glu Pro Ile Ser Ile Ser His Gly
            20                  25                  30

Asn Tyr Thr Lys Gln Tyr Pro Val Phe Val Gly His Lys Pro Gly Arg
        35                  40                  45

Asn Thr Thr Gln Arg His Arg Leu Asp Ile Gln Met Ile Met Ile Met
    50                  55                  60

Asn Gly Thr Leu Tyr Ile Ala Ala Arg Asp His Ile Tyr Thr Val Asp
65                  70                  75                  80

Ile Asp Thr Ser His Thr Glu Glu Ile Tyr Cys Ser Lys Lys Leu Thr
```

```
                        85                  90                  95
Trp Lys Ser Arg Gln Ala Asp Val Asp Thr Cys Arg Met Lys Gly Lys
                100                 105                 110

His Lys Asp Glu Cys His Asn Phe Ile Lys Val Leu Leu Lys Lys Asn
            115                 120                 125

Asp Asp Ala Leu Phe Val Cys Gly Thr Asn Ala Phe Asn Pro Ser Cys
        130                 135                 140

Arg Asn Tyr Lys Met Asp Thr Leu Glu Pro Phe Gly Asp Glu Phe Ser
145                 150                 155                 160

Gly Met Ala Arg Cys Pro Tyr Asp Ala Lys His Ala Asn Val Ala Leu
                165                 170                 175

Phe Ala Asp Gly Lys Leu Tyr Ser Ala Thr Val Thr Asp Phe Leu Ala
            180                 185                 190

Ile Asp Ala Val Ile Tyr Arg Ser Leu Gly Glu Ser Pro Thr Leu Arg
        195                 200                 205

Thr Val Lys His Asp Ser Lys Trp Leu Lys Glu Pro Tyr Phe Val Gln
    210                 215                 220

Ala Val Asp Tyr Gly Asp Tyr Ile Tyr Phe Phe Arg Glu Ile Ala
225                 230                 235                 240

Val Glu Tyr Asn Thr Met Gly Lys Val Val Phe Pro Arg Val Ala Gln
                245                 250                 255

Val Cys Lys Asn Asp Met Gly Gly Ser Gln Arg Val Leu Glu Lys Gln
            260                 265                 270

Trp Thr Ser Phe Leu Lys Ala Arg Leu Asn Cys Ser Val Pro Gly Asp
        275                 280                 285

Ser His Phe Tyr Phe Asn Ile Leu Gln Ala Val Thr Asp Val Ile Arg
    290                 295                 300

Ile Asn Gly Arg Asp Val Val Leu Ala Thr Phe Ser Thr Pro Tyr Asn
305                 310                 315                 320

Ser Ile Pro Gly Ser Ala Val Cys Ala Tyr Asp Met Leu Asp Ile Ala
                325                 330                 335

Ser Val Phe Thr Gly Arg Phe Lys Glu Gln Lys Ser Pro Asp Ser Thr
            340                 345                 350

Trp Thr Pro Val Pro Asp Glu Arg Val Pro Lys Pro Arg Pro Gly Cys
        355                 360                 365

Cys Ala Gly Ser Ser Leu Glu Arg Tyr Ala Thr Ser Asn Glu Phe
    370                 375                 380

Pro Asp Asp Thr Leu Asn Phe Ile Lys Thr His Pro Leu Met Asp Glu
385                 390                 395                 400

Ala Val Pro Ser Ile Phe Asn Arg Pro Trp Phe Leu Arg Thr Met Val
                405                 410                 415

Arg Tyr Arg Leu Thr Lys Ile Ala Val Asp Thr Ala Ala Gly Pro Tyr
            420                 425                 430

Gln Asn His Thr Val Val Phe Leu Gly Ser Glu Lys Gly Ile Ile Leu
        435                 440                 445

Lys Phe Leu Ala Arg Ile Gly Asn Ser Gly Phe Leu Asn Asp Ser Leu
    450                 455                 460

Phe Leu Glu Glu Met Ser Val Tyr Asn Ser Glu Lys Cys Ser Tyr Asp
465                 470                 475                 480

Gly Val Glu Asp Lys Arg Ile Met Gly Met Gln Leu Asp Arg Ala Ser
                485                 490                 495

Ser Ser Leu Tyr Val Ala Phe Ser Thr Cys Val Ile Lys Val Pro Leu
            500                 505                 510
```

```
Gly Arg Cys Glu Arg His Gly Lys Cys Lys Thr Cys Ile Ala Ser
    515                 520                 525

Arg Asp Pro Tyr Cys Gly Trp Ile Lys Glu Gly Ala Cys Ser His
    530                 535                 540

Leu Ser Pro Asn Ser Arg Leu Thr Phe Glu Gln Asp Ile Glu Arg Gly
545                 550                 555                 560

Asn Thr Asp Gly Leu Gly Asp Cys His Asn Ser Phe Val Ala Leu Asn
                565                 570                 575

Gly His Ser Ser Leu Leu Pro Ser Thr Thr Ser Asp Ser Thr
            580                 585                 590

Ala Gln Glu Gly Tyr Glu Ser Arg Gly Gly Met Leu Asp Trp Lys His
    595                 600                 605

Leu Leu Asp Ser Pro Asp Ser Thr Asp Pro Leu Gly Ala Val Ser Ser
    610                 615                 620

His Asn His Gln Asp Lys Lys Gly Val Ile Arg Glu Ser Tyr Leu Lys
625                 630                 635                 640

Gly His Asp Gln Leu Val Pro Val Thr Leu Leu Ala Ile Ala Val Ile
                645                 650                 655

Leu Ala Phe Val Met Gly Ala Val Phe Ser Gly Ile Thr Val Tyr Cys
                660                 665                 670

Val Cys Asp His Arg Arg Lys Asp Val Ala Val Val Gln Arg Lys Glu
    675                 680                 685

Lys Glu Leu Thr His Ser Arg Arg Gly Ser Met Ser Ser Val Thr Lys
    690                 695                 700

Leu Ser Gly Leu Phe Gly Asp Thr Gln Ser Lys Asp Pro Lys Pro Glu
705                 710                 715                 720

Ala Ile Leu Thr Pro Leu Met His Asn Gly Lys Leu Ala Thr Pro Gly
                725                 730                 735

Asn Thr Ala Lys Met Leu Ile Lys Ala Asp Gln His His Leu Asp Leu
                740                 745                 750

Thr Ala Leu Pro Thr Pro Glu Ser Thr Pro Thr Leu Gln Gln Lys Arg
    755                 760                 765

Lys Pro Ser Arg Gly Ser Arg Glu Trp Glu Arg Asn Gln Asn Leu Ile
    770                 775                 780

Asn Ala Cys Thr Lys Asp Met Pro Pro Met Gly Ser Pro Val Ile Pro
785                 790                 795                 800

Thr Asp Leu Pro Leu Arg Ala Ser Pro Ser His Ile Pro Ser Val Val
                805                 810                 815

Val Leu Pro Ile Thr Gln Gln Gly Tyr Gln His Glu Tyr Val Asp Gln
                820                 825                 830

Pro Lys Met Ser Glu Val Ala Gln Met Ala Leu Glu Asp Gln Ala Ala
    835                 840                 845

Thr Leu Glu Tyr Lys Thr Ile Lys Glu His Leu Ser Ser Lys Ser Pro
    850                 855                 860

Asn His Gly Val Asn Leu Val Glu Asn Leu Asp Ser Leu Pro Pro Lys
865                 870                 875                 880

Val Pro Gln Arg Glu Ala Ser Leu Gly Pro Pro Gly Ala Ser Leu Ser
                885                 890                 895

Gln Thr Gly Leu Ser Lys Arg Leu Glu Met His His Ser Ser Ser Tyr
                900                 905                 910

Gly Val Asp Tyr Lys Arg Ser Tyr Pro Thr Asn Ser Leu Thr Arg Ser
                915                 920                 925
```

```
His Gln Ala Thr Thr Leu Lys Arg Asn Asn Thr Asn Ser Ser Asn Ser
    930                 935                 940

Ser His Leu Ser Arg Asn Gln Ser Phe Gly Arg Gly Asp Asn Pro Pro
945                 950                 955                 960

Pro Ala Pro Gln Arg Val Asp Ser Ile Gln Val His Ser Ser Gln Pro
                965                 970                 975

Ser Gly Gln Ala Val Thr Val Ser Arg Gln Pro Ser Leu Asn Ala Tyr
            980                 985                 990

Asn Ser Leu Thr Arg Ser Gly Leu Lys Arg Thr Pro Ser Leu Lys Pro
        995                 1000                1005

Asp Val Pro Pro Lys Pro Ser Phe Ala Pro Leu Ser Thr Ser Met
    1010                1015                1020

Lys Pro Asn Asp Ala Cys Thr
    1025                1030

<210> SEQ ID NO 3
<211> LENGTH: 4244
<212> TYPE: DNA
<213> ORGANISM: Homo sapiens

<400> SEQUENCE: 3
```

| | | | | | |
|---|---|---|---|---|---|
| atcgcgtttg | catcccagaa | agtagtcgcc | gcgactattt | cccccaaaga | gacaagcaca | 60 |
| catgtaggaa | tgacaaaggc | ttgcgaagga | gagagcgcag | cccgcggccc | ggagagatcc | 120 |
| cctcgataat | ggattactaa | atgggataca | cgctgtacca | gttcgctccg | agccccggcc | 180 |
| gcctgtccgt | cgatgcaccg | aaaagggtga | agtagagaaa | taaagtctcc | ccgctgaact | 240 |
| actatgaggt | cagaagcctt | gctgctatat | ttcacactgc | tacactttgc | tggggctggt | 300 |
| ttcccagaag | attctgagcc | aatcagtatt | tcgcatggca | actatacaaa | acagtatccg | 360 |
| gtgtttgtgg | gccacaagcc | aggacggaac | accacacaga | ggcacaggct | ggacatccag | 420 |
| atgattatga | tcatgaacgg | aaccctctac | attgctgcta | gggaccatat | ttatactgtt | 480 |
| gatatagaca | catcacacac | ggaagaaatt | tattgtagca | aaaaactgac | atggaaatct | 540 |
| agacaggccg | atgtagacac | atgcagaatg | aagggaaaac | ataaggatga | gtgccacaac | 600 |
| tttattaaag | ttcttctaaa | gaaaaacgat | gatgcattgt | ttgtctgtgg | aactaatgcc | 660 |
| ttcaacccctt | cctgcagaaa | ctataagatg | gatacattgg | aaccattcgg | ggatgaattc | 720 |
| agcggaatgg | ccagatgccc | atatgatgcc | aaacatgcca | acgttgcact | gtttgcagat | 780 |
| ggaaaactat | actcagccac | agtgactgac | ttccttgcca | ttgacgcagt | catttaccgg | 840 |
| agtcttggag | aaagccctac | cctgcggacc | gtcaagcacg | attcaaaatg | gttgaaagaa | 900 |
| ccatactttg | ttcaagccgt | ggattacgga | gattatatct | acttcttctt | cagggaaata | 960 |
| gcagtggagt | ataacaccat | gggaaaggta | gttttcccaa | gagtggctca | ggtttgtaag | 1020 |
| aatgatatgg | gaggatctca | aagagtcctg | gagaaacagt | ggacgtcgtt | cctgaaggcg | 1080 |
| cgcttgaact | gctcagttcc | tggagactct | catttttatt | tcaacattct | ccaggcagtt | 1140 |
| acagatgtga | ttcgtatcaa | cgggcgtgat | gttgtcctgg | caacgttttc | tacacccttat | 1200 |
| aacagcatcc | ctgggtctgc | agtctgtgcc | tatgacatgc | ttgacattgc | cagtgttttt | 1260 |
| actgggagat | tcaaggaaca | gaagtctcct | gattccacct | ggacaccagt | tcctgatgaa | 1320 |
| cgagttccta | agcccaggcc | aggttgctgt | gctggctcat | cctccttaga | aagatatgca | 1380 |
| acctccaatg | agttccctga | tgataccctg | aacttcatca | agacgcaccc | gctcatggat | 1440 |
| gaggcagtgc | cctccatctt | caacaggcca | tggttcctga | aacaatggt | cagataccgc | 1500 |

```
cttaccaaaa ttgcagtgga cacagctgct gggccatatc agaatcacac tgtggttttt    1560
ctgggatcag agaagggaat catcttgaag ttttggcca gaataggaaa tagtggtttt    1620
ctaaatgaca gccttttcct ggaggagatg agtgtttaca actctgaaaa atgcagctat    1680
gatggagtcg aagacaaaag gatcatgggc atgcagctgg acagagcaag cagctctctg    1740
tatgttgcgt tctctacctg tgtgataaag gttccccttg gccggtgtga acgacatggg    1800
aagtgtaaaa aaacctgtat tgcctccaga gacccatatt gtggatggat aaaggaaggt    1860
ggtgcctgca gccatttatc acccaacagc agactgactt ttgagcagga catagagcgt    1920
ggcaatacag atggtctggg ggactgtcac aattcctttg tggcactgaa tgacatttca    1980
actcctctac cagataatga aatgtcttac aacacagtgt atgggcattc cagttccctc    2040
ttgcccagca caaccacatc agattcgacg gctcaagagg ggtatgagtc taggggagga    2100
atgctggact ggaagcatct gcttgactca cctgacagca cagacccttt ggggcagtg    2160 tcttcccata atcaccaaga caagaaggga gtgattcggg aaagttacct caaaggccac    2220
gaccagctgg ttcccgtcac cctcttggcc attgcagtca tcctggcttt cgtcatgggg    2280
gccgtcttct cgggcatcac cgtctactgc gtctgtgatc atcggcgcaa agacgtggct    2340
gtggtgcagc gcaaggagaa ggagctcacc cactcgcgcc ggggctccat gagcagcgtc    2400
accaagctca gcggcctctt tggggacact caatccaaag acccaaagcc ggaggccatc    2460
ctcacgccac tcatgcacaa cggcaagctc gccactcccg caacacggc caagatgctc    2520 attaaagcag accagcacca cctggacctg acggccctcc ccaccccaga gtcaacccca    2580
acgctgcagc agaagcggaa gcccagccgc ggcagccgcg agtgggagag gaaccagaac    2640
ctcatcaatg cctgcacaaa ggacatgccc cccatgggct cccctgtgat tcccacggac    2700 ctgccctgc gggcctcccc cagccacatc ccagcgtgg tggtcctgcc catcacgcag    2760
cagggctacc agcatgagta cgtggaccag cccaaaatga gcgaggtggc ccagatggcg    2820
ctggaggacc aggccgccac actggagtat aagaccatca aggaacatct cagcagcaag    2880
agtcccaacc atggggtgaa ccttgtggag aacctggaca gcctgccccc caagttcca    2940 cagcggagg cctccctggg tccccgggga gcctccctgt ctcagaccgg tctaagcaag    3000
cggctggaaa tgcaccactc ctcttcctac ggggttgact ataagaggag ctaccccacg    3060
aactcgctca cgagaagcca ccaggccacc actctcaaaa gaacaacac taactcctcc    3120 aattcctctc acctctccag aaaccagagc tttggcaggg gagacaaccc gccgccgcc    3180 ccgcagaggg tggactccat ccaggtgcac agctcccagc catctggcca ggccgtgact    3240
gtctcgaggc agcccagcct caacgcctac aactcactga caaggtcggg gctgaagcgt    3300 acgcctcgc taaagccgga cgtaccccc aaaccatcct ttgctcccct ttccacatcc    3360
atgaagccca atgatgcgtg tacataatcc caggggagg gggtcaggtg tcgaaccagc    3420
aggcaaggcg aggtgcccgc tcagctcagc aaggttctca actgcctcga gtacccacca    3480
gaccaagaag gcctgcggca gagccgagga cgctgggtcc tcctctctgg acacagggg    3540 tactcacgaa aactgggccg cgtggttggg tgaaggtttg caacggcggg gactcacctt    3600
cattctcttc cttcactttc ccccacaccc tacaacaggt cggacccaca aaagacttca    3660
gttatcatca caaacatgag ccaaaagcac atacctaccc catccccac ccccacacac    3720 acacacacat gcacacaaca catacacaca cacgcacaga ggtgaacaga aactgaaaca    3780
ttttgtccac aacttcacgg gacgtggcca gactgggttt cgttccaac ctgcaaaaca    3840 caaatacatt ttttaaaatc aagaaaattt aaaaagacaa aaaaaaaaga attcattgat    3900
```

-continued

```
aattctaact cagactttaa caatggcaga agtttactat gcgcaaatac tgtgaaatgc    3960
ccgccagtgt tacagctttc tgttgcagca gataaatgcc atgttgggca actatgtcat    4020
agatttctgc tcctcctctc ttttaatgaa ataacgtgac cgttaacgca agtaactctt    4080
tatttattgt tcacccttt  tttccttaag gaaaggactc ttccaaatat catcctatga    4140
acagctcttc agaaagccca ttgaaagtta aactatttaa cgtgaaatcc attaactgga    4200
ataattgagt ttctttattt ttacaataaa ttcactgagt aaat                    4244
```

<210> SEQ ID NO 4
<211> LENGTH: 1047
<212> TYPE: PRT
<213> ORGANISM: Homo sapiens

<400> SEQUENCE: 4

```
Met Arg Ser Glu Ala Leu Leu Tyr Phe Thr Leu Leu His Phe Ala
1               5                   10                  15

Gly Ala Gly Phe Pro Glu Asp Ser Glu Pro Ile Ser Ile Ser His Gly
            20                  25                  30

Asn Tyr Thr Lys Gln Tyr Pro Val Phe Val Gly His Lys Pro Gly Arg
        35                  40                  45

Asn Thr Thr Gln Arg His Arg Leu Asp Ile Gln Met Ile Met Ile Met
    50                  55                  60

Asn Gly Thr Leu Tyr Ile Ala Ala Arg Asp His Ile Tyr Thr Val Asp
65                  70                  75                  80

Ile Asp Thr Ser His Thr Glu Glu Ile Tyr Cys Ser Lys Lys Leu Thr
                85                  90                  95

Trp Lys Ser Arg Gln Ala Asp Val Asp Thr Cys Arg Met Lys Gly Lys
            100                 105                 110

His Lys Asp Glu Cys His Asn Phe Ile Lys Val Leu Leu Lys Lys Asn
        115                 120                 125

Asp Asp Ala Leu Phe Val Cys Gly Thr Asn Ala Phe Asn Pro Ser Cys
    130                 135                 140

Arg Asn Tyr Lys Met Asp Thr Leu Glu Pro Phe Gly Asp Glu Phe Ser
145                 150                 155                 160

Gly Met Ala Arg Cys Pro Tyr Asp Ala Lys His Ala Asn Val Ala Leu
                165                 170                 175

Phe Ala Asp Gly Lys Leu Tyr Ser Ala Thr Val Thr Asp Phe Leu Ala
            180                 185                 190

Ile Asp Ala Val Ile Tyr Arg Ser Leu Gly Glu Ser Pro Thr Leu Arg
        195                 200                 205

Thr Val Lys His Asp Ser Lys Trp Leu Lys Glu Pro Tyr Phe Val Gln
    210                 215                 220

Ala Val Asp Tyr Gly Asp Tyr Ile Tyr Phe Phe Arg Glu Ile Ala
225                 230                 235                 240

Val Glu Tyr Asn Thr Met Gly Lys Val Val Phe Pro Arg Val Ala Gln
                245                 250                 255

Val Cys Lys Asn Asp Met Gly Gly Ser Gln Arg Val Leu Glu Lys Gln
            260                 265                 270

Trp Thr Ser Phe Leu Lys Ala Arg Leu Asn Cys Ser Val Pro Gly Asp
        275                 280                 285

Ser His Phe Tyr Phe Asn Ile Leu Gln Ala Val Thr Asp Val Ile Arg
    290                 295                 300

Ile Asn Gly Arg Asp Val Val Leu Ala Thr Phe Ser Thr Pro Tyr Asn
```

-continued

```
305                 310                 315                 320
Ser Ile Pro Gly Ser Ala Val Cys Ala Tyr Asp Met Leu Asp Ile Ala
                325                 330                 335

Ser Val Phe Thr Gly Arg Phe Lys Glu Gln Lys Ser Pro Asp Ser Thr
                340                 345                 350

Trp Thr Pro Val Pro Asp Glu Arg Val Pro Lys Pro Arg Pro Gly Cys
                355                 360                 365

Cys Ala Gly Ser Ser Ser Leu Glu Arg Tyr Ala Thr Ser Asn Glu Phe
        370                 375                 380

Pro Asp Asp Thr Leu Asn Phe Ile Lys Thr His Pro Leu Met Asp Glu
385                 390                 395                 400

Ala Val Pro Ser Ile Phe Asn Arg Pro Trp Phe Leu Arg Thr Met Val
                405                 410                 415

Arg Tyr Arg Leu Thr Lys Ile Ala Val Asp Thr Ala Ala Gly Pro Tyr
                420                 425                 430

Gln Asn His Thr Val Val Phe Leu Gly Ser Glu Lys Gly Ile Ile Leu
            435                 440                 445

Lys Phe Leu Ala Arg Ile Gly Asn Ser Gly Phe Leu Asn Asp Ser Leu
        450                 455                 460

Phe Leu Glu Glu Met Ser Val Tyr Asn Ser Glu Lys Cys Ser Tyr Asp
465                 470                 475                 480

Gly Val Glu Asp Lys Arg Ile Met Gly Met Gln Leu Asp Arg Ala Ser
                485                 490                 495

Ser Ser Leu Tyr Val Ala Phe Ser Thr Cys Val Ile Lys Val Pro Leu
            500                 505                 510

Gly Arg Cys Glu Arg His Gly Lys Cys Lys Lys Thr Cys Ile Ala Ser
        515                 520                 525

Arg Asp Pro Tyr Cys Gly Trp Ile Lys Glu Gly Ala Cys Ser His
530                 535                 540

Leu Ser Pro Asn Ser Arg Leu Thr Phe Glu Gln Asp Ile Glu Arg Gly
545                 550                 555                 560

Asn Thr Asp Gly Leu Gly Asp Cys His Asn Ser Phe Val Ala Leu Asn
                565                 570                 575

Asp Ile Ser Thr Pro Leu Pro Asp Asn Glu Met Ser Tyr Asn Thr Val
                580                 585                 590

Tyr Gly His Ser Ser Ser Leu Leu Pro Ser Thr Thr Thr Ser Asp Ser
            595                 600                 605

Thr Ala Gln Glu Gly Tyr Glu Ser Arg Gly Gly Met Leu Asp Trp Lys
        610                 615                 620

His Leu Leu Asp Ser Pro Asp Ser Thr Asp Pro Leu Gly Ala Val Ser
625                 630                 635                 640

Ser His Asn His Gln Asp Lys Lys Gly Val Ile Arg Glu Ser Tyr Leu
                645                 650                 655

Lys Gly His Asp Gln Leu Val Pro Val Thr Leu Leu Ala Ile Ala Val
                660                 665                 670

Ile Leu Ala Phe Val Met Gly Ala Val Phe Ser Gly Ile Thr Val Tyr
            675                 680                 685

Cys Val Cys Asp His Arg Arg Lys Asp Val Ala Val Gln Arg Lys
        690                 695                 700

Glu Lys Glu Leu Thr His Ser Arg Arg Gly Ser Met Ser Ser Val Thr
705                 710                 715                 720

Lys Leu Ser Gly Leu Phe Gly Asp Thr Gln Ser Lys Asp Pro Lys Pro
                725                 730                 735
```

Glu Ala Ile Leu Thr Pro Leu Met His Asn Gly Lys Leu Ala Thr Pro
            740                 745                 750

Gly Asn Thr Ala Lys Met Leu Ile Lys Ala Asp Gln His His Leu Asp
            755                 760                 765

Leu Thr Ala Leu Pro Thr Pro Glu Ser Thr Pro Thr Leu Gln Gln Lys
770                 775                 780

Arg Lys Pro Ser Arg Gly Ser Arg Glu Trp Glu Arg Asn Gln Asn Leu
785                 790                 795                 800

Ile Asn Ala Cys Thr Lys Asp Met Pro Pro Met Gly Ser Pro Val Ile
                805                 810                 815

Pro Thr Asp Leu Pro Leu Arg Ala Ser Pro Ser His Ile Pro Ser Val
            820                 825                 830

Val Val Leu Pro Ile Thr Gln Gln Gly Tyr Gln His Glu Tyr Val Asp
            835                 840                 845

Gln Pro Lys Met Ser Glu Val Ala Gln Met Ala Leu Glu Asp Gln Ala
            850                 855                 860

Ala Thr Leu Glu Tyr Lys Thr Ile Lys Glu His Leu Ser Ser Lys Ser
865                 870                 875                 880

Pro Asn His Gly Val Asn Leu Val Glu Asn Leu Asp Ser Leu Pro Pro
                885                 890                 895

Lys Val Pro Gln Arg Glu Ala Ser Leu Gly Pro Pro Gly Ala Ser Leu
            900                 905                 910

Ser Gln Thr Gly Leu Ser Lys Arg Leu Glu Met His His Ser Ser Ser
            915                 920                 925

Tyr Gly Val Asp Tyr Lys Arg Ser Tyr Pro Thr Asn Ser Leu Thr Arg
            930                 935                 940

Ser His Gln Ala Thr Thr Leu Lys Arg Asn Asn Thr Asn Ser Ser Asn
945                 950                 955                 960

Ser Ser His Leu Ser Arg Asn Gln Ser Phe Gly Arg Gly Asp Asn Pro
                965                 970                 975

Pro Pro Ala Pro Gln Arg Val Asp Ser Ile Gln Val His Ser Ser Gln
            980                 985                 990

Pro Ser Gly Gln Ala Val Thr Val Ser Arg Gln Pro Ser Leu Asn Ala
            995                 1000                1005

Tyr Asn Ser Leu Thr Arg Ser Gly Leu Lys Arg Thr Pro Ser Leu
            1010                1015                1020

Lys Pro Asp Val Pro Pro Lys Pro Ser Phe Ala Pro Leu Ser Thr
            1025                1030                1035

Ser Met Lys Pro Asn Asp Ala Cys Thr
            1040                1045

<210> SEQ ID NO 5

<400> SEQUENCE: 5

000

<210> SEQ ID NO 6
<211> LENGTH: 971
<212> TYPE: PRT
<213> ORGANISM: Homo sapiens

<400> SEQUENCE: 6

Met Arg Ser Glu Ala Leu Leu Leu Tyr Phe Thr Leu Leu His Phe Ala
1               5                   10                  15

```
Gly Ala Gly Phe Pro Glu Asp Ser Glu Pro Ile Ser Ile Ser His Gly
             20                  25                  30
Asn Tyr Thr Lys Gln Tyr Pro Val Phe Val Gly His Lys Pro Gly Arg
         35                  40                  45
Asn Thr Thr Gln Arg His Arg Leu Asp Ile Gln Met Ile Met Ile Met
     50                  55                  60
Asn Gly Thr Leu Tyr Ile Ala Ala Arg Asp His Ile Tyr Thr Val Asp
 65                  70                  75                  80
Ile Asp Thr Ser His Thr Glu Glu Ile Tyr Cys Ser Lys Lys Leu Thr
                 85                  90                  95
Trp Lys Ser Arg Gln Ala Asp Val Asp Thr Cys Arg Met Lys Gly Lys
             100                 105                 110
His Lys Asp Glu Cys His Asn Phe Ile Lys Val Leu Leu Lys Lys Asn
         115                 120                 125
Asp Asp Ala Leu Phe Val Cys Gly Thr Asn Ala Phe Asn Pro Ser Cys
    130                 135                 140
Arg Asn Tyr Lys Met Asp Thr Leu Glu Pro Phe Gly Asp Glu Phe Ser
145                 150                 155                 160
Gly Met Ala Arg Cys Pro Tyr Asp Ala Lys His Ala Asn Val Ala Leu
                165                 170                 175
Phe Ala Asp Gly Lys Leu Tyr Ser Ala Thr Val Thr Asp Phe Leu Ala
            180                 185                 190
Ile Asp Ala Val Ile Tyr Arg Ser Leu Gly Glu Ser Pro Thr Leu Arg
        195                 200                 205
Thr Val Lys His Asp Ser Lys Trp Leu Lys Glu Pro Tyr Phe Val Gln
    210                 215                 220
Ala Val Asp Tyr Gly Asp Tyr Ile Tyr Phe Phe Arg Glu Ile Ala
225                 230                 235                 240
Val Glu Tyr Asn Thr Met Gly Lys Val Val Phe Pro Arg Val Ala Gln
                245                 250                 255
Val Cys Lys Asn Asp Met Gly Gly Ser Gln Arg Val Leu Glu Lys Gln
            260                 265                 270
Trp Thr Ser Phe Leu Lys Ala Arg Leu Asn Cys Ser Val Pro Gly Asp
        275                 280                 285
Ser His Phe Tyr Phe Asn Ile Leu Gln Ala Val Thr Asp Val Ile Arg
    290                 295                 300
Ile Asn Gly Arg Asp Val Val Leu Ala Thr Phe Ser Thr Pro Tyr Asn
305                 310                 315                 320
Ser Ile Pro Gly Ser Ala Val Cys Ala Tyr Asp Met Leu Asp Ile Ala
                325                 330                 335
Ser Val Phe Thr Gly Arg Phe Lys Glu Gln Lys Ser Pro Asp Ser Thr
            340                 345                 350
Trp Thr Pro Val Pro Asp Glu Arg Val Pro Lys Pro Arg Pro Gly Cys
        355                 360                 365
Cys Ala Gly Ser Ser Ser Leu Glu Arg Tyr Ala Thr Ser Asn Glu Phe
    370                 375                 380
Pro Asp Asp Thr Leu Asn Phe Ile Lys Thr His Pro Leu Met Asp Glu
385                 390                 395                 400
Ala Val Pro Ser Ile Phe Asn Arg Pro Trp Phe Leu Arg Thr Met Val
                405                 410                 415
Arg Cys Ser Tyr Asp Gly Val Glu Asp Lys Arg Ile Met Gly Met Gln
            420                 425                 430
Leu Asp Arg Ala Ser Ser Ser Leu Tyr Val Ala Phe Ser Thr Cys Val
```

```
                435                 440                 445
Ile Lys Val Pro Leu Gly Arg Cys Glu Arg His Gly Lys Cys Lys Lys
450                 455                 460
Thr Cys Ile Ala Ser Arg Asp Pro Tyr Cys Gly Trp Ile Lys Glu Gly
465                 470                 475                 480
Gly Ala Cys Ser His Leu Ser Pro Asn Ser Arg Leu Thr Phe Glu Gln
                485                 490                 495
Asp Ile Glu Arg Gly Asn Thr Asp Gly Leu Gly Asp Cys His Asn Ser
            500                 505                 510
Phe Val Ala Leu Asn Gly His Ser Ser Leu Leu Pro Ser Thr Thr
        515                 520                 525
Thr Ser Asp Ser Thr Ala Gln Glu Gly Tyr Glu Ser Arg Gly Gly Met
530                 535                 540
Leu Asp Trp Lys His Leu Leu Asp Ser Pro Asp Ser Thr Asp Pro Leu
545                 550                 555                 560
Gly Ala Val Ser Ser His Asn His Gln Asp Lys Lys Gly Val Ile Arg
                565                 570                 575
Glu Ser Tyr Leu Lys Gly His Asp Gln Leu Val Pro Val Thr Leu Leu
            580                 585                 590
Ala Ile Ala Val Ile Leu Ala Phe Val Met Gly Ala Val Phe Ser Gly
        595                 600                 605
Ile Thr Val Tyr Cys Val Cys Asp His Arg Arg Lys Asp Val Ala Val
610                 615                 620
Val Gln Arg Lys Glu Lys Glu Leu Thr His Ser Arg Arg Gly Ser Met
625                 630                 635                 640
Ser Ser Val Thr Lys Leu Ser Gly Leu Phe Gly Asp Thr Gln Ser Lys
                645                 650                 655
Asp Pro Lys Pro Glu Ala Ile Leu Thr Pro Leu Met His Asn Gly Lys
            660                 665                 670
Leu Ala Thr Pro Gly Asn Thr Ala Lys Met Leu Ile Lys Ala Asp Gln
        675                 680                 685
His His Leu Asp Leu Thr Ala Leu Pro Thr Pro Glu Ser Thr Pro Thr
690                 695                 700
Leu Gln Gln Lys Arg Lys Pro Ser Arg Gly Ser Arg Glu Trp Glu Arg
705                 710                 715                 720
Asn Gln Asn Leu Ile Asn Ala Cys Thr Lys Asp Met Pro Pro Met Gly
                725                 730                 735
Ser Pro Val Ile Pro Thr Asp Leu Pro Leu Arg Ala Ser Pro Ser His
            740                 745                 750
Ile Pro Ser Val Val Leu Pro Ile Thr Gln Gln Gly Tyr Gln His
        755                 760                 765
Glu Tyr Val Asp Gln Pro Lys Met Ser Glu Val Ala Gln Met Ala Leu
770                 775                 780
Glu Asp Gln Ala Ala Thr Leu Glu Tyr Lys Thr Ile Lys Glu His Leu
785                 790                 795                 800
Ser Ser Lys Ser Pro Asn His Gly Val Asn Leu Val Glu Asn Leu Asp
                805                 810                 815
Ser Leu Pro Pro Lys Val Pro Arg Glu Ala Ser Leu Gly Pro Pro
            820                 825                 830
Gly Ala Ser Leu Ser Gln Thr Gly Leu Ser Lys Arg Leu Glu Met His
        835                 840                 845
His Ser Ser Ser Tyr Gly Val Asp Tyr Lys Arg Ser Tyr Pro Thr Asn
850                 855                 860
```

-continued

Ser Leu Thr Arg Ser His Gln Ala Thr Thr Leu Lys Arg Asn Asn Thr
865                 870                 875                 880

Asn Ser Ser Asn Ser Ser His Leu Ser Arg Asn Gln Ser Phe Gly Arg
            885                 890                 895

Gly Asp Asn Pro Pro Ala Pro Gln Arg Val Asp Ser Ile Gln Val
        900                 905                 910

His Ser Ser Gln Pro Ser Gly Gln Ala Val Thr Val Ser Arg Gln Pro
        915                 920                 925

Ser Leu Asn Ala Tyr Asn Ser Leu Thr Arg Ser Gly Leu Lys Arg Thr
        930                 935                 940

Pro Ser Leu Lys Pro Asp Val Pro Pro Lys Pro Ser Phe Ala Pro Leu
945                 950                 955                 960

Ser Thr Ser Met Lys Pro Asn Asp Ala Cys Thr
            965                 970

<210> SEQ ID NO 7

<400> SEQUENCE: 7

000

<210> SEQ ID NO 8
<211> LENGTH: 975
<212> TYPE: PRT
<213> ORGANISM: Homo sapiens

<400> SEQUENCE: 8

Met Arg Ser Glu Ala Leu Leu Leu Tyr Phe Thr Leu Leu His Phe Ala
1               5                   10                  15

Gly Ala Gly Phe Pro Glu Asp Ser Glu Pro Ile Ser Ile Ser His Gly
            20                  25                  30

Asn Tyr Thr Lys Gln Tyr Pro Val Phe Val Gly His Lys Pro Gly Arg
        35                  40                  45

Asn Thr Thr Gln Arg His Arg Leu Asp Ile Gln Met Ile Met Ile Met
    50                  55                  60

Asn Gly Thr Leu Tyr Ile Ala Ala Arg Asp His Ile Tyr Thr Val Asp
65                  70                  75                  80

Ile Asp Thr Ser His Thr Glu Glu Ile Tyr Cys Ser Lys Lys Leu Thr
                85                  90                  95

Trp Lys Ser Arg Gln Ala Asp Val Asp Thr Cys Arg Met Lys Gly Lys
            100                 105                 110

His Lys Asp Glu Cys His Asn Phe Ile Lys Val Leu Leu Lys Lys Asn
        115                 120                 125

Asp Asp Ala Leu Phe Val Cys Gly Thr Asn Ala Phe Asn Pro Ser Cys
    130                 135                 140

Arg Asn Tyr Lys Met Asp Thr Leu Glu Pro Phe Gly Asp Glu Phe Ser
145                 150                 155                 160

Gly Met Ala Arg Cys Pro Tyr Asp Ala Lys His Ala Asn Val Ala Leu
                165                 170                 175

Phe Ala Asp Gly Lys Leu Tyr Ser Ala Thr Val Thr Asp Phe Leu Ala
            180                 185                 190

Ile Asp Ala Val Ile Tyr Arg Ser Leu Gly Glu Ser Pro Thr Leu Arg
        195                 200                 205

Thr Val Lys His Asp Ser Lys Trp Leu Lys Glu Pro Tyr Phe Val Gln
    210                 215                 220

```
Ala Val Asp Tyr Gly Asp Tyr Ile Tyr Phe Phe Arg Glu Ile Ala
225                 230                 235                 240

Val Glu Tyr Asn Thr Met Gly Lys Val Val Phe Pro Arg Val Ala Gln
                245                 250                 255

Val Cys Lys Asn Asp Met Gly Gly Ser Gln Arg Val Leu Glu Lys Gln
            260                 265                 270

Trp Thr Ser Phe Leu Lys Ala Arg Leu Asn Cys Ser Val Pro Gly Asp
        275                 280                 285

Ser His Phe Tyr Phe Asn Ile Leu Gln Ala Val Thr Asp Val Ile Arg
    290                 295                 300

Ile Asn Gly Arg Asp Val Val Leu Ala Thr Phe Ser Thr Pro Tyr Asn
305                 310                 315                 320

Ser Ile Pro Gly Ser Ala Val Cys Ala Tyr Asp Met Leu Asp Ile Ala
                325                 330                 335

Ser Val Phe Thr Gly Arg Phe Lys Glu Gln Lys Ser Pro Asp Ser Thr
            340                 345                 350

Trp Thr Pro Val Pro Asp Glu Arg Val Pro Lys Pro Arg Pro Gly Cys
        355                 360                 365

Cys Ala Gly Ser Ser Ser Leu Glu Arg Tyr Ala Thr Ser Asn Glu Phe
    370                 375                 380

Pro Asp Asp Thr Leu Asn Phe Ile Lys Thr His Pro Leu Met Asp Glu
385                 390                 395                 400

Ala Val Pro Ser Ile Phe Asn Arg Pro Trp Phe Leu Arg Thr Met Val
                405                 410                 415

Arg Tyr Arg Leu Thr Lys Ile Ala Val Asp Thr Ala Ala Gly Pro Tyr
            420                 425                 430

Gln Asn His Thr Val Val Phe Leu Gly Ser Glu Lys Gly Ile Ile Leu
        435                 440                 445

Lys Phe Leu Ala Arg Ile Gly Asn Ser Gly Phe Leu Asn Asp Ser Leu
    450                 455                 460

Phe Leu Glu Glu Met Ser Val Tyr Asn Ser Glu Lys Cys Ser Tyr Asp
465                 470                 475                 480

Gly Val Glu Asp Lys Arg Ile Met Gly Met Gln Leu Asp Arg Ala Ser
                485                 490                 495

Ser Ser Leu Tyr Val Ala Phe Ser Thr Cys Val Ile Lys Val Pro Leu
            500                 505                 510

Gly Arg Cys Glu Arg His Gly Lys Cys Lys Lys Thr Cys Ile Ala Ser
        515                 520                 525

Arg Asp Pro Tyr Cys Gly Trp Ile Lys Glu Gly Ala Cys Ser His
    530                 535                 540

Leu Ser Pro Asn Ser Arg Leu Thr Phe Glu Gln Asp Ile Glu Arg Gly
545                 550                 555                 560

Asn Thr Asp Gly Leu Gly Asp Cys His Asn Ser Phe Val Ala Leu Asn
                565                 570                 575

Gly Val Ile Arg Glu Ser Tyr Leu Lys Gly His Asp Gln Leu Val Pro
            580                 585                 590

Val Thr Leu Leu Ala Ile Ala Val Ile Leu Ala Phe Val Met Gly Ala
        595                 600                 605

Val Phe Ser Gly Ile Thr Val Tyr Cys Val Cys Asp His Arg Arg Lys
    610                 615                 620

Asp Val Ala Val Gln Arg Lys Glu Lys Glu Leu Thr His Ser Arg
625                 630                 635                 640

Arg Gly Ser Met Ser Ser Val Thr Lys Leu Ser Gly Leu Phe Gly Asp
```

```
                  645                 650                 655
Thr Gln Ser Lys Asp Pro Lys Pro Glu Ala Ile Leu Thr Pro Leu Met
              660                 665                 670

His Asn Gly Lys Leu Ala Thr Pro Gly Asn Thr Ala Lys Met Leu Ile
              675                 680                 685

Lys Ala Asp Gln His His Leu Asp Leu Thr Ala Leu Pro Thr Pro Glu
          690                 695                 700

Ser Thr Pro Thr Leu Gln Gln Lys Arg Lys Pro Ser Arg Gly Ser Arg
705                 710                 715                 720

Glu Trp Glu Arg Asn Gln Asn Leu Ile Asn Ala Cys Thr Lys Asp Met
                725                 730                 735

Pro Pro Met Gly Ser Pro Val Ile Pro Thr Asp Leu Pro Leu Arg Ala
              740                 745                 750

Ser Pro Ser His Ile Pro Ser Val Val Leu Pro Ile Thr Gln Gln
              755                 760                 765

Gly Tyr Gln His Glu Tyr Val Asp Gln Pro Lys Met Ser Glu Val Ala
          770                 775                 780

Gln Met Ala Leu Glu Asp Gln Ala Ala Thr Leu Glu Tyr Lys Thr Ile
785                 790                 795                 800

Lys Glu His Leu Ser Ser Lys Ser Pro Asn His Gly Val Asn Leu Val
                805                 810                 815

Glu Asn Leu Asp Ser Leu Pro Pro Lys Val Pro Gln Arg Glu Ala Ser
              820                 825                 830

Leu Gly Pro Pro Gly Ala Ser Leu Ser Gln Thr Gly Leu Ser Lys Arg
          835                 840                 845

Leu Glu Met His His Ser Ser Ser Tyr Gly Val Asp Tyr Lys Arg Ser
850                 855                 860

Tyr Pro Thr Asn Ser Leu Thr Arg Ser His Gln Ala Thr Thr Leu Lys
865                 870                 875                 880

Arg Asn Asn Thr Asn Ser Ser Asn Ser Ser His Leu Ser Arg Asn Gln
                885                 890                 895

Ser Phe Gly Arg Gly Asp Asn Pro Pro Ala Pro Gln Arg Val Asp
              900                 905                 910

Ser Ile Gln Val His Ser Ser Gln Pro Ser Gly Gln Ala Val Thr Val
          915                 920                 925

Ser Arg Gln Pro Ser Leu Asn Ala Tyr Asn Ser Leu Thr Arg Ser Gly
          930                 935                 940

Leu Lys Arg Thr Pro Ser Leu Lys Pro Asp Val Pro Pro Lys Pro Ser
945                 950                 955                 960

Phe Ala Pro Leu Ser Thr Ser Met Lys Pro Asn Asp Ala Cys Thr
              965                 970                 975

<210> SEQ ID NO 9
<211> LENGTH: 6901
<212> TYPE: DNA
<213> ORGANISM: Mus musculus

<400> SEQUENCE: 9
actcggctgc ctaggcgctc gggacgcagc acaggcgctt ttccgcggtg ccgattgccc    60
gagatgcccg cctaggagcg tgcggccgcg gccagcgtcg ccacacccgg acactgcac   120 tcggggttgc agagcggcc agagccctgc acctctgcct caacccccca caccgccccc   180
cgccctgaaa tgactagtta atgggcgctg gcaccgccga ggggactcag aagtgaatcc   240
aagtggaatt tggatttgga aaaagagttt cttgagcatt taccctggtc ctcgctggtt   300
```

```
ttcttctttt ttctgttttt tccctttttt cttttctttt tttcagttat tttattttac    360
tttttatttt tattttttat ttttggtctt cctctcacct cctcttctgt cattggagat    420
gaacacagct cgcttgcatc ccagaaagta atcgccgtga ctgttgcccc caaagagaca    480
agcacacatg taggaatgac aaaggcttgc gaaggaaaga gcgcagctca aggcccagag    540
agatcttctc gataatggat tactaaatgg gatactcgcc gtgtcagtcc gctccgagcc    600
gcggccgcct gcccgtcgat gcaccgaaaa gggtgaagta gagaagcaag tcccccgct    660 gaacctacta tgcggccagc agccttactg ctgtgtctca cactgctaca ctgcgctggg    720
gctggtttcc cagaagattc cgagccaatc agtatttcgc atggaacta tacaaaacag     780 tatccggtgt ttgtgggcca caagccagga cggaacacca cgcagaggca caggctggac    840
atccagatga tcatgatcat gaacagaacc ctctacgttg ctgctcgaga ccatatttat    900
actgttgata tagacacatc ccacacagaa gaaatttact gtagcaaaaa actgacatgg    960
aaatctagac aggctgacgt agacacatgc aggatgaagg ggaaacataa ggatgaatgt   1020
cacaacttca ttaaagttct tctcaagaag aatgatgata cgctgtttgt ctgtggaacc   1080
aatgccttca acccttcctg cagaaactac agggtcgata ccttggaaac ttttggggat   1140
gaatttagcg gaatggccag atgcccttat gatgccaaac atgccaacat cgctctgttt   1200
gcagatggaa aactctactc ggctacagtg actgactttc tggccattga tgcagtcatt   1260
tacaggagcc tcggagacag ccctaccctc aggactgtca agcatgattc aaagtggttg   1320
aaagagccgt actttgtcca agccgtggat tatgggact atatctactt cttcttcaga    1380
gaaattgcag tagaatacaa cactatgggg aaggttgttt ccctagggt ggctcaggtc    1440 tgtaagaatg acatgggagg gtctcagaga gtcctggaga agcagtggac atctttcctg   1500
aaggctcgcc tgaactgctc ggtgcctgga gactctcatt tttatttcaa tatactccag   1560
gcagttacag atgtgattcg cattaatggc cgtgatgttg tcttggcaac cttttccaca   1620
ccttataaca gcatcccagg ttctgcagtc tgtgcctatg acatgcttga cattgctaat   1680
gttttcactg ggaggttcaa ggaacagaaa tcacctgact ctacctggac acccgttcca   1740
gacgaacgag tccctaagcc caggccaggc tgttgtgctg gatcatcctc tttagaaaaa   1800
tatgcaacct ccaatgagtt tcccgatgat accctgaact tcattaagac gcatccactc   1860
atggacgagg cagtgccttc catcatcaac agaccttggt tcctgagaac aatggtcaga   1920
taccgcctga ccaaaattgc agtagacaac gctgccgggc catatcagaa tcacactgtg   1980
gttttcctgg gatcagaaaa gggaatcatc ctgaagttct tggccaggat aggaagcagt   2040
ggtttcctaa atggcagcct tttcctggag gagatgaatg tttacaaccc agaaaagtgc   2100
agctatgatg gtgtagaaga caaaaggatc atgggcatgc agctcgacag agcgagtggc   2160
tcactctatg ttgcattctc tacttgtgtg atcaaggtgc ctcttggccg ctgtgagcga   2220
catgggaagt gtaaaaaaac ctgcatcgcc tccagagacc cgtattgtgg gtgggtaagg   2280
gaaagtggtt cctgtgccca tctgtcaccc cttagcagac tgacatttga gcaggacatt   2340
gagcgtggca atacgacgg cctaggagac tgtcacaatt ccttcgtggc actgaatggg   2400
cacgccagtt ccctctatcc cagcaccact acgtcagatt cggcatcccg agacgggtat   2460
gagtctaggg gaggcatgct ggactggaac gacctgctcg aggcacctgg cagcacagac   2520
cctttggggg cagtgtcctc tcataaccac caggacaaga agggagtgat tcggaaaagt   2580
tacctcaaaa gcaacgacca gcttgttcct gtcaccctcc tggccattgc agtcattctg   2640
```

```
gcttttgtca tggggccgt cttctcgggc atcatcgtgt attgtgtgtg cgatcaccgg    2700
cgcaaagacg tggcagtagt gcagcgcaag gagaaagagc tcactcactc gcgtcgggga    2760
tctatgagca gtgtcaccaa gctcagtggc ctctttgggg acacccagtc caaggaccca    2820
aagcctgagg ccatcctcac accactcatg cacaacggca agctggccac gcctagcaac    2880
accgccaaga tgctcatcaa ggctgaccag catcacctag acctcaccgc cctgcccacc    2940
ccagagtcca ccccgacact gcagcagaaa cggaaaccca accgcggcag tcgcgagtgg    3000
gagaggaacc agaacatcat caatgcctgc accaaggaca tgcctcccat gggttcccct    3060
gtgattccca cggacctgcc cctccgggcc tccccaagcc acatccccag cgtggtggtc    3120
ctgcccatca cgcagcaggg ctaccagcac gagtacgtag atcagcccaa aatgagcgag    3180
gtggtggctc agatggcact ggaggaccag gctgccaccc tggagtataa gaccatcaaa    3240
gagcacctga gtagcaagag tcccaaccat ggggtgaacc ttgtggagaa cctggacagc    3300 ctgccccta aagttccaca gcgcgaggcc tccctaggtc cccgggaac ctcactgtca    3360 cagaccggcc tgagcaagag gctggagatg caacactcct cctcctatgg gctcgaatat    3420
aagaggagct accccacgaa ctcgctcaca agaagccacc agaccaccac tctcaaaaga    3480
aacaatacta actcctccaa ttcctcccac ctctccagga accagagctt tggccgggga    3540
gacaacccac ccccgcccc gcagcgggtg gactctatcc aggtgcacag ctcccagccc    3600
tctggccagg ccgtgactgt ttcgaggcag cccagcctca atgcctacaa ctcactgacg    3660
aggtcggggc tgaagcgcac ccctcgcta aagccagatg tacccccaa accttccttt    3720 gctccctttt ccacatccat gaagcccaat gatgcatgta cataatccca ggggttgggg    3780
ggccaggagt tgaagcatcc gatgaggcga ggcacccacc cagctgagca aggtctccat    3840
tgcctcgagt atccacccga ccaagatggc cctggaggag ctgaggacgc tgggtcctcc    3900
tccctgggac atagggatac tcttcaaaat tgggccgtgt ggtctggtga aggtttagca    3960
atccacctct gcgttctctt ccttcacatc cacgtcatac agcaggtcgg actcacgaaa    4020
gacttcagta tcatcacaaa catgagccaa aagcacatct ccaccccatc ctcacatgaa    4080
cacaggccac agtcacattc gtgcactaca tacatataca cacacacaca cacacacaca    4140
cacaccatac cacaccacac cacaccacac cacaccacac cacaccacat cacaccacac    4200
cacacacgca atggtaaacg acaaccacat tttgtccctg actatacagg acgttaccaa    4260
acttggctaa gcatcagaaa ctttaaaaca cacacacaca cacaaccatt ttttttttaa    4320
aaaaaatcat gaaaattaaa aaaaataat aaaggattca ttgataattc taactcagac    4380
tttaacaatg gcagaagttt actatgcgca gatactgtga aatgcccacc agtgttacag    4440
ctttgttata gcaggtaaat gccatgttgg gcaacgatgt catagatttc tgctcctctt    4500
cgcttttaat gaataacgtg accgttaacg caagtaactc ttatttattg tccaccccctt    4560 ttcttttttcc tcaaggaaaa gactcttcca aatgccacca catgaacagc tctgcggaag    4620
cccgtggaaa gttaaactat ttaacgtgaa atccattaac tggaataatt gagtttcttt    4680
atttttacaa taaattcact gagtaaataa tttggagctg gaattctgag ctttgtgttt    4740
ggactatcgg atcagtagct aaaggacagt gctaggaagg aatatttatt taaatctagt    4800
taatttgtca gttgggtttc tcgccaagag gaaaaaaaaa tgtttaaaaa tccttccaga    4860
gtctaacttc cagccaggac agaaatgttt agaatggtgc ctaagcccca ttgccgtaaa    4920
catggctttg tctgaggacc ccaccatcag gaaggcatta gcttgtgaaa cctgccccta    4980
ccccctaccc ccgatccccg acccccacca tctcatttca ccttgcatgt gagacagcaa    5040
```

```
aacaaagatc cacaaactgt gtgaactaat taatatgctg gctgctacct tgcataaatt    5100
aatgatttga tcacacgggt gtttcatgag gttacatctg tgaatagcct gttttccaca    5160
tgtaaatttg tgccttacac tctgagttgt atacacttgt aaactgtcgt tatgatcaac    5220
tttcttttcc tacttgaaat aaaggcagat atttatttaa accctgccct ccattcagcc    5280
ctctggaaga ctggagacaa gcaaatggaa cagacacggt agcgatggtt gtaatgctga    5340
aggctgggtg ataccttca gttctccctg ccttcccttg tgccaacgcc agccaccctt    5400
tggccatgct gcagagcatg gacctccagt gttgtgggtg gaaaaaccc ctttccctta    5460 tattcccaga tcatttcaat ttggtgacat cttcctgagc cagccgagaa aggactgtgt    5520
tcactgactg gagaatcttg ctgcggtggt tagggaggca actgggaggc gtctccgagc    5580
tgtgccttca gcacacccag gcgatacaca gagaatcaac cagaaaatag accaggcagg    5640
ctggtccctg ctgtgattaa tgggtacccc aaagtacaaa ctaacgacaa tggatgctga    5700
aaaatccatt tctggggcaa aagtattttt ttgtttattt gtttctgttt ttttttttt    5760 aattctttta tctgtttgtt gtttgtagag ggttgggagg ggtagtgtgt ggttttgttt    5820
tttgcttttt ttgttttttcc cctcccttgg ttttcatttg ctaaagcaca cagaaggcac    5880
ctttgtttac tctatcatga acaaaagaat tgtctgcaca ctgtaatccg tgagcactgt    5940
ttccatataa acagtttatt tggtggtctc ttggtctctt ttcttttcc agtttgatct    6000 aggttttgtt ttgtctttaa aataaaacaa caataataat aataataaaa ctttcagaaa    6060 aaaaagatt ggcaagaaca aattcgaatt ggttatttaa aatttctatg ttgcacccgc    6120
cgtccgagca gtcctgcaga gcccacggtg tacagccgag aacaggtgta tagccctttg    6180

ttccaagact tgcctcggac cagctagact gttgtttgag atacataaga tatcactggt    6240

tttgttttgc tctttagagg agtcattgtt catggtctgt aaccattgca ccctgaagcc    6300
agaaaggctt ttctagaaac agatggtgtc ttctctattt ccttttcttc acaaatacaa    6360
aaatgaaaag gaaggtgcct gtcagccacc ccataccctc tcctcccttt tgactcccaa    6420
gagtattacc ccaacctcat gcccatgtta atgggcatca ttgcctcagt tgtgttacgg    6480
agacccatgt caaaacccac attcctacac cccacacccc gctcctttcg gtgtcccaca    6540

tgtattgagc tggtcttctg cttttccctg tccctctccc ттттcтgccст gaccttgcat    6600

tcgggggtag ggaggagatt gcccatgaac ctgagcgtgc cttcgctttc caccctggct    6660
agacagtgtc gatgcaacaa acgcagactt acattggttg taaagttgta aaatattgt    6720 gatgtcacca attttccttc cgtctccaca catcctaaca tctgattcac agtttaatgt    6780

atgtagttta aagaaaagg agagagagga tgaaaagaa aggggaaga gcggaaaat    6840 caagggatat ggctctatta cttaagagta ataaaatcag actgttctac gttaaaaaaa    6900
a                                                                   6901
```

<210> SEQ ID NO 10
<211> LENGTH: 1031
<212> TYPE: PRT
<213> ORGANISM: Mus musculus

<400> SEQUENCE: 10

Met Arg Pro Ala Ala Leu Leu Leu Cys Leu Thr Leu Leu His Cys Ala
1               5                   10                  15

Gly Ala Gly Phe Pro Glu Asp Ser Glu Pro Ile Ser Ile Ser His Gly
            20                  25                  30

-continued

Asn Tyr Thr Lys Gln Tyr Pro Val Phe Val Gly His Lys Pro Gly Arg
         35                  40                  45

Asn Thr Thr Gln Arg His Arg Leu Asp Ile Gln Met Ile Met Ile Met
 50                  55                  60

Asn Arg Thr Leu Tyr Val Ala Ala Arg Asp His Ile Tyr Thr Val Asp
 65                  70                  75                  80

Ile Asp Thr Ser His Thr Glu Glu Ile Tyr Cys Ser Lys Lys Leu Thr
                 85                  90                  95

Trp Lys Ser Arg Gln Ala Asp Val Asp Thr Cys Arg Met Lys Gly Lys
            100                 105                 110

His Lys Asp Glu Cys His Asn Phe Ile Lys Val Leu Leu Lys Lys Asn
        115                 120                 125

Asp Asp Thr Leu Phe Val Cys Gly Thr Asn Ala Phe Asn Pro Ser Cys
    130                 135                 140

Arg Asn Tyr Arg Val Asp Thr Leu Glu Thr Phe Gly Asp Glu Phe Ser
145                 150                 155                 160

Gly Met Ala Arg Cys Pro Tyr Asp Ala Lys His Ala Asn Ile Ala Leu
                165                 170                 175

Phe Ala Asp Gly Lys Leu Tyr Ser Ala Thr Val Thr Asp Phe Leu Ala
            180                 185                 190

Ile Asp Ala Val Ile Tyr Arg Ser Leu Gly Asp Ser Pro Thr Leu Arg
        195                 200                 205

Thr Val Lys His Asp Ser Lys Trp Leu Lys Glu Pro Tyr Phe Val Gln
    210                 215                 220

Ala Val Asp Tyr Gly Asp Tyr Ile Tyr Phe Phe Phe Arg Glu Ile Ala
225                 230                 235                 240

Val Glu Tyr Asn Thr Met Gly Lys Val Val Phe Pro Arg Val Ala Gln
                245                 250                 255

Val Cys Lys Asn Asp Met Gly Gly Ser Gln Arg Val Leu Glu Lys Gln
            260                 265                 270

Trp Thr Ser Phe Leu Lys Ala Arg Leu Asn Cys Ser Val Pro Gly Asp
        275                 280                 285

Ser His Phe Tyr Phe Asn Ile Leu Gln Ala Val Thr Asp Val Ile Arg
    290                 295                 300

Ile Asn Gly Arg Asp Val Val Leu Ala Thr Phe Ser Thr Pro Tyr Asn
305                 310                 315                 320

Ser Ile Pro Gly Ser Ala Val Cys Ala Tyr Asp Met Leu Asp Ile Ala
                325                 330                 335

Asn Val Phe Thr Gly Arg Phe Lys Glu Gln Lys Ser Pro Asp Ser Thr
            340                 345                 350

Trp Thr Pro Val Pro Asp Glu Arg Val Pro Lys Pro Arg Pro Gly Cys
        355                 360                 365

Cys Ala Gly Ser Ser Ser Leu Glu Lys Tyr Ala Thr Ser Asn Glu Phe
    370                 375                 380

Pro Asp Asp Thr Leu Asn Phe Ile Lys Thr His Pro Leu Met Asp Glu
385                 390                 395                 400

Ala Val Pro Ser Ile Ile Asn Arg Pro Trp Phe Leu Arg Thr Met Val
                405                 410                 415

Arg Tyr Arg Leu Thr Lys Ile Ala Val Asp Asn Ala Ala Gly Pro Tyr
            420                 425                 430

Gln Asn His Thr Val Val Phe Leu Gly Ser Glu Lys Gly Ile Ile Leu
        435                 440                 445

Lys Phe Leu Ala Arg Ile Gly Ser Ser Gly Phe Leu Asn Gly Ser Leu

```
            450                 455                 460
Phe Leu Glu Glu Met Asn Val Tyr Asn Pro Glu Lys Cys Ser Tyr Asp
465                 470                 475                 480

Gly Val Glu Asp Lys Arg Ile Met Gly Met Gln Leu Asp Arg Ala Ser
                485                 490                 495

Gly Ser Leu Tyr Val Ala Phe Ser Thr Cys Val Ile Lys Val Pro Leu
                500                 505                 510

Gly Arg Cys Glu Arg His Gly Lys Cys Lys Lys Thr Cys Ile Ala Ser
                515                 520                 525

Arg Asp Pro Tyr Cys Gly Trp Val Arg Glu Ser Gly Ser Cys Ala His
                530                 535                 540

Leu Ser Pro Leu Ser Arg Leu Thr Phe Glu Gln Asp Ile Glu Arg Gly
545                 550                 555                 560

Asn Thr Asp Gly Leu Gly Asp Cys His Asn Ser Phe Val Ala Leu Asn
                565                 570                 575

Gly His Ala Ser Ser Leu Tyr Pro Ser Thr Thr Ser Asp Ser Ala
                580                 585                 590

Ser Arg Asp Gly Tyr Glu Ser Arg Gly Gly Met Leu Asp Trp Asn Asp
                595                 600                 605

Leu Leu Glu Ala Pro Gly Ser Thr Asp Pro Leu Gly Ala Val Ser Ser
610                 615                 620

His Asn His Gln Asp Lys Lys Gly Val Ile Arg Glu Ser Tyr Leu Lys
625                 630                 635                 640

Ser Asn Asp Gln Leu Val Pro Val Thr Leu Leu Ala Ile Ala Val Ile
                645                 650                 655

Leu Ala Phe Val Met Gly Ala Val Phe Ser Gly Ile Ile Val Tyr Cys
                660                 665                 670

Val Cys Asp His Arg Arg Lys Asp Val Ala Val Gln Arg Lys Glu
                675                 680                 685

Lys Glu Leu Thr His Ser Arg Arg Gly Ser Met Ser Ser Val Thr Lys
                690                 695                 700

Leu Ser Gly Leu Phe Gly Asp Thr Gln Ser Lys Asp Pro Lys Pro Glu
705                 710                 715                 720

Ala Ile Leu Thr Pro Leu Met His Asn Gly Lys Leu Ala Thr Pro Ser
                725                 730                 735

Asn Thr Ala Lys Met Leu Ile Lys Ala Asp Gln His His Leu Asp Leu
                740                 745                 750

Thr Ala Leu Pro Thr Pro Glu Ser Thr Pro Thr Leu Gln Gln Lys Arg
                755                 760                 765

Lys Pro Asn Arg Gly Ser Arg Glu Trp Glu Arg Asn Gln Asn Ile Ile
                770                 775                 780

Asn Ala Cys Thr Lys Asp Met Pro Pro Met Gly Ser Pro Val Ile Pro
785                 790                 795                 800

Thr Asp Leu Pro Leu Arg Ala Ser Pro Ser His Ile Pro Ser Val Val
                805                 810                 815

Val Leu Pro Ile Thr Gln Gln Gly Tyr Gln His Glu Tyr Val Asp Gln
                820                 825                 830

Pro Lys Met Ser Glu Val Ala Gln Met Ala Leu Glu Asp Gln Ala
                835                 840                 845

Ala Thr Leu Glu Tyr Lys Thr Ile Lys Glu His Leu Ser Ser Lys Ser
                850                 855                 860

Pro Asn His Gly Val Asn Leu Val Glu Asn Leu Asp Ser Leu Pro Pro
865                 870                 875                 880
```

```
Lys Val Pro Gln Arg Glu Ala Ser Leu Gly Pro Pro Gly Thr Ser Leu
                885                 890                 895

Ser Gln Thr Gly Leu Ser Lys Arg Leu Glu Met Gln His Ser Ser Ser
            900                 905                 910

Tyr Gly Leu Glu Tyr Lys Arg Ser Tyr Pro Thr Asn Ser Leu Thr Arg
        915                 920                 925

Ser His Gln Thr Thr Thr Leu Lys Arg Asn Asn Thr Asn Ser Ser Asn
    930                 935                 940

Ser Ser His Leu Ser Arg Asn Gln Ser Phe Gly Arg Gly Asp Asn Pro
945                 950                 955                 960

Pro Pro Ala Pro Gln Arg Val Asp Ser Ile Gln Val His Ser Ser Gln
                965                 970                 975

Pro Ser Gly Gln Ala Val Thr Val Ser Arg Gln Pro Ser Leu Asn Ala
            980                 985                 990

Tyr Asn Ser Leu Thr Arg Ser Gly  Leu Lys Arg Thr Pro  Ser Leu Lys
        995                 1000                1005

Pro Asp  Val Pro Pro Lys Pro  Ser Phe Ala Pro Leu  Ser Thr Ser
   1010                1015                1020

Met Lys  Pro Asn Asp Ala Cys  Thr
   1025                1030

<210> SEQ ID NO 11
<211> LENGTH: 3018
<212> TYPE: DNA
<213> ORGANISM: Mus musculus

<400> SEQUENCE: 11
atgcggccag cagccttact gctgtgtctc acactgctac actgcgccgg ggcgggtttc      60
ccagaagatt ccgagccaat cagtatttcg catggcaact atacaaaaca gtatccggtg     120
tttgtgggcc acaagccagg acggaacacc acgcagaggc acaggctgga catccagatg     180
atcatgatca tgaacagaac cctctacgtt gctgctcgag accatattta tactgttgat     240
atagacacat cccacacaga agaaatttac tgtagcaaaa aactgacatg gaaatctaga     300
caggctgacg tagacacatg caggatgaag gggaaacata aggatgaatg tcacaacttc     360
attaaagttc ttctcaagaa gaatgatgat acgctgtttg tctgtggaac caatgccttc     420
aacccttcct gcagaaacta cagggtcgat accttgaaa cttttgggga tgaatttagc     480
ggaatggcca gatgccctta tgatgccaaa catgtcaaca tcgctctgtt tgcagatgga     540
aaactctact cggctacagt gactgacttt ctggccattg atgcggtcat ttacaggagc     600
cccggagaca gccctaccct caggactgtc aagcatgatt caaagtggtt gaaagagccg     660
tactttgtcc aagccgtgga ttatgggac tatatctact tcttcttcag agaaattgca     720
gtagaataca cactatggg aaaggttgtt ttccctaggg tggctcaggt ctgtaagaat     780
gacatgggag ggtctcagag agtcctggag aagcagtgga catctttcct gaaggctcgc     840
ctgaactgct cggtgcctgg agactctcat tttattttca atatactcca ggcagttaca     900
gatgtgattc gcattaatgg ccgtgatgtt gtcttggcaa cctttccac accttataac     960 agcatcccag ttctgcagt ctgtgcctat gacatgcttg acattgctga tgttttcact    1020
gggaggttca aggaacagaa atcacctgac tctacctgga cacccgttcc agacgaacga    1080
gtccctaagc ccaggccagg ctgttgtgct ggatcatcct ctttagaaaa atatgcaacc    1140
tccaatgagt ttcccgatga taccctgaac ttcattaaga cgcatccact catggacgag    1200
```

```
gcagtgcctt ccatcatcaa cagaccttgg ttcctgagaa caatggtcag ataccgcctg    1260
accaaaattg cagtagacaa cgctgccggg ccatatcaga atcacactgt ggttttcctg    1320
gaggagatga atgtttacaa cccagaaaag tgcagctatg atggtgtaga agacaaaagg    1380
atcatgggca tgcagctcga cagagcgagt ggctcactct atgttgcatt ctctacttgt    1440
gtgatcaagg tgcctcttgg ccgctgtgag cgacatggga agtgtaaaaa aacctgcatc    1500
gcctccagag acccgtattg tgggtgggta agggaaagtg gttcctgtgc ccatctgtca    1560
ccccttagca gactgacatt tgagcaggac attgagcgtg caatacggac cggcctagga    1620
gactgtcaca attccttcgt ggcactgaat gggcacgcca gttccctcta tcccaacacc    1680
actacgtcag attcggcatc ccgagacggg tatgagtcta ggggaggcat gctggactgg    1740
aacgacctgc tcgaggcacc tggcagcaca gaccctttgg gggcagtgtc ctctcataac    1800
caccaggaca agaagggagt gattcgggaa agttacctca aaagcaacga ccagcttgtt    1860
cctgtcaccc tcctggccat tgcagtcatt ctggcttttg tcatgggggc cgtcttctcg    1920
ggcatcatcg tgtattgtgt gtgcgatcac cggcgcaaag acgtggcagt agtgcggcgc    1980
aaggagaaag agctcactca ctcgcgtcgg ggatctatga gcagtgtctc cgagctcagt    2040
ggcctctttg gggacaccca gtccaaggac ccaaagcctg aggccatcct cacaccactc    2100
atgcacaacg gcaagctggc cacgtctagc aacaccgcca agatgctcat caaggctgac    2160
cagcatcacc tagacctcac cgccctgccc accccagagt ccaccccgac actgcagcag    2220
aaacggaaac ccaaccgcgg cagtcgcgag tgggagagga accagaacat catcaatgcc    2280
tgcaccaagg acatgcctcc catgggttcc cctgtgattc ccacggacct gccctccgg    2340 gcctccccaa gccacatccc cagcgtggtg gtcctgccca tcacgcagca gggctaccag    2400
cacgagtacg tagatcagcc caaaatgagc gaggtggtgg ctcagatggc actggaggac    2460
caggctgcca ccctggagta taagaccacc aaagagcacc tgagtagtaa gagtcccaac    2520
catggggtga accttgtgga aacctggac agcctgcccc ctaaagttcc acagcgcgag    2580
gcctccctag gtccccgggg aacctcactg tcacagaccg gctgagcaa gaggctggag    2640 atgcaacact cctcctccta tgggctcgaa tataagagga ctaccccac gaactcgctc    2700 acaagaagcc accagaccac cactctcaaa agaaacaata ctaactcctc caattcctcc    2760
cacctctcca ggaaccagag cttttggccg ggagacaacc cacccccgc cccgcagcgg    2820 gtggactcta tccaggtgca cagctcccag ccctctggcc aggccgtgac tgtttcgagg    2880
cagcccagcc tcaatgccta caactcactg acgaggtcgg ggctgaagcg cacccccctcg   2940 ctaaagcctg atgtaccccc caaaccttcc tttgctcccc tttccacatc catgaagccc    3000
aatgatgcgt gtacataa                                                  3018
```

<210> SEQ ID NO 12
<211> LENGTH: 1005
<212> TYPE: PRT
<213> ORGANISM: Mus musculus

<400> SEQUENCE: 12

```
Met Arg Pro Ala Ala Leu Leu Leu Cys Leu Thr Leu Leu His Cys Ala
1               5                   10                  15

Gly Ala Gly Phe Pro Glu Asp Ser Glu Pro Ile Ser Ile Ser His Gly
            20                  25                  30

Asn Tyr Thr Lys Gln Tyr Pro Val Phe Val Gly His Lys Pro Gly Arg
        35                  40                  45
```

```
Asn Thr Thr Gln Arg His Arg Leu Asp Ile Gln Met Ile Met Ile Met
    50                  55                  60

Asn Arg Thr Leu Tyr Val Ala Ala Arg Asp His Ile Tyr Thr Val Asp
65                  70                  75                  80

Ile Asp Thr Ser His Thr Glu Glu Ile Tyr Cys Ser Lys Lys Leu Thr
                85                  90                  95

Trp Lys Ser Arg Gln Ala Asp Val Asp Thr Cys Arg Met Lys Gly Lys
                100                 105                 110

His Lys Asp Glu Cys His Asn Phe Ile Lys Val Leu Leu Lys Lys Asn
            115                 120                 125

Asp Asp Thr Leu Phe Val Cys Gly Thr Asn Ala Phe Asn Pro Ser Cys
130                 135                 140

Arg Asn Tyr Arg Val Asp Thr Leu Glu Thr Phe Gly Asp Glu Phe Ser
145                 150                 155                 160

Gly Met Ala Arg Cys Pro Tyr Asp Ala Lys His Val Asn Ile Ala Leu
                165                 170                 175

Phe Ala Asp Gly Lys Leu Tyr Ser Ala Thr Val Thr Asp Phe Leu Ala
                180                 185                 190

Ile Asp Ala Val Ile Tyr Arg Ser Pro Gly Asp Ser Pro Thr Leu Arg
            195                 200                 205

Thr Val Lys His Asp Ser Lys Trp Leu Lys Glu Pro Tyr Phe Val Gln
        210                 215                 220

Ala Val Asp Tyr Gly Asp Tyr Ile Tyr Phe Phe Arg Glu Ile Ala
225                 230                 235                 240

Val Glu Tyr Asn Thr Met Gly Lys Val Val Phe Pro Arg Val Ala Gln
                245                 250                 255

Val Cys Lys Asn Asp Met Gly Gly Ser Gln Arg Val Leu Glu Lys Gln
            260                 265                 270

Trp Thr Ser Phe Leu Lys Ala Arg Leu Asn Cys Ser Val Pro Gly Asp
        275                 280                 285

Ser His Phe Tyr Phe Asn Ile Leu Gln Ala Val Thr Asp Val Ile Arg
    290                 295                 300

Ile Asn Gly Arg Asp Val Val Leu Ala Thr Phe Ser Thr Pro Tyr Asn
305                 310                 315                 320

Ser Ile Pro Gly Ser Ala Val Cys Ala Tyr Asp Met Leu Asp Ile Ala
                325                 330                 335

Asp Val Phe Thr Gly Arg Phe Lys Glu Gln Lys Ser Pro Asp Ser Thr
                340                 345                 350

Trp Thr Pro Val Pro Asp Glu Arg Val Pro Lys Pro Arg Pro Gly Cys
            355                 360                 365

Cys Ala Gly Ser Ser Ser Leu Glu Lys Tyr Ala Thr Ser Asn Glu Phe
        370                 375                 380

Pro Asp Asp Thr Leu Asn Phe Ile Lys Thr His Pro Leu Met Asp Glu
385                 390                 395                 400

Ala Val Pro Ser Ile Ile Asn Arg Pro Trp Phe Leu Arg Thr Met Val
                405                 410                 415

Arg Tyr Arg Leu Thr Lys Ile Ala Val Asp Asn Ala Ala Gly Pro Tyr
            420                 425                 430

Gln Asn His Thr Val Val Phe Leu Glu Glu Met Asn Val Tyr Asn Pro
        435                 440                 445

Glu Lys Cys Ser Tyr Asp Gly Val Glu Asp Lys Arg Ile Met Gly Met
450                 455                 460

Gln Leu Asp Arg Ala Ser Gly Ser Leu Tyr Val Ala Phe Ser Thr Cys
```

-continued

```
            465                 470                 475                 480
Val Ile Lys Val Pro Leu Gly Arg Cys Glu Arg His Gly Lys Cys Lys
                    485                 490                 495

Lys Thr Cys Ile Ala Ser Arg Asp Pro Tyr Cys Gly Trp Val Arg Glu
                500                 505                 510

Ser Gly Ser Cys Ala His Leu Ser Pro Leu Ser Arg Leu Thr Phe Glu
                515                 520                 525

Gln Asp Ile Glu Arg Gly Asn Thr Asp Gly Leu Gly Asp Cys His Asn
                530                 535                 540

Ser Phe Val Ala Leu Asn Gly His Ala Ser Ser Leu Tyr Pro Asn Thr
545                 550                 555                 560

Thr Thr Ser Asp Ser Ala Ser Arg Asp Gly Tyr Glu Ser Arg Gly Gly
                    565                 570                 575

Met Leu Asp Trp Asn Asp Leu Leu Glu Ala Pro Gly Ser Thr Asp Pro
                580                 585                 590

Leu Gly Ala Val Ser Ser His Asn His Gln Asp Lys Lys Gly Val Ile
                595                 600                 605

Arg Glu Ser Tyr Leu Lys Ser Asn Asp Gln Leu Val Pro Val Thr Leu
                610                 615                 620

Leu Ala Ile Ala Val Ile Leu Ala Phe Val Met Gly Ala Val Phe Ser
625                 630                 635                 640

Gly Ile Ile Val Tyr Cys Val Cys Asp His Arg Arg Lys Asp Val Ala
                    645                 650                 655

Val Val Arg Arg Lys Glu Lys Glu Leu Thr His Ser Arg Arg Gly Ser
                660                 665                 670

Met Ser Ser Val Ser Glu Leu Ser Gly Leu Phe Gly Asp Thr Gln Ser
                675                 680                 685

Lys Asp Pro Lys Pro Glu Ala Ile Leu Thr Pro Leu Met His Asn Gly
                690                 695                 700

Lys Leu Ala Thr Ser Ser Asn Thr Ala Lys Met Leu Ile Lys Ala Asp
705                 710                 715                 720

Gln His His Leu Asp Leu Thr Ala Leu Pro Thr Pro Glu Ser Thr Pro
                    725                 730                 735

Thr Leu Gln Gln Lys Arg Lys Pro Asn Arg Gly Ser Arg Glu Trp Glu
                740                 745                 750

Arg Asn Gln Asn Ile Ile Asn Ala Cys Thr Lys Asp Met Pro Pro Met
                755                 760                 765

Gly Ser Pro Val Ile Pro Thr Asp Leu Pro Leu Arg Ala Ser Pro Ser
                770                 775                 780

His Ile Pro Ser Val Val Leu Pro Ile Thr Gln Gln Gly Tyr Gln
785                 790                 795                 800

His Glu Tyr Val Asp Gln Pro Lys Met Ser Glu Val Val Ala Gln Met
                    805                 810                 815

Ala Leu Glu Asp Gln Ala Ala Thr Leu Glu Tyr Lys Thr Thr Lys Glu
                820                 825                 830

His Leu Ser Ser Lys Ser Pro Asn His Gly Val Asn Leu Val Glu Asn
                835                 840                 845

Leu Asp Ser Leu Pro Pro Lys Val Pro Gln Arg Glu Ala Ser Leu Gly
                850                 855                 860

Pro Pro Gly Thr Ser Leu Ser Gln Thr Gly Leu Ser Lys Arg Leu Glu
865                 870                 875                 880

Met Gln His Ser Ser Ser Tyr Gly Leu Glu Tyr Lys Arg Ser Tyr Pro
                    885                 890                 895
```

```
Thr Asn Ser Leu Thr Arg Ser His Gln Thr Thr Leu Lys Arg Asn
            900                 905                 910
Asn Thr Asn Ser Ser Asn Ser Ser His Leu Ser Arg Asn Gln Ser Phe
        915                 920                 925
Gly Arg Gly Asp Asn Pro Pro Ala Pro Gln Arg Val Asp Ser Ile
    930                 935                 940
Gln Val His Ser Ser Gln Pro Ser Gly Gln Ala Val Thr Val Ser Arg
945                 950                 955                 960
Gln Pro Ser Leu Asn Ala Tyr Asn Ser Leu Thr Arg Ser Gly Leu Lys
                965                 970                 975
Arg Thr Pro Ser Leu Lys Pro Asp Val Pro Pro Lys Pro Ser Phe Ala
            980                 985                 990
Pro Leu Ser Thr Ser Met Lys Pro  Asn Asp Ala Cys Thr
            995                 1000                1005
```

<210> SEQ ID NO 13
<211> LENGTH: 4139
<212> TYPE: DNA
<213> ORGANISM: Mus musculus

<400> SEQUENCE: 13

| | | | | | |
|---|---|---|---|---|---|
| acacagctcg | cttgcatccc | agaaagtaat | cgccgtgact | gttgccccca | aagagacaag | 60 |
| cacacatgta | ggaatgacaa | aggcttgcga | aggaaagagc | gcagctcaag | gcccagagag | 120 |
| atcttctcga | taatggatta | ctaaatggga | tactcgccgt | gtcagtccgc | tccgagccgc | 180 |
| ggccgcctgc | ccgtcgatgc | accgaaaagg | gtgaagtaga | gaagcaagtc | cccccgctga | 240 |
| acctactatg | cggccagcag | ccttactgct | gtgtctcaca | ctgctacact | gcgctggggc | 300 |
| tggtttccca | gaagattccg | agccaatcag | tatttcgcat | ggcaactata | caaaacagta | 360 |
| tccggtgttt | gtgggccaca | agccaggacg | gaacaccacg | cagaggcaca | ggctggacat | 420 |
| ccagatgatc | atgatcatga | acagaaccct | ctacgttgct | gctcgagacc | atatttatac | 480 |
| tgttgatata | gacacatccc | acacagaaga | aatttactgt | agcaaaaaac | tgacatggaa | 540 |
| atctagacag | gctgacgtag | acacatgcag | gatgaagggg | aaacataagg | atgaatgtca | 600 |
| caacttcatt | aaagttcttc | tcaagaagaa | tgatgatacg | ctgtttgtct | gtggaaccaa | 660 |
| tgccttcaac | cctcctgca | gaaactacag | ggtcgatacc | ttggaaactt | tggggatga | 720 |
| atttagcgga | atggccagat | gcccttatga | tgccaaacat | gccaacatcg | ctctgtttgc | 780 |
| agatggaaaa | ctctactcgg | ctacagtgac | tgactttctg | gccattgatg | cagtcatta | 840 |
| caggagcctc | ggagacagcc | ctaccctcag | gactgtcaag | catgattcaa | agtggttgaa | 900 |
| agagccgtac | tttgtccaag | ccgtggatta | tgggactat | atctacttct | tcttcagaga | 960 |
| aattgcagta | gaatacaaca | ctatggggaa | ggttgttttc | cctagggtgg | ctcaggtctg | 1020 |
| taagaatgac | atgggagggt | ctcagagagt | cctggagaag | cagtggacat | ctttcctgaa | 1080 |
| ggctcgcctg | aactgctcgg | tgcctggaga | ctctcatttt | tatttcaata | tactccaggc | 1140 |
| agttacagat | gtgattcgca | ttaatggccg | tgatgttgtc | ttggcaacct | tttccacacc | 1200 |
| ttataacagc | atcccaggtt | ctgcagtctg | tgcctatgac | atgcttgaca | ttgctaatgt | 1260 |
| tttcactggg | aggttcaagg | aacagaaatc | acctgactct | acctggacac | ccgttccaga | 1320 |
| cgaacgagtc | cctaagccca | ggccaggctg | ttgtgctgga | tcatcctctt | tagaaaaata | 1380 |
| tgcaacctcc | aatgagtttc | ccgatgatac | cctgaacttc | attaagacgc | atccactcat | 1440 |
| ggacgaggca | gtgccttcca | tcatcaacag | accttggtc | ctgagaacaa | tggtcagata | 1500 |

```
ccgcctgacc aaaattgcag tagacaacgc tgccgggcca tatcagaatc acactgtggt    1560
tttcctggga tcagaaaagg gaatcatcct gaagttcttg gccaggatag gaagcagtgg    1620
tttcctaaat ggcagccttt tcctggagga gatgaatgtt tacaacccag aaaagtgcag    1680
ctatgatggt gtagaagaca aaaggatcat gggcatgcag ctcgacagag cgagtggctc    1740
actctatgtt gcattctcta cttgtgtgat caaggtgcct cttggccgct gtgagcgaca    1800
tgggaagtgt aaaaaaacct gcatcgcctc cagagacccg tattgtgggt gggtaaggga    1860
aagtggttcc tgtgcccatc tgtcacccct tagcagactg acatttgagc aggacattga    1920
gcgtggcaat acgacggcc taggagactg tcacaattcc ttcgtggcac tgaatggagt    1980
gattcgggaa agttacctca aaagcaacga ccagcttgtt cctgtcaccc tcctggccat    2040
tgcagtcatt ctggcttttg tcatgggggc cgtcttctcg ggcatcatcg tgtattgtgt    2100
gtgcgatcac cggcgcaaag acgtggcagt agtgcagcgc aaggagaaag agctcactca    2160
ctcgcgtcgg ggatctatga gcagtgtcac caagctcagt ggcctctttg gggacaccca    2220
gtccaaggac ccaaagcctg aggccatcct cacaccactc atgcacaacg gcaagctggc    2280
cacgcctagc aacaccgcca agatgctcat caaggctgac cagcatcacc tagacctcac    2340
cgccctgccc accccagagt ccaccccgac actgcagcag aaacggaaac caaccgcgg    2400 cagtcgcgag tgggagagga accagaacat catcaatgcc tgcaccaagg acatgcctcc    2460
catgggttcc cctgtgattc ccacggacct gcccctccgg gcctcccaa gccacatccc    2520 cagcgtggtg gtcctgccca tcacgcagca gggctaccag cacgagtacg tagatcagcc    2580
caaaatgagc gaggtggtgg ctcagatggc actggaggac caggctgcca ccctggagta    2640
taagaccatc aaagagcacc tgagtagcaa gagtcccaac catggggtga accttgtgga    2700
gaacctggac agcctgcccc ctaaagttcc acagcgcgag gcctccctag gtccccggg    2760 aacctcactg tcacaaaccg gcctgagcaa gaggctggag atgcaacact cctcctccta    2820
tgggctcgaa tataagagga gctaccccac gaactcgctc acaagaagcc accagaccac    2880
cactctcaaa agaaacaata ctaactcctc caattcctcc cacctctcca ggaaccagag    2940 cttggccgg ggagacaacc cacccccgc cccgcagcgg gtggactcta tccaggtgca    3000
cagctcccag ccctctggcc aggccgtgac tgtttcgagg cagcccagcc tcaatgccta    3060
caactcactg acgaggtcgg ggctgaagcg caccccctcg ctaaagccag atgtaccccc    3120
caaaccttcc tttgctcccc tttccacatc catgaagccc aatgatgcat gtacataatc    3180
ccaggggttg gggggccagg agttgaagca tccgatgagg cgaggcaccc acccagctga    3240
gcaaggtctc cattgcctcg agtatccacc cgaccaagat ggccctggag gagctgagga    3300
cgctgggtcc cctcccctgg gacatagga tactcttcaa aattgggccg tgtggtctgg    3360
tgaaggttta gcaatccacc tctgcgttct cttccttcac atccacgtca tacagcaggt    3420
cggactcacg aaagacttca gtatcatcac aaacatgagc caaaagcaca tctccacccc    3480
atcctcacat gaacacaggc cacagtcaca ttcgtgcact acatacacat acacacacac    3540
acacacacac acacacacca taccacacca caccacacca caccacacca caccacacca    3600
catcacacca caccacacac gcaatggtaa acgacaacca cattttgtcc ctgactatac    3660
aggacgttac caaacttggc taagcatcag aaactttaaa acacacacac acacacaacc    3720 atttttttt ttaaaaaaaa tcatgaaaat taaaaaaaaa taataaagga ttcattgata    3780
attctaactc agactttaac aatggcagaa gtttactatg cgcagatact gtgaaatgcc    3840
```

```
caccagtgtt acagctttgt tatagcaggt aaatgccatg ttgggcaacg atgtcataga      3900
tttctgctcc tcttcgcttt taatgaataa cgtgaccgtt aacgcaagta actcttattt      3960
attgtccacc ccttttcttt ttcctcaagg aaaagactct tccaaatgcc accacatgaa      4020
cagctctgcg gaagcccgtg gaaagttaaa ctatttaacg tgaaatccat taactggaat      4080
aattgagttt ctttattttt acaataaatt cactgagtaa ataaaaaaaa aaaaaaaa        4139
```

<210> SEQ ID NO 14
<211> LENGTH: 976
<212> TYPE: PRT
<213> ORGANISM: Mus musculus

<400> SEQUENCE: 14

```
Met Arg Pro Ala Ala Leu Leu Leu Cys Leu Thr Leu His Cys Ala
1               5                   10                  15

Gly Ala Gly Phe Pro Glu Asp Ser Glu Pro Ile Ser Ile Ser His Gly
            20                  25                  30

Asn Tyr Thr Lys Gln Tyr Pro Val Phe Val Gly His Lys Pro Gly Arg
        35                  40                  45

Asn Thr Thr Gln Arg His Arg Leu Asp Ile Gln Met Ile Met Ile Met
    50                  55                  60

Asn Arg Thr Leu Tyr Val Ala Ala Arg Asp His Ile Tyr Thr Val Asp
65                  70                  75                  80

Ile Asp Thr Ser His Thr Glu Glu Ile Tyr Cys Ser Lys Lys Leu Thr
                85                  90                  95

Trp Lys Ser Arg Gln Ala Asp Val Asp Thr Cys Arg Met Lys Gly Lys
            100                 105                 110

His Lys Asp Glu Cys His Asn Phe Ile Lys Val Leu Leu Lys Lys Asn
        115                 120                 125

Asp Asp Thr Leu Phe Val Cys Gly Thr Asn Ala Phe Asn Pro Ser Cys
    130                 135                 140

Arg Asn Tyr Arg Val Asp Thr Leu Glu Thr Phe Gly Asp Glu Phe Ser
145                 150                 155                 160

Gly Met Ala Arg Cys Pro Tyr Asp Ala Lys His Ala Asn Ile Ala Leu
                165                 170                 175

Phe Ala Asp Gly Lys Leu Tyr Ser Ala Thr Val Thr Asp Phe Leu Ala
            180                 185                 190

Ile Asp Ala Val Ile Tyr Arg Ser Leu Gly Asp Ser Pro Thr Leu Arg
        195                 200                 205

Thr Val Lys His Asp Ser Lys Trp Leu Lys Glu Pro Tyr Phe Val Gln
    210                 215                 220

Ala Val Asp Tyr Gly Asp Tyr Ile Tyr Phe Phe Arg Glu Ile Ala
225                 230                 235                 240

Val Glu Tyr Asn Thr Met Gly Lys Val Val Phe Pro Arg Val Ala Gln
                245                 250                 255

Val Cys Lys Asn Asp Met Gly Gly Ser Gln Arg Val Leu Glu Lys Gln
            260                 265                 270

Trp Thr Ser Phe Leu Lys Ala Arg Leu Asn Cys Ser Val Pro Gly Asp
        275                 280                 285

Ser His Phe Tyr Phe Asn Ile Leu Gln Ala Val Thr Asp Val Ile Arg
    290                 295                 300

Ile Asn Gly Arg Asp Val Val Leu Ala Thr Phe Ser Thr Pro Tyr Asn
305                 310                 315                 320

Ser Ile Pro Gly Ser Ala Val Cys Ala Tyr Asp Met Leu Asp Ile Ala
```

```
                325                 330                 335
Asn Val Phe Thr Gly Arg Phe Lys Glu Gln Lys Ser Pro Asp Ser Thr
                340                 345                 350
Trp Thr Pro Val Pro Asp Glu Arg Val Pro Lys Pro Arg Pro Gly Cys
                355                 360                 365
Cys Ala Gly Ser Ser Ser Leu Glu Lys Tyr Ala Thr Ser Asn Glu Phe
                370                 375                 380
Pro Asp Asp Thr Leu Asn Phe Ile Lys Thr His Pro Leu Met Asp Glu
385                 390                 395                 400
Ala Val Pro Ser Ile Ile Asn Arg Pro Trp Phe Leu Arg Thr Met Val
                405                 410                 415
Arg Tyr Arg Leu Thr Lys Ile Ala Val Asp Asn Ala Ala Gly Pro Tyr
                420                 425                 430
Gln Asn His Thr Val Val Phe Leu Gly Ser Glu Lys Gly Ile Ile Leu
                435                 440                 445
Lys Phe Leu Ala Arg Ile Gly Ser Ser Gly Phe Leu Asn Gly Ser Leu
                450                 455                 460
Phe Leu Glu Glu Met Asn Val Tyr Asn Pro Glu Lys Cys Ser Tyr Asp
465                 470                 475                 480
Gly Val Glu Asp Lys Arg Ile Met Gly Met Gln Leu Asp Arg Ala Ser
                485                 490                 495
Gly Ser Leu Tyr Val Ala Phe Ser Thr Cys Val Ile Lys Val Pro Leu
                500                 505                 510
Gly Arg Cys Glu Arg His Gly Lys Cys Lys Lys Thr Cys Ile Ala Ser
                515                 520                 525
Arg Asp Pro Tyr Cys Gly Trp Val Arg Glu Ser Gly Ser Cys Ala His
                530                 535                 540
Leu Ser Pro Leu Ser Arg Leu Thr Phe Glu Gln Asp Ile Glu Arg Gly
545                 550                 555                 560
Asn Thr Asp Gly Leu Gly Asp Cys His Asn Ser Phe Val Ala Leu Asn
                565                 570                 575
Gly Val Ile Arg Glu Ser Tyr Leu Lys Ser Asn Asp Gln Leu Val Pro
                580                 585                 590
Val Thr Leu Leu Ala Ile Ala Val Ile Leu Ala Phe Val Met Gly Ala
                595                 600                 605
Val Phe Ser Gly Ile Ile Val Tyr Cys Val Cys Asp His Arg Arg Lys
                610                 615                 620
Asp Val Ala Val Val Gln Arg Lys Glu Lys Glu Leu Thr His Ser Arg
625                 630                 635                 640
Arg Gly Ser Met Ser Ser Val Thr Lys Leu Ser Gly Leu Phe Gly Asp
                645                 650                 655
Thr Gln Ser Lys Asp Pro Lys Pro Glu Ala Ile Leu Thr Pro Leu Met
                660                 665                 670
His Asn Gly Lys Leu Ala Thr Pro Ser Asn Thr Ala Lys Met Leu Ile
                675                 680                 685
Lys Ala Asp Gln His His Leu Asp Leu Thr Ala Leu Pro Thr Pro Glu
                690                 695                 700
Ser Thr Pro Thr Leu Gln Gln Lys Arg Lys Pro Asn Arg Gly Ser Arg
705                 710                 715                 720
Glu Trp Glu Arg Asn Gln Asn Ile Ile Asn Ala Cys Thr Lys Asp Met
                725                 730                 735
Pro Pro Met Gly Ser Pro Val Ile Pro Thr Asp Leu Pro Leu Arg Ala
                740                 745                 750
```

```
Ser Pro Ser His Ile Pro Ser Val Val Leu Pro Ile Thr Gln Gln
        755                 760                 765

Gly Tyr Gln His Glu Tyr Val Asp Gln Pro Lys Met Ser Glu Val Val
    770                 775                 780

Ala Gln Met Ala Leu Glu Asp Gln Ala Ala Thr Leu Glu Tyr Lys Thr
785                 790                 795                 800

Ile Lys Glu His Leu Ser Ser Lys Ser Pro Asn His Gly Val Asn Leu
                805                 810                 815

Val Glu Asn Leu Asp Ser Leu Pro Pro Lys Val Pro Gln Arg Glu Ala
            820                 825                 830

Ser Leu Gly Pro Pro Gly Thr Ser Leu Ser Gln Thr Gly Leu Ser Lys
        835                 840                 845

Arg Leu Glu Met Gln His Ser Ser Ser Tyr Gly Leu Glu Tyr Lys Arg
    850                 855                 860

Ser Tyr Pro Thr Asn Ser Leu Thr Arg Ser His Gln Thr Thr Thr Leu
865                 870                 875                 880

Lys Arg Asn Asn Thr Asn Ser Ser Asn Ser Ser His Leu Ser Arg Asn
                885                 890                 895

Gln Ser Phe Gly Arg Gly Asp Asn Pro Pro Ala Pro Gln Arg Val
            900                 905                 910

Asp Ser Ile Gln Val His Ser Ser Gln Pro Ser Gly Gln Ala Val Thr
    915                 920                 925

Val Ser Arg Gln Pro Ser Leu Asn Ala Tyr Asn Ser Leu Thr Arg Ser
930                 935                 940

Gly Leu Lys Arg Thr Pro Ser Leu Lys Pro Asp Val Pro Pro Lys Pro
945                 950                 955                 960

Ser Phe Ala Pro Leu Ser Thr Ser Met Lys Pro Asn Asp Ala Cys Thr
                965                 970                 975

<210> SEQ ID NO 15
<211> LENGTH: 1909
<212> TYPE: PRT
<213> ORGANISM: Homo sapiens

<400> SEQUENCE: 15

Met Ser Thr His Arg Ser Arg Leu Leu Thr Ala Ala Pro Leu Ser Met
1               5                   10                  15

Glu Gln Arg Arg Pro Trp Pro Arg Ala Leu Glu Val Asp Ser Arg Ser
            20                  25                  30

Val Val Leu Leu Ser Val Val Trp Val Leu Leu Ala Pro Pro Ala Ala
        35                  40                  45

Gly Met Pro Gln Phe Ser Thr Phe His Ser Glu Asn Arg Asp Trp Thr
    50                  55                  60

Phe Asn His Leu Thr Val His Gln Gly Thr Gly Ala Val Tyr Val Gly
65                  70                  75                  80

Ala Ile Asn Arg Val Tyr Lys Leu Thr Gly Asn Leu Thr Ile Gln Val
                85                  90                  95

Ala His Lys Thr Gly Pro Glu Glu Asp Asn Lys Ser Cys Tyr Pro Pro
            100                 105                 110

Leu Ile Val Gln Pro Cys Ser Glu Val Leu Thr Leu Thr Asn Asn Val
        115                 120                 125

Asn Lys Leu Leu Ile Ile Asp Tyr Ser Glu Asn Arg Leu Leu Ala Cys
    130                 135                 140

Gly Ser Leu Tyr Gln Gly Val Cys Lys Leu Leu Arg Leu Asp Asp Leu
```

-continued

```
        145                 150                 155                 160
        Phe Ile Leu Val Glu Pro Ser His Lys Lys Glu His Tyr Leu Ser Ser
                        165                 170                 175

Val Asn Lys Thr Gly Thr Met Tyr Gly Val Ile Val Arg Ser Glu Gly
                        180                 185                 190

Glu Asp Gly Lys Leu Phe Ile Gly Thr Ala Val Asp Gly Lys Gln Asp
                        195                 200                 205

Tyr Phe Pro Thr Leu Ser Ser Arg Lys Leu Pro Arg Asp Pro Glu Ser
                        210                 215                 220

Ser Ala Met Leu Asp Tyr Glu Leu His Ser Asp Phe Val Ser Ser Leu
        225                 230                 235                 240

Ile Lys Ile Pro Ser Asp Thr Leu Ala Leu Val Ser His Phe Asp Ile
                        245                 250                 255

Phe Tyr Ile Tyr Gly Phe Ala Ser Gly Gly Phe Val Tyr Phe Leu Thr
                        260                 265                 270

Val Gln Pro Glu Thr Pro Glu Gly Val Ala Ile Asn Ser Ala Gly Asp
                        275                 280                 285

Leu Phe Tyr Thr Ser Arg Ile Val Arg Leu Cys Lys Asp Asp Pro Lys
                        290                 295                 300

Phe His Ser Tyr Val Ser Leu Pro Phe Gly Cys Thr Arg Ala Gly Val
        305                 310                 315                 320

Glu Tyr Arg Leu Leu Gln Ala Ala Tyr Leu Ala Lys Pro Gly Asp Ser
                        325                 330                 335

Leu Ala Gln Ala Phe Asn Ile Thr Ser Gln Asp Asp Val Leu Phe Ala
                        340                 345                 350

Ile Phe Ser Lys Gly Gln Lys Gln Tyr His His Pro Pro Asp Asp Ser
                        355                 360                 365

Ala Leu Cys Ala Phe Pro Ile Arg Ala Ile Asn Leu Gln Ile Lys Gly
                        370                 375                 380

Arg Leu Gln Ser Cys Tyr Gln Gly Glu Gly Asn Leu Glu Leu Asn Trp
        385                 390                 395                 400

Leu Leu Gly Lys Asp Val Gln Cys Thr Lys Ala Pro Val Pro Ile Asp
                        405                 410                 415

Asp Asn Phe Cys Gly Leu Asp Ile Asn Gln Pro Leu Gly Gly Ser Thr
                        420                 425                 430

Pro Val Glu Gly Leu Thr Leu Tyr Thr Thr Ser Arg Asp Arg Met Thr
                        435                 440                 445

Ser Val Ala Ser Tyr Val Tyr Asn Gly Tyr Ser Val Val Phe Val Gly
        450                 455                 460

Thr Lys Ser Gly Lys Leu Lys Lys Ile Arg Ala Asp Gly Pro Pro His
        465                 470                 475                 480

Gly Gly Val Gln Tyr Glu Met Val Ser Val Leu Lys Asp Gly Ser Pro
                        485                 490                 495

Ile Leu Arg Asp Met Ala Phe Ser Ile Asp Gln Arg Tyr Leu Tyr Val
                        500                 505                 510

Met Ser Glu Arg Gln Val Thr Arg Val Pro Val Glu Ser Cys Glu Gln
                        515                 520                 525

Tyr Thr Thr Cys Gly Glu Cys Leu Ser Ser Gly Asp Pro His Cys Gly
                        530                 535                 540

Trp Cys Ala Leu His Asn Met Cys Ser Arg Arg Asp Lys Cys Gln Gln
        545                 550                 555                 560

Ala Trp Glu Pro Asn Arg Phe Ala Ala Ser Ile Ser Gln Cys Val Ser
                        565                 570                 575
```

```
Leu Ala Val His Pro Ser Ser Ile Ser Val Ser Glu His Ser Arg Leu
            580                 585                 590

Leu Ser Leu Val Val Ser Asp Ala Pro Asp Leu Ser Ala Gly Ile Ala
        595                 600                 605

Cys Ala Phe Gly Asn Leu Thr Glu Val Glu Gly Gln Val Ser Gly Ser
    610                 615                 620

Gln Val Ile Cys Ile Ser Pro Gly Pro Lys Asp Val Pro Val Ile Pro
625                 630                 635                 640

Leu Asp Gln Asp Trp Phe Gly Leu Glu Leu Gln Leu Arg Ser Lys Glu
                645                 650                 655

Thr Gly Lys Ile Phe Val Ser Thr Glu Phe Lys Phe Tyr Asn Cys Ser
            660                 665                 670

Ala His Gln Leu Cys Leu Ser Cys Val Asn Ser Ala Phe Arg Cys His
        675                 680                 685

Trp Cys Lys Tyr Arg Asn Leu Cys Thr His Asp Pro Thr Thr Cys Ser
    690                 695                 700

Phe Gln Glu Gly Arg Ile Asn Ile Ser Glu Asp Cys Pro Gln Leu Val
705                 710                 715                 720

Pro Thr Glu Glu Ile Leu Ile Pro Val Gly Glu Val Lys Pro Ile Thr
                725                 730                 735

Leu Lys Ala Arg Asn Leu Pro Gln Pro Gln Ser Gly Gln Arg Gly Tyr
            740                 745                 750

Glu Cys Val Leu Asn Ile Gln Gly Ala Ile His Arg Val Pro Ala Leu
        755                 760                 765

Arg Phe Asn Ser Ser Val Gln Cys Gln Asn Ser Ser Tyr Gln Tyr
    770                 775                 780

Asp Gly Met Asp Ile Ser Asn Leu Ala Val Asp Phe Ala Val Val Trp
785                 790                 795                 800

Asn Gly Asn Phe Ile Ile Asp Asn Pro Gln Asp Leu Lys Val His Leu
                805                 810                 815

Tyr Lys Cys Ala Ala Gln Arg Glu Ser Cys Gly Leu Cys Leu Lys Ala
            820                 825                 830

Asp Arg Lys Phe Glu Cys Gly Trp Cys Ser Gly Glu Arg Arg Cys Thr
        835                 840                 845

Leu His Gln His Cys Thr Ser Pro Ser Ser Pro Trp Leu Asp Trp Ser
    850                 855                 860

Ser His Asn Val Lys Cys Ser Asn Pro Gln Ile Thr Glu Ile Leu Thr
865                 870                 875                 880

Val Ser Gly Pro Pro Glu Gly Gly Thr Arg Val Thr Ile His Gly Val
                885                 890                 895

Asn Leu Gly Leu Asp Phe Ser Glu Ile Ala His His Val Gln Val Ala
            900                 905                 910

Gly Val Pro Cys Thr Pro Leu Pro Gly Glu Tyr Ile Ile Ala Glu Gln
        915                 920                 925

Ile Val Cys Glu Met Gly His Ala Leu Val Gly Thr Thr Ser Gly Pro
    930                 935                 940

Val Arg Leu Cys Ile Gly Glu Cys Lys Pro Glu Phe Met Thr Lys Ser
945                 950                 955                 960

His Gln Gln Tyr Thr Phe Val Asn Pro Ser Val Leu Ser Leu Asn Pro
                965                 970                 975

Ile Arg Gly Pro Glu Ser Gly Gly Thr Met Val Thr Ile Thr Gly His
            980                 985                 990
```

```
Tyr Leu Gly Ala Gly Ser Ser Val  Ala Val Tyr Leu Gly  Asn Gln Thr
            995              1000                1005

Cys Glu  Phe Tyr Gly Arg Ser  Met Ser Glu Ile Val  Cys Val Ser
    1010             1015                 1020

Pro Pro  Ser Ser Asn Gly Leu  Gly Pro Val Pro Val  Ser Val Ser
    1025             1030                 1035

Val Asp  Arg Ala His Val Asp  Ser Asn Leu Gln Phe  Glu Tyr Ile
    1040             1045                 1050

Asp Asp  Pro Arg Val Gln Arg  Ile Glu Pro Glu Trp  Ser Ile Ala
    1055             1060                 1065

Ser Gly  His Thr Pro Leu Thr  Ile Thr Gly Phe Asn  Leu Asp Val
    1070             1075                 1080

Ile Gln  Glu Pro Arg Ile Arg  Val Lys Phe Asn Gly  Lys Glu Ser
    1085             1090                 1095

Val Asn  Val Cys Lys Val Val  Asn Thr Thr Leu Thr  Cys Leu
    1100             1105                 1110

Ala Pro  Ser Leu Thr Thr Asp  Tyr Arg Pro Gly Leu  Asp Thr Val
    1115             1120                 1125

Glu Arg  Pro Asp Glu Phe Gly  Phe Val Phe Asn Asn  Val Gln Ser
    1130             1135                 1140

Leu Leu  Ile Tyr Asn Asp Thr  Lys Phe Ile Tyr Tyr  Pro Asn Pro
    1145             1150                 1155

Thr Phe  Glu Leu Leu Ser Pro  Thr Gly Val Leu Asp  Gln Lys Pro
    1160             1165                 1170

Gly Ser  Pro Ile Ile Leu Lys  Gly Lys Asn Leu Cys  Pro Pro Ala
    1175             1180                 1185

Ser Gly  Gly Ala Lys Leu Asn  Tyr Thr Val Leu Ile  Gly Glu Thr
    1190             1195                 1200

Pro Cys  Ala Val Thr Val Ser  Glu Thr Gln Leu Leu  Cys Glu Pro
    1205             1210                 1215

Pro Asn  Leu Thr Gly Gln His  Lys Val Met Val His  Val Gly Gly
    1220             1225                 1230

Met Val  Phe Ser Pro Gly Ser  Val Ser Val Ile Ser  Asp Ser Leu
    1235             1240                 1245

Leu Thr  Leu Pro Ala Ile Val  Ser Ile Ala Ala Gly  Gly Ser Leu
    1250             1255                 1260

Leu Leu  Ile Ile Val Ile Ile  Val Leu Ile Ala Tyr  Lys Arg Lys
    1265             1270                 1275

Ser Arg  Glu Asn Asp Leu Thr  Leu Lys Arg Leu Gln  Met Gln Met
    1280             1285                 1290

Asp Asn  Leu Glu Ser Arg Val  Ala Leu Glu Cys Lys  Glu Ala Phe
    1295             1300                 1305

Ala Glu  Leu Gln Thr Asp Ile  Asn Glu Leu Thr Ser  Asp Leu Asp
    1310             1315                 1320

Arg Ser  Gly Ile Pro Tyr Leu  Asp Tyr Arg Thr Tyr  Ala Met Arg
    1325             1330                 1335

Val Leu  Phe Pro Gly Ile Glu  Asp His Pro Val Leu  Arg Glu Leu
    1340             1345                 1350

Glu Val  Gln Gly Asn Gly Gln  Gln His Val Glu Lys  Ala Leu Lys
    1355             1360                 1365

Leu Phe  Ala Gln Leu Ile Asn  Asn Lys Val Phe Leu  Leu Thr Phe
    1370             1375                 1380

Ile Arg  Thr Leu Glu Leu Gln  Arg Ser Phe Ser Met  Arg Asp Arg
```

-continued

```
            1385                1390                1395

Gly Asn Val Ala Ser Leu Ile Met Thr Gly Leu Gln Gly Arg Leu
            1400                1405                1410

Glu Tyr Ala Thr Asp Val Leu Lys Gln Leu Leu Ser Asp Leu Ile
            1415                1420                1425

Asp Lys Asn Leu Glu Asn Lys Asn His Pro Lys Leu Leu Leu Arg
            1430                1435                1440

Arg Thr Glu Ser Val Ala Glu Lys Met Leu Thr Asn Trp Phe Ala
            1445                1450                1455

Phe Leu Leu His Lys Phe Leu Lys Glu Cys Ala Gly Glu Pro Leu
            1460                1465                1470

Phe Met Leu Tyr Cys Ala Ile Lys Gln Gln Met Glu Lys Gly Pro
            1475                1480                1485

Ile Asp Ala Ile Thr Gly Glu Ala Arg Tyr Ser Leu Ser Glu Asp
            1490                1495                1500

Lys Leu Ile Arg Gln Gln Ile Glu Tyr Lys Thr Leu Ile Leu Asn
            1505                1510                1515

Cys Val Asn Pro Asp Asn Glu Asn Ser Pro Glu Ile Pro Val Lys
            1520                1525                1530

Val Leu Asn Cys Asp Thr Ile Thr Gln Val Lys Glu Lys Ile Leu
            1535                1540                1545

Asp Ala Val Tyr Lys Asn Val Pro Tyr Ser Gln Arg Pro Arg Ala
            1550                1555                1560

Val Asp Met Asp Leu Glu Trp Arg Gln Gly Arg Ile Ala Arg Val
            1565                1570                1575

Val Leu Gln Asp Glu Asp Ile Thr Thr Lys Ile Glu Gly Asp Trp
            1580                1585                1590

Lys Arg Leu Asn Thr Leu Met His Tyr Gln Val Ser Asp Arg Ser
            1595                1600                1605

Val Val Ala Leu Val Pro Lys Gln Thr Ser Ser Tyr Asn Ile Pro
            1610                1615                1620

Ala Ser Ala Ser Ile Ser Arg Thr Ser Ile Ser Arg Tyr Asp Ser
            1625                1630                1635

Ser Phe Arg Tyr Thr Gly Ser Pro Asp Ser Leu Arg Ser Arg Ala
            1640                1645                1650

Pro Met Ile Thr Pro Asp Leu Glu Ser Gly Val Lys Val Trp His
            1655                1660                1665

Leu Val Lys Asn His Asp His Gly Asp Gln Lys Glu Gly Asp Arg
            1670                1675                1680

Gly Ser Lys Met Val Ser Glu Ile Tyr Leu Thr Arg Leu Leu Ala
            1685                1690                1695

Thr Lys Gly Thr Leu Gln Lys Phe Val Asp Asp Leu Phe Glu Thr
            1700                1705                1710

Leu Phe Ser Thr Val His Arg Gly Ser Ala Leu Pro Leu Ala Ile
            1715                1720                1725

Lys Tyr Met Phe Asp Phe Leu Asp Glu Gln Ala Asp Arg His Ser
            1730                1735                1740

Ile His Asp Thr Asp Val Arg His Thr Trp Lys Ser Asn Cys Leu
            1745                1750                1755

Pro Leu Arg Phe Trp Val Asn Val Ile Lys Asn Pro Gln Phe Val
            1760                1765                1770

Phe Asp Ile His Lys Gly Ser Ile Thr Asp Ala Cys Leu Ser Val
            1775                1780                1785
```

Val Ala Gln Thr Phe Met Asp Ser Cys Ser Thr Ser Glu His Arg
    1790                1795                1800

Leu Gly Lys Asp Ser Pro Ser Asn Lys Leu Leu Tyr Ala Lys Asp
    1805                1810                1815

Ile Pro Ser Tyr Lys Ser Trp Val Glu Arg Tyr Tyr Ala Asp Ile
    1820                1825                1830

Ala Lys Leu Pro Ala Ile Ser Asp Gln Asp Met Asn Ala Tyr Leu
    1835                1840                1845

Ala Glu Gln Ser Arg Leu His Ala Val Glu Phe Asn Met Leu Ser
    1850                1855                1860

Ala Leu Asn Glu Ile Tyr Ser Tyr Val Ser Lys Tyr Ser Glu Glu
    1865                1870                1875

Leu Ile Gly Ala Leu Glu Gln Asp Glu Gln Ala Arg Arg Gln Arg
    1880                1885                1890

Leu Ala Tyr Lys Val Glu Gln Leu Ile Asn Ala Met Ser Ile Glu
    1895                1900                1905

Ser

<210> SEQ ID NO 16
<211> LENGTH: 1894
<212> TYPE: PRT
<213> ORGANISM: Homo sapiens

<400> SEQUENCE: 16

Met Lys Ala Met Pro Trp Asn Trp Thr Cys Leu Leu Ser His Leu Leu
1               5                   10                  15

Met Val Gly Met Gly Ser Ser Thr Leu Leu Thr Arg Gln Pro Ala Pro
                20                  25                  30

Leu Ser Gln Lys Gln Arg Ser Phe Val Thr Phe Arg Gly Glu Pro Ala
            35                  40                  45

Glu Gly Phe Asn His Leu Val Val Asp Glu Arg Thr Gly His Ile Tyr
        50                  55                  60

Leu Gly Ala Val Asn Arg Ile Tyr Lys Leu Ser Ser Asp Leu Lys Val
65                  70                  75                  80

Leu Val Thr His Glu Thr Gly Pro Asp Glu Asp Asn Pro Lys Cys Tyr
                85                  90                  95

Pro Pro Arg Ile Val Gln Thr Cys Asn Glu Pro Leu Thr Thr Thr Asn
            100                 105                 110

Asn Val Asn Lys Met Leu Leu Ile Asp Tyr Lys Glu Asn Arg Leu Ile
        115                 120                 125

Ala Cys Gly Ser Leu Tyr Gln Gly Ile Cys Lys Leu Leu Arg Leu Glu
    130                 135                 140

Asp Leu Phe Lys Leu Gly Glu Pro Tyr His Lys Lys Glu His Tyr Leu
145                 150                 155                 160

Ser Gly Val Asn Glu Ser Gly Ser Val Phe Gly Val Ile Val Ser Tyr
                165                 170                 175

Ser Asn Leu Asp Asp Lys Leu Phe Ile Ala Thr Ala Val Asp Gly Lys
            180                 185                 190

Pro Glu Tyr Phe Pro Thr Ile Ser Ser Arg Lys Leu Thr Lys Asn Ser
        195                 200                 205

Glu Ala Asp Gly Met Phe Ala Tyr Val Phe His Asp Glu Phe Val Ala
    210                 215                 220

Ser Met Ile Lys Ile Pro Ser Asp Thr Phe Thr Ile Ile Pro Asp Phe
225                 230                 235                 240

-continued

```
Asp Ile Tyr Tyr Val Tyr Gly Phe Ser Ser Asn Phe Val Tyr Phe
                245                 250                 255

Leu Thr Leu Gln Pro Glu Met Val Ser Pro Pro Gly Ser Thr Thr Lys
        260                 265                 270

Glu Gln Val Tyr Thr Ser Lys Leu Val Arg Leu Cys Lys Glu Asp Thr
            275                 280                 285

Ala Phe Asn Ser Tyr Val Glu Val Pro Ile Gly Cys Glu Arg Ser Gly
        290                 295                 300

Val Glu Tyr Arg Leu Leu Gln Ala Ala Tyr Leu Ser Lys Ala Gly Ala
305                 310                 315                 320

Val Leu Gly Arg Thr Leu Gly Val His Pro Asp Asp Leu Leu Phe
                325                 330                 335

Thr Val Phe Ser Lys Gly Gln Lys Arg Lys Met Lys Ser Leu Asp Glu
                340                 345                 350

Ser Ala Leu Cys Ile Phe Ile Leu Lys Gln Ile Asn Asp Arg Ile Lys
            355                 360                 365

Glu Arg Leu Gln Ser Cys Tyr Arg Gly Glu Gly Thr Leu Asp Leu Ala
        370                 375                 380

Trp Leu Lys Val Lys Asp Ile Pro Cys Ser Ser Ala Leu Leu Thr Ile
385                 390                 395                 400

Asp Asp Asn Phe Cys Gly Leu Asp Met Asn Ala Pro Leu Gly Val Ser
                405                 410                 415

Asp Met Val Arg Gly Ile Pro Val Phe Thr Glu Asp Arg Asp Arg Met
                420                 425                 430

Thr Ser Val Ile Ala Tyr Val Tyr Lys Asn His Ser Leu Ala Phe Val
            435                 440                 445

Gly Thr Lys Ser Gly Lys Leu Lys Lys Ile Arg Val Asp Gly Pro Arg
        450                 455                 460

Gly Asn Ala Leu Gln Tyr Glu Thr Val Gln Val Val Asp Pro Gly Pro
465                 470                 475                 480

Val Leu Arg Asp Met Ala Phe Ser Lys Asp His Glu Gln Leu Tyr Ile
                485                 490                 495

Met Ser Glu Arg Gln Leu Thr Arg Val Pro Val Glu Ser Cys Gly Gln
                500                 505                 510

Tyr Gln Ser Cys Gly Glu Cys Leu Gly Ser Gly Asp Pro His Cys Gly
            515                 520                 525

Trp Cys Val Leu His Asn Thr Cys Thr Arg Lys Glu Arg Cys Glu Arg
        530                 535                 540

Ser Lys Glu Pro Arg Arg Phe Ala Ser Glu Met Lys Gln Cys Val Arg
545                 550                 555                 560

Leu Thr Val His Pro Asn Asn Ile Ser Val Ser Gln Tyr Asn Val Leu
                565                 570                 575

Leu Val Leu Glu Thr Tyr Asn Val Pro Glu Leu Ser Ala Gly Val Asn
                580                 585                 590

Cys Thr Phe Glu Asp Leu Ser Glu Met Asp Gly Leu Val Gly Asn
            595                 600                 605

Gln Ile Gln Cys Tyr Ser Pro Ala Ala Lys Glu Val Pro Arg Ile Ile
        610                 615                 620

Thr Glu Asn Gly Asp His His Val Val Gln Leu Gln Leu Lys Ser Lys
625                 630                 635                 640

Glu Thr Gly Met Thr Phe Ala Ser Thr Ser Phe Val Phe Tyr Asn Cys
                645                 650                 655
```

```
Ser Val His Asn Ser Cys Leu Ser Cys Val Glu Ser Pro Tyr Arg Cys
        660                 665                 670

His Trp Cys Lys Tyr Arg His Val Cys Thr His Asp Pro Lys Thr Cys
    675                 680                 685

Ser Phe Gln Glu Gly Arg Val Lys Leu Pro Glu Asp Cys Pro Gln Leu
690                 695                 700

Leu Arg Val Asp Lys Ile Leu Val Pro Val Glu Val Ile Lys Pro Ile
705                 710                 715                 720

Thr Leu Lys Ala Lys Asn Leu Pro Gln Pro Gln Ser Gly Gln Arg Gly
                725                 730                 735

Tyr Glu Cys Ile Leu Asn Ile Gln Gly Ser Glu Gln Arg Val Pro Ala
                740                 745                 750

Leu Arg Phe Asn Ser Ser Val Gln Cys Gln Asn Thr Ser Tyr Ser
            755                 760                 765

Tyr Glu Gly Met Glu Ile Asn Asn Leu Pro Val Glu Leu Thr Val Val
            770                 775                 780

Trp Asn Gly His Phe Asn Ile Asp Asn Pro Ala Gln Asn Lys Val His
785                 790                 795                 800

Leu Tyr Lys Cys Gly Ala Met Arg Glu Ser Cys Gly Leu Cys Leu Lys
                805                 810                 815

Ala Asp Pro Asp Phe Ala Cys Gly Trp Cys Gln Gly Pro Gly Gln Cys
            820                 825                 830

Thr Leu Arg Gln His Cys Pro Ala Gln Glu Ser Gln Trp Leu Glu Leu
        835                 840                 845

Ser Gly Ala Lys Ser Lys Cys Thr Asn Pro Arg Ile Thr Glu Ile Ile
850                 855                 860

Pro Val Thr Gly Pro Arg Glu Gly Gly Thr Lys Val Thr Ile Arg Gly
865                 870                 875                 880

Glu Asn Leu Gly Leu Glu Phe Arg Asp Ile Ala Ser His Val Lys Val
                885                 890                 895

Ala Gly Val Glu Cys Ser Pro Leu Val Asp Gly Tyr Ile Pro Ala Glu
            900                 905                 910

Gln Ile Val Cys Glu Met Gly Glu Ala Lys Pro Ser Gln His Ala Gly
        915                 920                 925

Phe Val Glu Ile Cys Val Ala Val Cys Arg Pro Glu Phe Met Ala Arg
    930                 935                 940

Ser Ser Gln Leu Tyr Tyr Phe Met Thr Leu Thr Leu Ser Asp Leu Lys
945                 950                 955                 960

Pro Ser Arg Gly Pro Met Ser Gly Gly Thr Gln Val Thr Ile Thr Gly
                965                 970                 975

Thr Asn Leu Asn Ala Gly Ser Asn Val Val Val Met Phe Gly Lys Gln
            980                 985                 990

Pro Cys Leu Phe His Arg Arg Ser Pro Ser Tyr Ile Val Cys Asn Thr
        995                 1000                1005

Thr Ser Ser Asp Glu Val Leu Glu Met Lys Val Ser Val Gln Val
    1010                1015                1020

Asp Arg Ala Lys Ile His Gln Asp Leu Val Phe Gln Tyr Val Glu
    1025                1030                1035

Asp Pro Thr Ile Val Arg Ile Glu Pro Glu Trp Ser Ile Val Ser
    1040                1045                1050

Gly Asn Thr Pro Ile Ala Val Trp Gly Thr His Leu Asp Leu Ile
    1055                1060                1065

Gln Asn Pro Gln Ile Arg Ala Lys His Gly Gly Lys Glu His Ile
```

```
                 1070               1075               1080
Asn Ile Cys Glu Val Leu Asn Ala Thr Glu Met Thr Cys Gln Ala
    1085               1090               1095

Pro Ala Leu Ala Leu Gly Pro Asp His Gln Ser Asp Leu Thr Glu
    1100               1105               1110

Arg Pro Glu Glu Phe Gly Phe Ile Leu Asp Asn Val Gln Ser Leu
    1115               1120               1125

Leu Ile Leu Asn Lys Thr Asn Phe Thr Tyr Tyr Pro Asn Pro Val
    1130               1135               1140

Phe Glu Ala Phe Gly Pro Ser Gly Ile Leu Glu Leu Lys Pro Gly
    1145               1150               1155

Thr Pro Ile Ile Leu Lys Gly Lys Asn Leu Ile Pro Pro Val Ala
    1160               1165               1170

Gly Gly Asn Val Lys Leu Asn Tyr Thr Val Leu Val Gly Glu Lys
    1175               1180               1185

Pro Cys Thr Val Thr Val Ser Asp Val Gln Leu Leu Cys Glu Ser
    1190               1195               1200

Pro Asn Leu Ile Gly Arg His Lys Val Met Ala Arg Val Gly Gly
    1205               1210               1215

Met Glu Tyr Ser Pro Gly Met Val Tyr Ile Ala Pro Asp Ser Pro
    1220               1225               1230

Leu Ser Leu Pro Ala Ile Val Ser Ile Ala Val Ala Gly Gly Leu
    1235               1240               1245

Leu Ile Ile Phe Ile Val Ala Val Leu Ile Ala Tyr Lys Arg Lys
    1250               1255               1260

Ser Arg Glu Ser Asp Leu Thr Leu Lys Arg Leu Gln Met Gln Met
    1265               1270               1275

Asp Asn Leu Glu Ser Arg Val Ala Leu Glu Cys Lys Glu Ala Phe
    1280               1285               1290

Ala Glu Leu Gln Thr Asp Ile His Glu Leu Thr Ser Asp Leu Asp
    1295               1300               1305

Gly Ala Gly Ile Pro Phe Leu Asp Tyr Arg Thr Tyr Thr Met Arg
    1310               1315               1320

Val Leu Phe Pro Gly Ile Glu Asp His Pro Val Leu Arg Asp Leu
    1325               1330               1335

Glu Val Pro Gly Tyr Arg Gln Glu Arg Val Glu Lys Gly Leu Lys
    1340               1345               1350

Leu Phe Ala Gln Leu Ile Asn Asn Lys Val Phe Leu Leu Ser Phe
    1355               1360               1365

Ile Arg Thr Leu Glu Ser Gln Arg Ser Phe Ser Met Arg Asp Arg
    1370               1375               1380

Gly Asn Val Ala Ser Leu Ile Met Thr Val Leu Gln Ser Lys Leu
    1385               1390               1395

Glu Tyr Ala Thr Asp Val Leu Lys Gln Leu Leu Ala Asp Leu Ile
    1400               1405               1410

Asp Lys Asn Leu Glu Ser Lys Asn His Pro Lys Leu Leu Leu Arg
    1415               1420               1425

Arg Thr Glu Ser Val Ala Glu Lys Met Leu Thr Asn Trp Phe Thr
    1430               1435               1440

Phe Leu Leu Tyr Lys Phe Leu Lys Glu Cys Ala Gly Glu Pro Leu
    1445               1450               1455

Phe Ser Leu Phe Cys Ala Ile Lys Gln Gln Met Glu Lys Gly Pro
    1460               1465               1470
```

-continued

```
Ile Asp Ala Ile Thr Gly Glu Ala Arg Tyr Ser Leu Ser Glu Asp
    1475                1480                1485

Lys Leu Ile Arg Gln Gln Ile Asp Tyr Lys Thr Leu Val Leu Ser
    1490                1495                1500

Cys Val Ser Pro Asp Asn Ala Asn Ser Pro Glu Val Pro Val Lys
    1505                1510                1515

Ile Leu Asn Cys Asp Thr Ile Thr Gln Val Lys Glu Lys Ile Leu
    1520                1525                1530

Asp Ala Ile Phe Lys Asn Val Pro Cys Ser His Arg Pro Lys Ala
    1535                1540                1545

Ala Asp Met Asp Leu Glu Trp Arg Gln Gly Ser Gly Ala Arg Met
    1550                1555                1560

Ile Leu Gln Asp Glu Asp Ile Thr Thr Lys Ile Glu Asn Asp Trp
    1565                1570                1575

Lys Arg Leu Asn Thr Leu Ala His Tyr Gln Val Pro Asp Gly Ser
    1580                1585                1590

Val Val Ala Leu Val Ser Lys Gln Val Thr Ala Tyr Asn Ala Val
    1595                1600                1605

Asn Asn Ser Thr Val Ser Arg Thr Ser Ala Ser Lys Tyr Glu Asn
    1610                1615                1620

Met Ile Arg Tyr Thr Gly Ser Pro Asp Ser Leu Arg Ser Arg Thr
    1625                1630                1635

Pro Met Ile Thr Pro Asp Leu Glu Ser Gly Val Lys Met Trp His
    1640                1645                1650

Leu Val Lys Asn His Glu His Gly Asp Gln Lys Glu Gly Asp Arg
    1655                1660                1665

Gly Ser Lys Met Val Ser Glu Ile Tyr Leu Thr Arg Leu Leu Ala
    1670                1675                1680

Thr Lys Gly Thr Leu Gln Lys Phe Val Asp Asp Leu Phe Glu Thr
    1685                1690                1695

Ile Phe Ser Thr Ala His Arg Gly Ser Ala Leu Pro Leu Ala Ile
    1700                1705                1710

Lys Tyr Met Phe Asp Phe Leu Asp Glu Gln Ala Asp Lys His Gly
    1715                1720                1725

Ile His Asp Pro His Val Arg His Thr Trp Lys Ser Asn Cys Leu
    1730                1735                1740

Pro Leu Arg Phe Trp Val Asn Met Ile Lys Asn Pro Gln Phe Val
    1745                1750                1755

Phe Asp Ile His Lys Asn Ser Ile Thr Asp Ala Cys Leu Ser Val
    1760                1765                1770

Val Ala Gln Thr Phe Met Asp Ser Cys Ser Thr Ser Glu His Arg
    1775                1780                1785

Leu Gly Lys Asp Ser Pro Ser Asn Lys Leu Leu Tyr Ala Lys Asp
    1790                1795                1800

Ile Pro Ser Tyr Lys Asn Trp Val Glu Arg Tyr Tyr Ser Asp Ile
    1805                1810                1815

Gly Lys Met Pro Ala Ile Ser Asp Gln Asp Met Asn Ala Tyr Leu
    1820                1825                1830

Ala Glu Gln Ser Arg Met His Met Asn Glu Phe Asn Thr Met Ser
    1835                1840                1845

Ala Leu Ser Glu Ile Phe Ser Tyr Val Gly Lys Tyr Ser Glu Glu
    1850                1855                1860
```

-continued

```
Ile Leu Gly Pro Leu Asp His Asp Asp Gln Cys Gly Lys Gln Lys
    1865                1870                1875

Leu Ala Tyr Lys Leu Glu Gln Val Ile Thr Leu Met Ser Leu Asp
    1880                1885                1890

Ser

<210> SEQ ID NO 17
<211> LENGTH: 12
<212> TYPE: PRT
<213> ORGANISM: Artificial Sequence
<220> FEATURE:
<223> OTHER INFORMATION: Myc tag

<400> SEQUENCE: 17

Gly Gly Glu Gln Lys Leu Ile Ser Glu Glu Asp Leu
1               5                   10

<210> SEQ ID NO 18
<211> LENGTH: 29
<212> TYPE: DNA
<213> ORGANISM: Artificial sequence
<220> FEATURE:
<223> OTHER INFORMATION: Forward primer

<400> SEQUENCE: 18
gcagtgcacc aaggagcctg tcccaatcg                                   29

<210> SEQ ID NO 19
<211> LENGTH: 29
<212> TYPE: DNA
<213> ORGANISM: Artificial sequence
<220> FEATURE:
<223> OTHER INFORMATION: Reverse primer

<400> SEQUENCE: 19
cgattgggac aggctccttg gtgcactgc                                   29
```

USE OF SEMAPHORIN 6A FOR PROMOTING MYELINATION AND OLIGODENDROCYTE DIFFERENTIATION

CROSS-REFERENCE TO RELATED APPLICATIONS

The present application is the National Stage of International Application No. PCT/US2008/001444, filed Feb. 4, 2008, which claims the benefit of U.S. Provisional Application No. 60/898,992, filed Feb. 2, 2007, all of which are incorporated herein by reference in their entireties.

REFERENCE TO SEQUENCE LISTING SUBMITTED ELECTRONICALLY VIA EFS-WEB

The content of the electronically submitted sequence listing (Name: sequence listing ascii.txt; Size: 126,976 bytes; Date of Creation: Mar. 29, 2010) submitted in this application is incorporated herein by reference in its entirety.

BACKGROUND OF THE INVENTION

1. Field of the Invention

This invention relates to neurobiology, neurology and pharmacology. More particularly, it relates to methods of treating diseases relating to central nervous system myelination by the administration of semaphorin 6A ("Sema6A") polypeptide.

2. Background Art

Many diseases of the nervous system are associated with demyelination and dysmyelination, including multiple sclerosis (MS), progressive multifocal leukoencephalopathy (PML), encephalomyelitis (EPL), central pontine myelolysis (CPM), Wallerian Degeneration and some inherited diseases such as adrenoleukodystrophy, Alexander's disease, and Pelizaeus Merzbacher disease (PMZ). Among these diseases, MS is the most widespread, affecting approximately 2.5 million people worldwide.

MS generally begins with a relapsing-remitting pattern of neurologic involvement, which then progresses to a chronic phase with increasing neurological damage. MS is associated with the destruction of myelin, oligodendrocytes and axons localized to chronic lesions. The demyelination observed in MS is not always permanent and remyelination has been documented in early stages of the disease. Remyelination of central nervous system ("CNS") neurons requires oligodendrocytes.

Various disease-modifying treatments are available for MS, including the use of corticosteroids and immunomodulators such as interferon beta. In addition, because of the central role of oligodendrocytes and myelination in MS, there have been efforts to develop therapies to increase oligodendrocyte numbers or enhance myelination. See, e.g., Cohen et al., U.S. Pat. No. 5,574,009; Chang et al., *N. Engl. J. Med.* 346:165-73 (2002). However, there remains an urgent need to devise additional therapies for MS.

Semaphorins are secreted or membrane-bound proteins that are known to control axon guidance and cell migration. Kerjan et al., *Nat. Neursci.* 8(11): 1516-1524 (2005). Many transmembrane semaphorins are expressed in the developing CNS, but little is known of their functions in vivo. Id. Class 6 semaphorins comprise four proteins, Sema6A-Sema6D, that are closely related to invertebrate transmembrane semaphorins. Fiore & Puschel. *Front. Biosci.* 8:2484-2499 (2003). All semaphorins possess a semaphorin (Sema) domain and a plexin-semaphorin-integrin (PSI) domain (found in plexins, semaphorins and integrins) in the N-terminal extracellular portion.

Plexins are a family of molecules (the plexin family) which are distributed in various animal species. Murakami et al., *Dev. Dynam.* 220: 246-258 (2001). Plexins are grouped into four sub-families, i.e., plexin-A, -B, -C, and -D. Id. In mouse and human, four members of the plexin-A subfamily (plexin-A1, -A2, -A3, and -A4) have been isolated. See Kameyama et al., *Biochem. Biophys. Res. Commun.* 226: 396-402 (1996); Kameyama et al., *Biochem. Biophys. Res. Commun.* 226: 524-529 (1996); Maestrini et al., *Proc. Natl. Acad. Sci. USA* 93: 674-678 (1996); Tamagnone et al., *Cell* 99: 71-80 (1999); and Suto et al., *Mech. Dev.* 120: 385-396 (2003). The ectodomains of the plexin-A subfamily possess a stretch of approximately 500 amino acids (aa) residues which exhibit significant homology to the sema domain shared by semaphorins. Murakami et al., *Develop. Dyn.* 220: 246-258 (2001). Type-A plexins are known to interact with class 6 semaphorins. Toyofuku et al., *Genes Develop.* 18: 435-447 (2004). For example, Suto et al. showed that plexin-A4 is a direct receptor for Sema6A. *J. Neurosci.* 25(14): 3628-3637 (2005).

BRIEF SUMMARY OF THE INVENTION

The present invention is based on the discovery that semaphorin 6A (Sema6A) is expressed in oligodendrocytes and regulates oligodendrocyte differentiation, survival and/or axon myelination. Furthermore, certain Sema6A polypeptides promote survival, proliferation and/or differentiation of oligodendrocytes as well as myelination of neurons. Based on these discoveries, the invention relates generally to methods of treating conditions associated with demyelination and/or dysmyelination (e.g. multiple sclerosis) by the administration of a Sema6A polypeptide.

In certain embodiments, the invention includes a method for promoting proliferation, differentiation, or survival of oligodendrocytes, comprising contacting oligodendrocytes with an effective amount of a composition comprising an isolated Sema6A polypeptide. In other embodiments, the invention includes a method for promoting oligodendrocyte-mediated myelination of neurons, comprising contacting a mixture of neurons and oligodendrocytes with an effective amount of a composition comprising a Sema6A polypeptide.

The present invention is directed to a method for promoting proliferation, differentiation, or survival of oligodendrocytes in a mammal or a method for promoting myelination of neurons in a mammal, comprising administering to a mammal in need thereof an effective amount of a composition comprising a Sema6A polypeptide.

Also included is a method for treating a disease, disorder, or injury associated with dysmyelination or demyelination or associated with oligodendrocyte death or lack of differentiation in a mammal comprising administering to a mammal in need thereof a therapeutically effective amount of a composition comprising a Sema6A polypeptide.

Further included is a method for treating a disease, disorder, or injury involving the destruction of myelin in a mammal comprising administering a therapeutically effective amount of a composition comprising a Sema6A polypeptide.

Additionally included is a method of the present invention described herein, where the Sema6A polypeptide binds to a plexin-A2 polypeptide or a plexin-A4 polypeptide. In other embodiments, the Sema6A polypeptide is isolated.

Further embodiments of the invention include a method of treating a disease, disorder or injury involving the destruction of oligodendrocytes or myelin by in vivo gene therapy, comprising administering to a mammal, at or near the site of the disease, disorder or injury, a vector comprising a nucleotide sequence that encodes a Sema6A polypeptide so that the Sema6A polypeptide is expressed from the nucleotide sequence in the mammal in an amount sufficient to promote axonal extension by neurons at or near the site of the injury. In certain embodiments, the present invention includes a method for promoting proliferation, differentiation, or survival of oligodendrocytes or for promoting myelination of neurons in a mammal, comprising administering to a mammal in need thereof an effective amount of a composition comprising a polynucleotide, which encodes a Sema6A polypeptide.

Additionally, the invention includes a method for treating a disease, disorder, or injury associated with dysmyelination or demyelination or associated with oligodendrocyte death or lack of differentiation in a mammal comprising administering to a mammal in need thereof a therapeutically effective amount of a composition comprising a polynucleotide, which encodes a Sema6A polypeptide. The invention further includes a method for treating a disease, disorder, or injury involving the destruction of myelin in a mammal comprising administering a therapeutically effective amount of a composition comprising a polynucleotide, which encodes a Sema6A polypeptide. In certain embodiments, the Sema6A polypeptide of the present invention binds to a plexin-A2 polypeptide or a plexin-A4 polypeptide. The polynucleotide used in the method of the present invention can be isolated.

In certain embodiments, the vector is a viral vector which is selected from the group consisting of an adenoviral vector, an alphavirus vector, an enterovirus vector, a pestivirus vector, a lentiviral vector, a baculoviral vector, a herpesvirus vector, an Epstein Ban viral vector, a papovaviral vector, a poxvirus vector, a vaccinia viral vector, and a herpes simplex viral vector.

In some embodiments, the disease, disorder, injury or condition is selected from the group consisting of multiple sclerosis (MS), progressive multifocal leukoencephalopathy (PML), encephalomyelitis (EPL), central pontine myelolysis (CPM), adrenoleukodystrophy, Alexander's disease, Pelizaeus Merzbacher disease (PMZ), Globoid cell Leucodystrophy (Krabbe's disease), Wallerian Degeneration, optic neuritis, transverse myelitis, amylotrophic lateral sclerosis (ALS), Huntington's disease, Alzheimer's disease, Parkinson's disease, spinal cord injury, traumatic brain injury, post radiation injury, neurologic complications of chemotherapy, stroke, acute ischemic optic neuropathy, vitamin E deficiency, isolated vitamin E deficiency syndrome, AR, Bassen-Kornzweig syndrome, Marchiafava-Bignami syndrome, metachromatic leukodystrophy, trigeminal neuralgia, and Bell's palsy. In some embodiments, the cultured host cell is derived from the mammal to be treated.

Certain Sema6A polypeptides include, but are not limited to, Sema6A polypeptides fragments, variants, or derivatives thereof which lack a transmembrane domain and a cytoplasmic domain. Sema6A polypeptides include polypeptides comprising (i) a signal sequence, (ii) a sema domain, (iii) a PSI domain, (iv) an extracellular domain, (v) a transmembrane domain, (vi) a cytoplasmic domain, and (vii) a combination of two or more of the domains. In some embodiments, the Sema6A polypeptide lacks a signal sequence, a sema domain, a PSI domain, a transmembrane domain, a cytoplasmic domain, or a combination of two or more of the domains. In some embodiments, the Sema6A polypeptide comprises a Sema domain and lacks a signal sequence, a PSI sequence, a transmembrane domain, and a cytoplasmic domain. In some embodiments, the Sema6A polypeptide comprises amino acid residues 1-649 of SEQ ID NO: 2.

In some embodiments, the Sema6A polypeptide is administered by bolus injection or chronic infusion. In some embodiments, the Sema6A polypeptide is administered directly into the central nervous system. In some embodiments, the Sema6A polypeptide is administered directly into a chronic lesion of MS.

In some embodiments, the Sema6A polypeptide is a fusion polypeptide comprising a non-Sema6A moiety. In some embodiments, the non-Sema6A moiety is selected from the group consisting of an antibody Ig moiety, a serum albumin moiety, a targeting moiety, a reporter moiety, and a purification-facilitating moiety. In some embodiments, the antibody Ig moiety is a hinge and Fc moiety.

In some embodiments, the polypeptides of the present invention are conjugated to a polymer. In some embodiments, the polymer is selected from the group consisting of a polyalkylene glycol, a sugar polymer, and a polypeptide. In some embodiments, the polyalkylene glycol is polyethylene glycol (PEG). In some embodiments, the polypeptides of the present invention are conjugated to 1, 2, 3 or 4 polymers. In some embodiments, the total molecular weight of the polymers is from 5,000 Da to 100,000 Da.

BRIEF DESCRIPTION OF THE DRAWINGS/FIGURES

Figure 3:
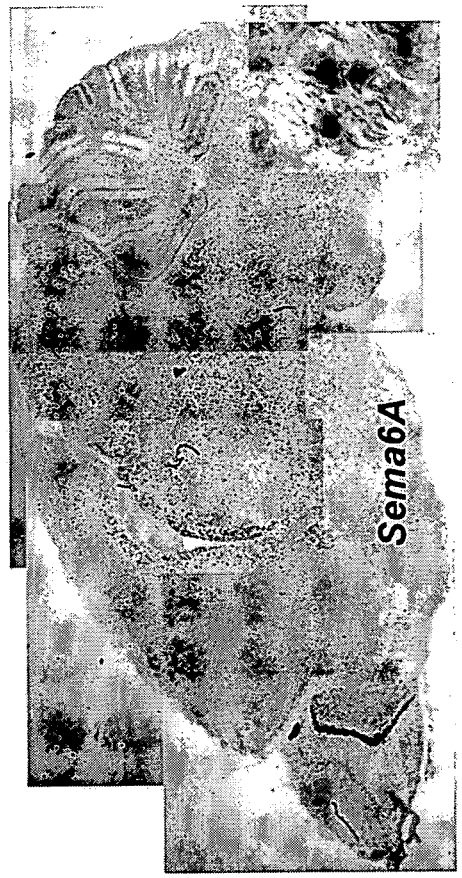

FIG. 3: Sema6A expression in mouse nervous system. Sema6A expression of in the P15 mouse nervous system was analyzed by In situ hybridization. Most cells expressing Sema6A are found in the white matter. Sema6A expressing cells in the white matter are oligodendrocytes.

FIG. 4A-4C: Immunostaining analysis of Myelin proteolipid protein (PLP) expressing Sema6A+/− (A) or Sema6A−/− (B) oligodendrocytes in the anterior commissure (AC) at P16. (C)—Quantification of PLP expressing cells in AC at different stages, i.e., P16, P30, and P45.

FIG. 5A-5D: (A)—In vitro maturation of Sema6A−/− oligodendrocytes. The fractal dimension (FD) of the oligodendrocytes was measured after 48 hrs. Left bars are FD of Sema6A−/− oligodendrocytes, and right bars are FD of Sema6A+/− oligodendrocytes. (B)—Oligodendrocytes of Sema6A−/− at 48 hrs visualized by phase contrast microscopy and immunostaining with anti-O4 antibody. (C): In vitro maturation of Sema6A−/− oligodendrocyte at 24 hr and 48 hr. Left bars are 24 hr, and right bars are 48 hr. (D): Oligodendrocytes of Sema6A+/− at 48 hrs visualized by phase contrast microscopy and immunostaining with anti-O4 antibody.

FIGS. 6A-6C: Myelination in cocultures of the dorsal root ganglion cells (DRG) and oligodendrocytes with addition of Sema6A-Fc at various dosages, (A) negative control; (B) 0.1 µg/ml; and (C) 0.3 µg/ml. The degree of myelination is shown by immunostaining with anti MBP antibody.

Figure 7:
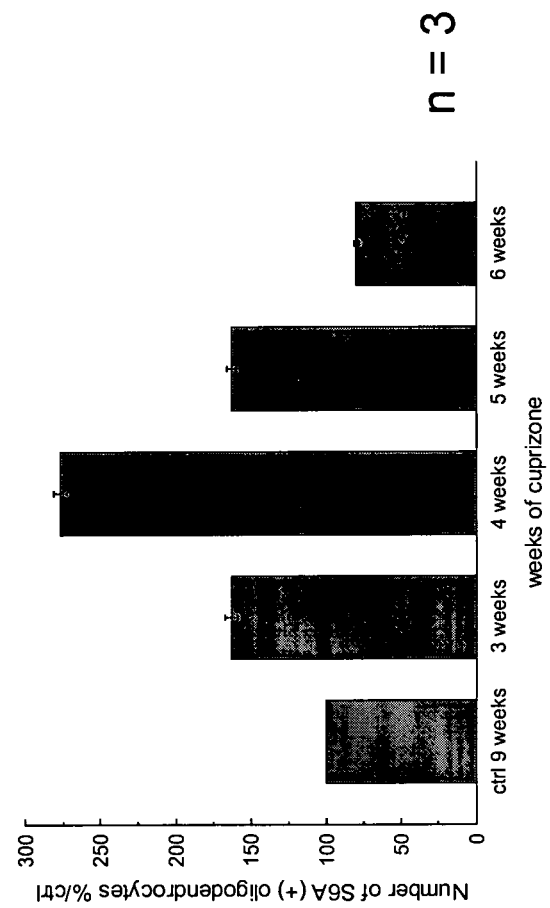

FIG. 7: Mice were treated with cuprizone and examined for the Sema6A expression during demyelination and remyelination. The number of Sema6A expressing cells was measured at different stages, i.e., 3-6 weeks.

FIG. 8: (A)-(B) In situ hybridization using a Sema6A riboprobe in human MS lesion tissue and non-lesion tissue at ×1 magnification (A) and ×1 magnification (B); (C) Immunostaining of human MS lesion tissue using human Sema6A antibody at ×10 magnification.

FIG. 9A-D: (A) Western blot analysis of plexin-A2 polypeptide expression in plexin-A2+/+ (wildtype), plexin-A2 protein null knockout (plexin-A2−/−) mice and plexin-A2 mutant bearing a single amino acid substitution (A396E) in the Semaphorin domain (NMF454); (B) Sequence alignment of plexin-A2, plexin-A4, plexin-A1, and plexin-A3 to identify alanine (396); (C) Sema6A binding assay to wildtype plexin-A2 protein expressed in COS cells; and (D) Sema6A binding assay to mutated plexin-A2A396E expressed in COS cells.

DETAILED DESCRIPTION OF THE INVENTION

Definitions

Unless defined otherwise, all technical and scientific terms used herein have the same meaning as commonly understood by one of ordinary skill in the art to which this invention belongs. In case of conflict, the present application including the definitions will control. Unless otherwise required by context, singular terms shall include pluralities and plural terms shall include the singular. All publications, patents and other references mentioned herein are incorporated by reference in their entireties for all purposes as if each individual publication or patent application were specifically and individually indicated to be incorporated by reference.

Although methods and materials similar or equivalent to those described herein can be used in practice or testing of the present invention, suitable methods and materials are described below. The materials, methods and examples are illustrative only and are not intended to be limiting. Other features and advantages of the invention will be apparent from the detailed description and from the claims.

In order to further define this invention, the following terms and definitions are provided.

It is to be noted that the term "a" or "an" entity, refers to one or more of that entity; for example, "a polypeptide," is understood to represent one or more polypeptides. As such, the terms "a" (or "an"), "one or more," and "at least one" can be used interchangeably herein.

Throughout this specification and claims, the word "comprise," or variations such as "comprises" or "comprising," indicate the inclusion of any recited integer or group of integers but not the exclusion of any other integer or group of integers.

Throughout the specification and claims, the term "consists of" and variations such as "consist of" or "consisting of" indicate the inclusion of any recited integer or group of integers but that no additional integer or group of integers may be added to the specified method, structure, or composition.

Throughout the specification and claims, the term "consists essentially of" and variations such as "consist essentially of" or "consisting essentially of" indicate the inclusion of any recited integer or group of integers and the optional inclusion of any recited integer or group of integers that do not materially change the basic or novel properties of the specified method, structure, or composition.

As used herein, "antibody" means an intact immunoglobulin, or an antigen-binding fragment thereof. Antibodies of this invention can be of any isotype or class (e.g., M, D, G, E and A) or any subclass (e.g., G1-4, A1-2) and can have either a kappa (κ) or lambda (λ) light chain.

As used herein, "Fc" means a portion of an immunoglobulin heavy chain that comprises one or more heavy chain constant region domains, CH1, CH2 and CH3. For example, a portion of the heavy chain constant region of an antibody that is obtainable by papain digestion.

As used herein, "humanized antibody" means an antibody in which at least a portion of the non-human sequences are replaced with human sequences. Examples of how to make humanized antibodies may be found in U.S. Pat. Nos. 6,054,297, 5,886,152 and 5,877,293.

As used herein, "chimeric antibody" means an antibody that contains one or more regions from a first antibody and one or more regions from at least one other antibody. The first antibody and the additional antibodies can be from the same or different species.

As used herein, a "therapeutically effective amount" refers to an amount effective, at dosages and for periods of time necessary, to achieve a desired therapeutic result. A therapeutic result may be, e.g., lessening of symptoms, prolonged survival, improved mobility, and the like. A therapeutic result need not be a "cure".

As used herein, a "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

As used herein, a "polynucleotide" can contain the nucleotide sequence of the full length cDNA sequence, including the untranslated 5' and 3' sequences, the coding sequences, as well as fragments, epitopes, domains, and variants of the nucleic acid sequence. The polynucleotide can be composed of any polyribonucleotide or polydeoxyribonucleotide, which may be unmodified RNA or DNA or modified RNA or DNA. For example, polynucleotides can be composed of single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, the polynucleotides can be composed of triple-stranded regions comprising RNA or DNA or both RNA and DNA. Polynucleotides may also contain one or more modified bases or DNA or RNA backbones modified for stability or for other reasons. "Modified" bases include, for example, tritylated bases and unusual bases such as inosine. A variety of modifications can be made to DNA and RNA; thus, "polynucleotide" embraces chemically, enzymatically, or metabolically modified forms.

In the present invention, a polypeptide can be composed of amino acids joined to each other by peptide bonds or modified peptide bonds, i.e., peptide isosteres, and may contain amino acids other than the 20 gene-encoded amino acids (e.g. non-naturally occurring amino acids). The polypeptides of the present invention may be modified by either natural process, such as posttranslational processing, or by chemical modification techniques which are well known in the art. Such modifications are well described in basic texts and in more detailed monographs, as well as in a voluminous research literature. Modifications can occur anywhere in the polypeptide, including the peptide backbone, the amino acid side-chains and the amino or carboxyl termini. It will be appreciated that the same type of modification may be present in the same or varying degrees at several sites in a given polypeptide. Also, a given polypeptide may contain many types of modifications. Polypeptides may be branched, for example, as a result of ubiquitination, and they may be cyclic, with or without branching. Cyclic, branched, and branched cyclic polypeptides may result from posttranslation natural processes or may be made by synthetic methods. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristoylation, oxidation, pegylation, proteolytic processing, phosphorylation, prenylation, racemization, selenoylation, sulfation, transfer-RNA mediated addition of amino acids to proteins such as arginylation, and ubiquitination. (See, for instance, Proteins—Structure And Molecular Properties, 2nd Ed., T.E. Creighton, W.H. Freeman and Company, New York (1993); Posttranslational Covalent Modification of Proteins, B. C. Johnson, Ed., Academic Press, New York, pgs. 1-12 (1983); Seifter et al., *Meth Enzymol* 182:626-646 (1990); Rattan et al., *Ann NY Acad Sci* 663:48-62 (1992).)

The terms "fragment," "variant," "derivative" and "analog" when referring to a Sema6A polypeptide of the present invention include any polypeptides which retain at least some immunogenicity, i.e., the ability to induce an immune response against sema6A, or any naturally-occurring function of Sema6A, e.g., the ability to bind to any one of plexin-A subfamily polypeptides, i.e., plexin-A1, plexin-A2, plexin-A3, or plexin-A4. An example of the naturally-occurring Sema6A function is its ability to bind to plexin-A2 or plexin-A4 polypeptide. Sema6A polypeptides as described herein may include fragment, variant, or derivative molecules without limitation, so long as the Sema6A polypeptide still retains immunogenicity or any one naturally-occurring function. Sema6A polypeptides of the present invention may include Sema6A proteolytic fragments, deletion fragments and in particular, fragments which more easily reach the site of action when delivered to an animal. Polypeptide fragments further include any portion of the polypeptide which comprises an antigenic or immunogenic epitope of the native polypeptide, including linear as well as three-dimensional epitopes. Sema6A polypeptides of the present invention may comprise variant Sema6A regions, including fragments as described above, and also polypeptides with altered amino acid sequences due to amino acid substitutions, deletions, or insertions. Variants may occur naturally, such as an allelic variant. By an "allelic variant" is intended alternate forms of a gene occupying a given locus on a chromosome of an organism. Genes II, Lewin, B., ed., John Wiley & Sons, New York (1985). Non-naturally occurring variants may be produced using art-known mutagenesis techniques. Sema6A polypeptides may comprise conservative or non-conservative amino acid substitutions, deletions or additions. Sema6A polypeptide of the present invention may also include derivative molecules. For example, Sema6A polypeptides of the present invention may include Sema6A regions which have been altered so as to exhibit additional features not found on the native polypeptide. Examples include fusion proteins and protein conjugates.

In the present invention, a "polypeptide fragment" or "protein fragment" refers to a short amino acid sequence of a Sema6A polypeptide. Protein or polypeptide fragments may be "free-standing," or comprised within a larger polypeptide of which the fragment forms a part of region. Representative examples of polypeptide fragments of the invention, include, for example, fragments comprising about 5 amino acids, about 10 amino acids, about 15 amino acids, about 20 amino acids, about 30 amino acids, about 40 amino acids, about 50 amino acids, about 60 amino acids, about 70 amino acids, about 80 amino acids, about 90 amino acids, and about 100 amino acids.

As used herein, the terms "linked," "fused" or "fusion" are used interchangeably. These terms refer to the joining together of two more elements or components, by whatever means including chemical conjugation or recombinant means. An "in-frame fusion" refers to the joining of two or more open reading frames (ORFs) to form a continuous longer ORF, in a manner that maintains the correct reading frame of the original ORFs. Thus, the resulting recombinant fusion protein is a single protein containing two ore more segments that correspond to polypeptides encoded by the original ORFs (which segments are not normally so joined in nature.) Although the reading frame is thus made continuous throughout the fused segments, the segments may be physically or spatially separated by, for example, in-frame linker sequence.

In the context of polypeptides, a "linear sequence" or a "sequence" is an order of amino acids in a polypeptide in an amino to carboxyl terminal direction in which residues that neighbor each other in the sequence are contiguous in the primary structure of the polypeptide.

The term "expression" as used herein refers to a process by which a gene produces a biochemical, for example, an RNA or polypeptide. The process includes any manifestation of the functional presence of the gene within the cell including, without limitation, gene knockdown as well as both transient expression and stable expression. It includes without limitation transcription of the gene into messenger RNA (mRNA), transfer RNA (tRNA), small hairpin RNA (shRNA), small interfering RNA (siRNA) or any other RNA product and the translation of such mRNA into polypeptide(s). If the final desired product is biochemical, expression includes the creation of that biochemical and any precursors.

By "subject" or "individual" or "animal" or "patient" or "mammal," is meant any subject, particularly a mammalian subject, for whom diagnosis, prognosis, or therapy is desired. Mammalian subjects include, but are not limited to, humans, domestic animals, farm animals, zoo animals, sport animals, pet animals such as dogs, cats, guinea pigs, rabbits, rats, mice, horses, cattle, cows; primates such as apes, monkeys, orangutans, and chimpanzees; canids such as dogs and wolves; felids such as cats, lions, and tigers; equids such as horses, donkeys, and zebras; bears, food animals such as cows, pigs, and sheep; ungulates such as deer and giraffes; rodents such as mice, rats, hamsters and guinea pigs; and so on. In certain embodiments, the mammal is a human subject.

Sema6A

The invention is based on the discovery that Sema6A polypeptides increase oligodendrocyte numbers by promoting their survival, proliferation and/or differentiation. In addition, the inventors have discovered that Sema6A polypeptides promote myelination of neurons.

Naturally occurring human Sema6A polypeptide is known to be expressed in developing brain, kidney, lung and liver. Sema6A is also detected in human adult tissues such as the skin (dendritic cells), and in the highly regenerative placental tissues. The human Sema6A gene consists of 20 exons, including 2 untranslated exons, covering approximately 60 kb of genomic sequence on chromosome 5.

Figure 1:
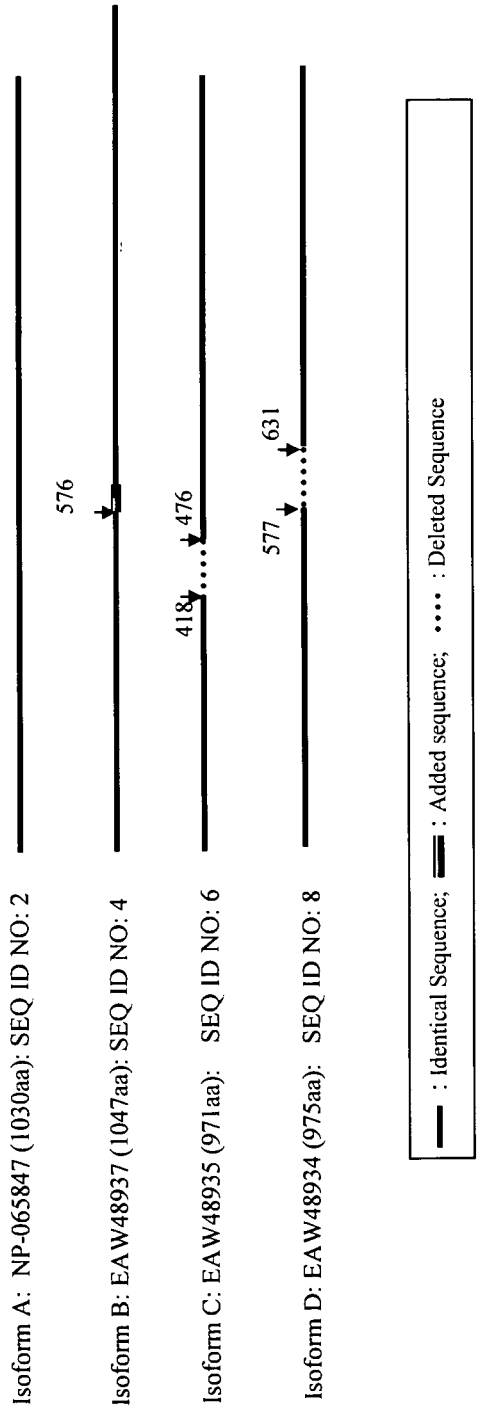
FIG. 1 is a sequence comparison among human Sema6A polypeptide isoforms, i.e., isoforms A-D.
Figure 2:
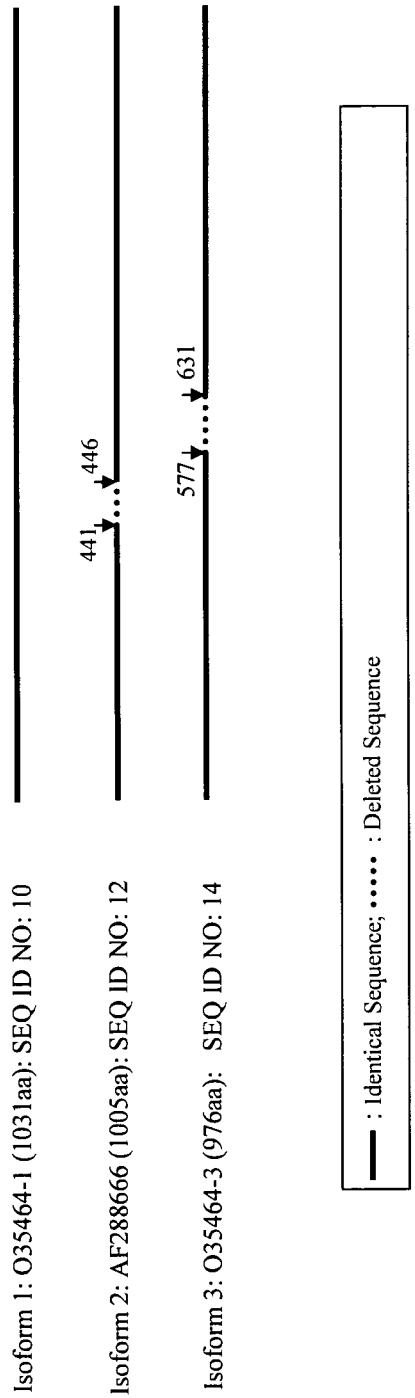
FIG. 2 is a sequence comparison among mouse Sema6A polypeptide isoforms, i.e., isoforms 1-3.

The full-length human Sema6A polypeptide consists of a signal sequence, an extracellular domain, a transmembrane domain and a cytoplasmic domain. The extracellular domain comprises a sema domain and a plexin-semaphorin-integrin (PSI) domain. Full-length human Sema6A polypeptides vary from about 971 amino acids to about 1049 amino acids in length, depending on the variants. See FIG. 1. Similar variants occur in mouse Sema6A. See, e.g., FIG. 2.

A polypeptide sequence of 1030aa was reported as a human Sema6A polypeptide sequence and has the accession number NP-01165847 in Genbank. The human Sema6A polypeptide sequence is designated herein as isoform A and SEQ ID NO: 2. SEQ ID NO: 1 is a nucleotide sequence encoding SEQ ID NO: 2. A polypeptide sequence of 1047aa was reported as a variant of the human Sema6A polypeptide sequence and has the accession number EAW48937 in Genbank. The 1047aa polypeptide is designated herein as isoform B and SEQ ID NO: 4. A nucleotide sequence encoding SEQ ID NO: 4 is SEQ ID NO: 3. Another variant of the human Sema6A polypeptide having 971aa was reported as the accession number EAW48935 in Genbank. The 971aa polypeptide is designated herein as isoform C and SEQ ID NO: 6. A polypeptide sequence of 975aa was reported as a human Sema6A polypeptide variant and has the accession number EAW48934 in Genbank. The 975aa polypeptide sequence is designated herein as isoform D and SEQ ID NO: 8. Variants of human Sema6A include, but are not limited to, the Sema6A polypeptide of isoform A with a deletion after amino acids 1001, resulting in a polypeptide with 1000 amino acids. Nakayama et al., *Genome Res.* 12(11): 1773-1784 (2002); Strausberg et al., *Proc. Natl. Acad. Sci. U.S.A.* 99(26): 16899-16903 (2002). Other Sema6A variants are also known, for example, in Prislei et al. *Mol Cancer Ther.* 7(1): 233-241 (2007).

The mouse Sema6A polypeptide sequence and its variants are also reported. The 1031 aa mouse Sema6A polypeptide has the accession number O35464 in UniProtKB/Swiss-Prot entry. The polypeptide is designated herein as isoform 1 and SEQ ID NO: 10. A nucleotide sequence encoding SEQ ID NO: 10 is designated as SEQ ID NO: 9. Another polypeptide sequence of 1005aa was reported as a mouse Sema6A polypeptide sequence and has the accession number AF288666 in Genbank. The polypeptide sequence is designated as isoform 2 and SEQ ID NO: 12. A nucleotide sequence encoding SEQ ID NO: 12 is designated herein as SEQ ID NO: 11. Another variant of the mouse Sema6A polypeptide sequence was reported as the accession number O35464 in UniProtKB/Swiss-Prot entry. The polypeptide sequence is designated herein as isoform 3 and SEQ ID NO: 14. A nucleotide sequence encoding SEQ ID NO: 14 is SEQ ID NO: 13. Variants of mouse Sema6A include, but are not limited to, the polypeptides with the following mutations: A172V, L201P, N337D, S585N, Q685R, TK703-704SE, P735S, Q766E, I856T, or KSPNHGVNLVENLDSLPP-KVPQREAS863-888ESSPYVLKQFSEAFNRQGIILS-VAVE.

Sema6A polypeptides known in other animals include, but are not limited to, chimpanzee, dog, and zebra fish. There are variants of Chimpanzee Sema6A polypeptides, e.g., Genbank Accession Nos. XP_001150634, XP_001150901, XP_001150706, XP_001151177, XP_001151109, XP_001151041, XP_001150971, and XP_517889. Non-limiting examples of dog Sema6A polypeptide variants are Genbank Accession Nos. XP_538552, XP_859002, XP_858964, XP_858921, XP_858886, and XP_858843. Sema6A polypeptides and the variants can be found in other animals.

The Sema6A functional domain designations may be defined as follows:

TABLE 1

Example Sema6A domains for human.

| Domain | Sema6A (isoform A) 1030aa | Sema6A (isoform B) 1047aa | Sema6A (isoform C) 971aa | Sema6A (isoform D) 975aa |
|---|---|---|---|---|
| Signal Seq. | 1-18 | 1-18 | 1-18 | 1-18 |
| Sema Domain | 56-472 | 56-472 | 56-418 | 56-472 |
| PSI Domain | 514-551 | 514-551 | 456-492 | 514-551 |
| Transmembrane | 650-670 | 667-687 | 591-611 | 595-615 |
| Cytoplasmic | 671-1030 | 688-1047 | 612-971 | 616-975 |

TABLE 2

Example Sema6A domains for mice.

| Domain | Sema6A (isoform 1) 1031aa | Sema6A (isoform 2) 1005aa | Sema6A (isoform 3) 976aa |
|---|---|---|---|
| Signal Seq. | 1-18 | 1-18 | 1-18 |
| Sema Domain | 56-474 | 56-448 | 56-474 |
| PSI Domain | 514-547 | 488-521 | 514-547 |
| Transmembrane | 650-670 | 624-644 | 595-615 |
| Cytoplasmic | 671-1031 | 645-1005 | 616-976 |

As one of skill in the art will appreciate, the beginning and ending residues of the domains listed above may vary depending upon the computer modeling program used or the method used for determining the domain. As such, various functional domains of Sema6A may vary from those defined above. For example, the functional domains of human Sema6A polypeptide isoform A, i.e., SEQ ID NO: 2, can vary as follows:

TABLE 3

Sequence Variations of Functional Domains of SEQ ID NO: 2.

| | Signal Seq. | Sema Domain | PSI Domain | Transmembrane domain | Cytoplasmic domain | Low complexity Region |
|---|---|---|---|---|---|---|
| SMART | 1-18 | 56-487 | 514-569 | 648-670 | 671-1030 | 937-952 |
| PROSITE | n/a | 24-512 | n/a | n/a | n/a | n/a |
| pFam | n/a | 56-491 | 514-565 | n/a | n/a | n/a |
| UniPort/Swiss Port | 1-18 | 24-512 | n/a | 650-670 | 671-1030 | n/a |
| NCBI (NP 065847) | n/a | 56-472 | 514-551 | n/a | n/a | n/a |
| Klostermann et al. | 5-20 | 42-564 | n/a | 648-671 | 671-1030 | n/a |

Based on the sequence variation in SEQ ID NO: 2, a person of ordinary skill in the art can identify sequence variations in SEQ ID NOs: 4, 6, and 8.

The sequences of the functional domains in SEQ ID NO: 10, i.e., isoform 1 of the mouse Sema6A polypeptide sequence, vary as follows:

TABLE 4

Sequence Variations of Functional Domains of SEQ ID NO: 10

|  | Signal Seq. | Sema Domain | PSI Domain | Transmembrane domain | Cytoplasmic domain | Low complexity Region |
|---|---|---|---|---|---|---|
| SMART | 1-18 | 56-487 | 514-569 | 648-670 | 671-1031 | 937-951 |
| PROSITE | n/a | 24-512 | n/a | n/a | n/a | n/a |
| pFam | n/a | 56-491 | 514-569 | n/a | n/a | n/a |
| UniProtKB/ Swiss Prot | 1-18 | 24-512 | n/a | 650-670 | 671-1031 | n/a |
| NCBI (NP 061214) | n/a | 56-474 | 514-547 | n/a | n/a | n/a |

In addition, the sequence variations in SEQ ID NOs: 12 or 14 or any other variants in mouse or other animals can readily be identified based on Tables 2-4.

Plexin-A2

The plexin-A2 polypeptide is known to bind to Sema6A polypeptide. Suto et al. *Neuron* 53: 535 (2007). The fall-length human plexin-A2 polypeptide (SEQ ID NO: 15) consists of a signal sequence, an extracellular domain, a transmembrane domain and a cytoplasmic domain. The extracellular domain comprises a sema domain and four IPT/TIG domains, i.e., IPT/TIGs 1-4. The sema domain is amino acids 50-523 of SEQ ID NO: 15. The IPT/TIG domains 1-4 are amino acids 873-967, 967-1053, 1056-1155, and 1158-1251 of SEQ ID NO: 15, respectively. As one of skill in the art will appreciate, the beginning and ending residues of the domains listed above may vary depending upon the computer modeling program used or the method used for determining the domain.

The sequences of full-length human plexin-A2 polypeptides vary. One example of a plexin-A2 polypeptide variant has 1894 aa sequence and has the accession number NP 079455 in Genbank. Also, plexin-A2 sequences from other animals are well known in the art. For example, mouse plexin-A2 polypeptides are known in the art and reported as NP_032908, AAH68155, EDL12938, EDL12937, and NP_786926 in Genbank.

Plexin-A4

Plexin-A4 is also known to be a receptor of Sema6A polypeptide. Suto et al. *Neuron* 53: 535 (2007). The full length human plexin-A4 polypeptide (SEQ ID NO: 16) consists of a signal sequence, an extracellular domain, a transmembrane domain and a cytoplasmic domain. The extracellular domain comprises a sema domain, three PSI domains, i.e., PSIs 1-3, and four IPT/TIG domains, i.e., IPT/TIGs 1-4. The sema domain is amino acids 24-507 of SEQ ID NO: 16. PSI domains 1-3 are amino acids 509-559, 655-702, and 803-856 of SEQ ID NO: 16, respectively. IPT/TIG domains 1-4 of the plexin-A4 polypeptide are amino acids 858-952, 954-1037, 1040-1139, and 1142-1230 of SEQ ID NO: 16, respectively. An artisan appreciates that the beginning and ending residues of the domains listed above may vary depending upon the computer modeling program used or the method used for determining the domain.

Sequences of full-length human plexin-A4 polypeptides vary. For example, several variants of plexin-A4 are reported as EAW83796, NP_001099013, EAW83795, AAH28744, and EAL24077 in Genbank. Furthermore, plexin-A4 sequences from other animals are also reported. For example, mouse plexin-A4 polypeptides are known as NP_786926, BAC56599, EDL13705, and EDL13704 in Genbank.

Some embodiments of the invention provide a full-length or mature Sema6A polypeptide or a soluble Sema6A polypeptide. Specifically, soluble Sema6A polypeptides of the present invention include fragments, variants, or derivatives thereof of a full-length or mature Sema6A polypeptide. Tables 1-4 above describe the various functional domains of the Sema6A polypeptide. Soluble Sema6A polypeptides of the invention generally comprise a portion or all of the extracellular domain of the polypeptides. Soluble Sema6A polypeptides generally lack the transmembrane domain and/or cytoplasmic domains. As one of skill in the art would appreciate, the entire extracellular domain of Sema6A may comprise additional or fewer amino acids on either the C-terminal or N-terminal end of the extracellular domain polypeptide, and may contain internal deletions.

Human Sema6A polypeptides for use in the methods of the present invention include, but are not limited to, a Sema6A polypeptide comprising, consisting essentially of, or consisting of an amino acid sequence at least 60%, 70%, 80%, 85%, 90%, 95%, 99% or 100% identical to a reference amino acid sequence, wherein said reference amino acid sequence is selected from the group consisting of amino acids 56 to 417 of SEQ ID NO: 2; a to 417 of SEQ ID NO:2; b to 417 of SEQ ID NO:2; 1 to 417 of SEQ ID NO:2; 56 to c of SEQ ID NO: 2; a to c of SEQ ID NO: 2; b to c of SEQ ID NO: 2; 1 to c of SEQ ID NO: 2; 56 to c' of SEQ ID NO: 6; a to c' of SEQ NO: 6; b to c' of SEQ ID NO: 6; 1 to c' of SEQ ID NO: 6; 56 to d of SEQ ID NO: 2; a to d of SEQ ID NO: 2; b to d of SEQ ID NO: 2; 1 to d of SEQ ID NO: 2; 56 to d' of SEQ ID NO: 6; a to d' of SEQ ID NO: 6; b to d' of SEQ ID NO: 6; 1 to d' of SEQ ID NO: 6; 56 to e of SEQ ID NO: 2; a to e of SEQ ID NO: 2; b to e of SEQ ID NO: 2; 1 to e of SEQ ID NO: 2; 56 to e' of SEQ ID NO: 6; a to e' of SEQ ID NO: 6; b to e' of SEQ ID NO: 6; 1 to e' of SEQ ID NO: 6; 56 to e" of SEQ ID NO: 8; a to e" of SEQ ID NO: 8; b to e" of SEQ ID NO: 8; 1 to e" of SEQ ID NO: 8; 56 to e'" of SEQ ID NO: 4; a to e'" of SEQ ID NO: 4; b to e'" of SEQ ID NO: 6; 1 to e'" of SEQ ID NO: 8; 56 to f of SEQ ID NO: 2; a to f of SEQ ID NO: 2; b to f of SEQ ID NO: 2; 1 to f of SEQ ID NO: 2; 56 to f' of SEQ ID NO: 6; a to f' of SEQ ID NO: 6; b to f' of SEQ ID NO: 6; 1 to f' of SEQ ID NO: 6; 56 to f" of SEQ ID NO: 8; a to f" of SEQ ID NO: 8; b to f" of SEQ ID NO: 8; 1 to f" of SEQ ID NO: 8; 56 to f'" of SEQ ID NO: 4; a to f'" of SEQ ID NO: 4; b to f'" of SEQ ID NO: 4; 1 to f'" of SEQ ID NO: 4; and a combination of two or more of said amino acid sequences; wherein a is any integer between 24 and 56, b is any integer between 19 and 21, c is any integer between 472 and 512, c' is any integer between 418 and 453, d is any integer between 514 and 569, d' is any integer between 455 and 510, e is any integer between 570 and 650, e' is any integer between 511 and 591, e" is any integer between 570 and 595, and e'" is any integer between 570 and 667; f is any integer between 647 and 671, f' is any integer between 588 and 612, f" is any integer between 592-616, and f'" is any integer between 664 and 688. In certain embodiments, the Sema6A polypeptide for use in the methods of the present invention binds to a plexin-A2 or to a plexin-A4 polypeptide.

In certain embodiments, human Sema6A polypeptides for use in the methods of the present invention include a Sema6A polypeptide comprising, consisting essentially of, or consisting of an amino acid sequence at least 60%, 70%, 80%, 85%, 90%, 95%, 99% or 100% identical to a reference amino acid sequence, wherein the reference amino acid sequence is selected from the group consisting of amino acids 1 to 975 of SEQ ID NO: 8; 19 to 417 of SEQ ID NO: 2; 19 to 472 of SEQ ID NO: 2; 19 to 551 of SEQ ID NO: 2; 19 to 492 of SEQ ID NO: 6; 19 to 647 of SEQ ID NO:2; 19 to 588 of SEQ ID NO: 6; 19 to 592 of SEQ ID NO: 8; 19 to 664 of SEQ ID NO: 4; 56 to 472 of SEQ ID NO: 2; 56 to 551 of SEQ ID NO: 2; 56 to 492 of SEQ ID NO: 6; 56 to 647 of SEQ ID NO:2; 56 to 588 of SEQ ID NO: 6; 56 to 592 of SEQ ID NO: 8; 56 to 664 of SEQ ID NO: 4; 1 to 649 of SEQ ID NO: 2; [human Sema6A-Fc from R&D] 1 to 590 of SEQ ID NO: 6; 1 to 594 of SEQ ID NO: 8; 1 to 666 of SEQ ID NO: 4; 18 to 703 of SEQ ID NO: 2; 18 to 644 of SEQ ID NO: 6; 18 to 648 of SEQ ID NO: 8; 18 to 720 of SEQ ID NO: 4; 1 to 648 of SEQ ID NO: 2; 1 to 589 of SEQ ID NO: 6; 1 to 593 of SEQ ID NO: 8; 1 to 665 of SEQ ID NO: 4; and a combination of two or more of said amino acid sequences. In another embodiments, the Sema6A polypeptide binds to plexin-A2 or plexin-A4 polypeptides.

In another embodiment, human Sema6A polypeptides for use in the methods of the present invention include a Sema6A polypeptide comprising, consisting essentially of, or consisting of an amino acid sequence at least 60%, 70%, 80%, 85%, 90%, 95%, 99% or 100% identical to a reference amino acid sequence, wherein the reference amino acid sequence is selected from the group consisting of amino acids 56-417 of SEQ ID NO: 2; 55-417 of SEQ ID NO: 2; 54-417 of SEQ ID NO: 2; 53-417 of SEQ ID NO: 2; 52-417 of SEQ ID NO: 2; 51-417 of SEQ ID NO: 2; 50-417 of SEQ ID NO: 2; 49-417 of SEQ ID NO: 2; 48-417 of SEQ ID NO: 2; 47-417 of SEQ ID NO: 2; 46-417 of SEQ ID NO: 2; 45-417 of SEQ ID NO: 2; 44-417 of SEQ ID NO: 2; 43-417 of SEQ ID NO: 2; 42-417 of SEQ ID NO: 2; 41-417 of SEQ ID NO: 2; 40-417 of SEQ ID NO: 2; 39-417 of SEQ ID NO: 2; 38-417 of SEQ ID NO: 2; 37-417 of SEQ ID NO: 2; 36-417 of SEQ ID NO: 2; 35-417 of SEQ ID NO: 2; 34-417 of SEQ ID NO: 2; 33-417 of SEQ ID NO: 2; 32-417 of SEQ ID NO: 2; 31-417 of SEQ ID NO: 2; 30-417 of SEQ ID NO: 2; 29-417 of SEQ ID NO: 2; 28-417 of SEQ ID NO: 2; 27-417 of SEQ ID NO: 2; 26-417 of SEQ ID NO: 2; 25-417 of SEQ ID NO: 2; 24-417 of SEQ ID NO: 2; 23-417 of SEQ ID NO: 2; 22-417 of SEQ ID NO: 2; 21-417 of SEQ ID NO: 2; 20-417 of SEQ ID NO: 2; 19-417 of SEQ ID NO: 2; 18-417 of SEQ ID NO: 2; 17-417 of SEQ ID NO: 2; 16-417 of SEQ ID NO: 2; 15-417 of SEQ ID NO: 2; 14-417 of SEQ ID NO: 2; 13-417 of SEQ ID NO: 2; 12-417 of SEQ ID NO: 2; 11-417 of SEQ ID NO: 2; 10-417 of SEQ ID NO: 2; 9-417 of SEQ ID NO: 2; 8-417 of SEQ ID NO: 2; 7-417 of SEQ ID NO: 2; 6-417 of SEQ ID NO: 2; 5-417 of SEQ ID NO: 2; 4-417 of SEQ ID NO: 2; 3-417 of SEQ ID NO: 2; 2-417 of SEQ ID NO: 2; 1-417 of SEQ ID NO: 2; and a combination of two or more of said amino acid sequences, wherein said Sema6A polypeptide binds to plexin-A2 polypeptides.

Further embodiments include human Sema6A polypeptides for use in the methods of the present invention include a Sema6A polypeptide comprising, consisting essentially of, or consisting of an amino acid sequence at least 60%, 70%, 80%, 85%, 90%, 95%, 99% or 100% identical to a reference amino acid sequence, wherein said reference amino acid sequence is selected from the group consisting of amino acids 40-472 of SEQ ID NO: 2; 41-472 of SEQ ID NO: 2; 42-472 of SEQ ID NO: 2; 43-472 of SEQ ID NO: 2; 44-472 of SEQ ID NO: 2; 45-472 of SEQ ID NO: 2; 46-472 of SEQ ID NO: 2; 47-472 of SEQ ID NO: 2; 48-472 of SEQ ID NO: 2; 49-472 of SEQ ID NO: 2; 50-472 of SEQ ID NO: 2; 51-472 of SEQ ID NO: 2; 52-472 of SEQ ID NO: 2; 53-472 of SEQ ID NO: 2; 54-472 of SEQ ID NO: 2; 55-472 of SEQ ID NO: 2; 56-472 of SEQ ID NO: 2; 57-472 of SEQ ID NO: 2; 58-472 of SEQ ID NO: 2; 59-472 of SEQ ID NO: 2; 60-472 of SEQ ID NO: 2; 56-465 of SEQ ID NO: 2; 56-466 of SEQ ID NO: 2; 56-467 of SEQ ID NO: 2; 56-468 of SEQ ID NO: 2; 56-469 of SEQ ID NO: 2; 56-470 of SEQ ID NO: 2; 56-471 of SEQ ID NO: 2; 56-472 of SEQ ID NO: 2; 56-473 of SEQ ID NO: 2; 56-474 of SEQ ID NO: 2; 56-475 of SEQ ID NO: 2; 56-476 of SEQ ID NO: 2; 56-477 of SEQ ID NO: 2; 56-478 of SEQ ID NO: 2; 56-479 of SEQ ID NO: 2; 56-480 of SEQ ID NO: 2; and a combination of two or more of said amino acid sequences.

Further embodiments include human Sema6A polypeptides for use in the methods of the present invention include a Sema6A polypeptide comprising, consisting essentially of, or consisting of an amino acid sequence at least 60%, 70%, 80%, 85%, 90%, 95%, 99% or 100% identical to a reference amino acid sequence, wherein the reference amino acid sequence is selected from the group consisting of amino acids 1-551 of SEQ ID NO: 2; 1-552 of SEQ ID NO: 2; 1-553 of SEQ ID NO: 2; 1-554 of SEQ ID NO: 2; 1-555 of SEQ ID NO: 2; 1-556 of SEQ ID NO: 2; 1-557 of SEQ ID NO: 2; 1-558 of SEQ ID NO: 2; 1-559 of SEQ ID NO: 2; 1-560 of SEQ ID NO: 2; 1-561 of SEQ ID NO: 2; 1-562 of SEQ ID NO: 2; 1-563 of SEQ ID NO: 2; 1-564 of SEQ ID NO: 2; 1-565 of SEQ ID NO: 2; 1-566 of SEQ ID NO: 2; 1-567 of SEQ ID NO: 2; 1-568 of SEQ ID NO: 2; 1-569 of SEQ ID NO: 2; 1-570 of SEQ ID NO: 2; 1-571 of SEQ ID NO: 2; 1-571 of SEQ ID NO: 2; 1-572 of SEQ ID NO: 2; 1-573 of SEQ ID NO: 2; 1-574 of SEQ ID NO: 2; 1-575 of SEQ ID NO: 2; 1-576 of SEQ ID NO: 2; 1-577 of SEQ ID NO: 2; 1-578 of SEQ ID NO: 2; 1-579 of SEQ ID NO: 2; 1-580 of SEQ ID NO: 2; 1-581 of SEQ ID NO: 2; 1-582 of SEQ ID NO: 2; 1-583 of SEQ ID NO: 2; 1-584 of SEQ ID NO: 2; 1-585 of SEQ ID NO: 2; 1-586 of SEQ ID NO: 2; 1-587 of SEQ ID NO: 2; 1-588 of SEQ ID NO: 2; 1-589 of SEQ ID NO: 2; 1-590 of SEQ ID NO: 2; 1-591 of SEQ ID NO: 2; 1-592 of SEQ ID NO: 2; 1-593 of SEQ ID NO: 2; 1-594 of SEQ ID NO: 2; 1-596 of SEQ ID NO: 2; 1-597 of SEQ ID NO: 2; 1-598 of SEQ ID NO: 2; 1-599 of SEQ ID NO: 2; 1-600 of SEQ ID NO: 2; and a combination of two or more of said amino acid sequences.

In other embodiments, human Sema6A polypeptides for use in the methods of the present invention include a Sema6A polypeptide comprising, consisting essentially of, or consisting of an amino acid sequence at least 60%, 70%, 80%, 85%, 90%, 95%, 99% or 100% identical to a reference amino acid sequence, wherein the reference amino acid sequence is selected from the group consisting of amino acids 1-649 of SEQ ID NO: 2; 2-649 of SEQ ID NO: 2; 3-649 of −649 of SEQ ID NO: 2; 4-649 of SEQ ID NO: 2; 5-649 of SEQ ID NO: 2; 6-649 of SEQ ID NO: 2; 7-649 of SEQ ID NO: 2; 8-649 of SEQ ID NO: 2; 9-649 of SEQ ID NO: 2; 10-649 of SEQ ID NO: 2; 11-649 of SEQ ID NO: 2; 12-649 of SEQ ID NO: 2;

13-649 of SEQ ID NO: 2; 14-649 of SEQ ID NO: 2; 15-649 of SEQ ID NO: 2; 16-649 of SEQ ID NO: 2; 17-649 of SEQ ID NO: 2; 18-649 of SEQ ID NO: 2; 19-649 of SEQ ID NO: 2; 20-649 of SEQ ID NO: 2; 21-649 of SEQ ID NO: 2; 22-649 of SEQ ID NO: 2; 23-649 of SEQ ID NO: 2; 24-649 of SEQ ID NO: 2; 25-649 of SEQ ID NO: 2; 26-649 of SEQ ID NO: 2; and a combination of two or more of said amino acid sequences.

The methods of the present invention further include a Sema6A polypeptide comprising, consisting essentially of, or consisting of an amino acid sequence at least 60%, 70%, 80%, 85%, 90%, 95%, 99% or 100% identical to a reference amino acid sequence, wherein the reference amino acid sequence is selected from the group consisting of amino acids 1-640 of SEQ ID NO: 2; 1-641 of SEQ ID NO: 2; 1-642 of SEQ ID NO: 2; 1-643 of SEQ ID NO: 2; 1-644 of SEQ ID NO: 2; 1-645 of SEQ ID NO: 2; 1-646 of SEQ ID NO: 2; 1-647 of SEQ ID NO: 2; 1-648 of SEQ ID NO: 2; 1-649 of SEQ ID NO: 2; 1-650 of SEQ ID NO: 2; 1-651 of SEQ ID NO: 2; 1-652 of SEQ ID NO: 2; 1-653 of SEQ ID NO: 2; 1-654 of SEQ ID NO: 2; 1-655 of SEQ ID NO: 2; 1-656 of SEQ ID NO: 2; 1-657 of SEQ ID NO: 2; 1-658 of SEQ ID NO: 2; 1-659 of SEQ ID NO: 2; 1-660 of SEQ ID NO: 2; 1-661 of SEQ ID NO: 2; 1-662 of SEQ ID NO: 2; 1-663 of SEQ ID NO: 2; 1-664 of SEQ ID NO: 2; 1-665 of SEQ ID NO: 2; 1-666 of SEQ ID NO: 2; 1-667 of SEQ ID NO: 2; 1-668 of SEQ ID NO: 2; 1-669 of SEQ ID NO: 2; 1-670 of SEQ ID NO: 2; and a combination of two or more of said amino acid sequences.

The methods of the present invention further include a Sema6A polypeptide comprising, consisting essentially of, or consisting of an amino acid sequence at least 60%, 70%, 80%, 85%, 90%, 95%, 99% or 100% identical to a reference amino acid sequence, wherein the reference amino acid sequence is selected from the group consisting of amino acids 1-570 of SEQ ID NO: 4; 1-571 of SEQ ID NO: 4; 1-572 of SEQ ID NO: 4; 1-573 of SEQ ID NO: 4; 1-574 of SEQ ID NO: 4; 1-575 of SEQ ID NO: 4; 1-576 of SEQ ID NO: 4; 1-577 of SEQ ID NO: 4; 1-578 of SEQ ID NO: 4; 1-579 of SEQ ID NO: 4; 1-580 of SEQ ID NO: 4; 1-581 of SEQ ID NO: 4; 1-582 of SEQ ID NO: 4; 1-583 of SEQ ID NO: 4; 1-584 of SEQ ID NO: 4; 1-585 of SEQ ID NO: 4; 1-586 of SEQ ID NO: 4; 1-587 of SEQ ID NO: 4; 1-588 of SEQ ID NO: 4; 1-589 of SEQ ID NO: 4; 1-590 of SEQ ID NO: 4; and a combination of two or more of said amino acid sequences.

The methods of the present invention further include a Sema6A polypeptide comprising, consisting essentially of, or consisting of an amino acid sequence at least 60%, 70%, 80%, 85%, 90%, 95%, 99% or 100% identical to a reference amino acid sequence, wherein the reference amino acid sequence is selected from the group consisting of amino acids 1-630 of SEQ ID NO: 4; 1-631 of SEQ ID NO: 4; 1-632 of SEQ ID NO: 4; 1-633 of SEQ ID NO: 4; 1-634 of SEQ ID NO: 4; 1-635 of SEQ ID NO: 4; 1-636 of SEQ ID NO: 4; 1-637 of SEQ ID NO: 4; 1-638 of SEQ ID NO: 4; 1-639 of SEQ ID NO: 4; 1-640 of SEQ ID NO: 4; 1-641 of SEQ ID NO: 4; 1-642 of SEQ ID NO: 4; 1-643 of SEQ ID NO: 4; 1-644 of SEQ ID NO: 4; 1-645 of SEQ ID NO: 4; 1-646 of SEQ ID NO: 4; 1-647 of SEQ ID NO: 4; 1-648 of SEQ ID NO: 4; 1-649 of SEQ ID NO: 4; 1-650 of SEQ ID NO: 4; 1-651 of SEQ ID NO: 4; 1-652 of SEQ ID NO: 4; 1-653 of SEQ ID NO: 4; 1-654 of SEQ ID NO: 4; 1-655 of SEQ ID NO: 4; 1-656 of SEQ ID NO: 4; 1-657 of SEQ ID NO: 4; 1-658 of SEQ ID NO: 4; 1-659 of SEQ ID NO: 4; 1-660 of SEQ ID NO: 4; 1-661 of SEQ ID NO: 4; 1-662 of SEQ ID NO: 4; 1-663 of SEQ ID NO: 4; 1-664 of SEQ ID NO: 4; 1-665 of SEQ ID NO: 4; 1-666 of SEQ ID NO: 4; and a combination of two or more of said amino acid sequences.

The methods of the present invention further include a Sema6A polypeptide comprising, consisting essentially of, or consisting of an amino acid sequence at least 60%, 70%, 80%, 85%, 90%, 95%, 99% or 100% identical to a reference amino acid sequence, wherein the reference amino acid sequence is selected from the group consisting of amino acids 45-492 of SEQ ID NO: 6; 46-492 of SEQ ID NO: 6; 47-492 of SEQ ID NO: 6; 48-492 of SEQ ID NO: 6; 49-492 of SEQ ID NO: 6; 50-492 of SEQ ID NO: 6; 51-492 of SEQ ID NO: 6; 52-492 of SEQ ID NO: 6; 53-492 of SEQ ID NO: 6; 54-492 of SEQ ID NO: 6; 55-492 of SEQ ID NO: 6; 56-492 of SEQ ID NO: 6; 57-492 of SEQ ID NO: 6; 58-492 of SEQ ID NO: 6; 59-492 of SEQ ID NO: 6; 60-492 of SEQ ID NO: 6; 61-492 of SEQ ID NO: 6; 56-485 of SEQ ID NO: 6; 56-486 of SEQ ID NO: 6; 56-487 of SEQ ID NO: 6; 56-488 of SEQ ID NO: 6; 56-489 of SEQ ID NO: 6; 56-490 of SEQ ID NO: 6; 56-491 of SEQ ID NO: 6; 56-492 of SEQ ID NO: 6; 56-493 of SEQ ID NO: 6; 56-494 of SEQ ID NO: 6; 56-495 of SEQ ID NO: 6; 56-496 of SEQ ID NO: 6; 56-497 of SEQ ID NO: 6; 56-498 of SEQ ID NO: 6; 56-599 of SEQ ID NO: 6; and a combination of two or more of said amino acid sequences.

The methods of the present invention further include a Sema6A polypeptide comprising, consisting essentially of, or consisting of an amino acid sequence at least 60%, 70%, 80%, 85%, 90%, 95%, 99% or 100% identical to a reference amino acid sequence, wherein the reference amino acid sequence is selected from the group consisting of amino acids 1-580 of SEQ ID NO: 6; 1-581 of SEQ ID NO: 6; 1-583 of SEQ ID NO: 6; 1-584 of SEQ ID NO: 6; 1-585 of SEQ ID NO: 6; 1-586 of SEQ ID NO: 6; 1-587 of SEQ ID NO: 6; 1-588 of SEQ ID NO: 6; 1-589 of SEQ ID NO: 6; 1-590 of SEQ ID NO: 6; 1-591 of SEQ ID NO: 6; 1-592 of SEQ ID NO: 6; 1-593 of SEQ ID NO: 6; 1-594 of SEQ ID NO: 6; 1-595 of SEQ ID NO: 6; 1-596 of SEQ ID NO: 6; 1-597 of SEQ ID NO: 6; 1-598 of SEQ ID NO: 6; 1-599 of SEQ ID NO: 6; 1-600 of SEQ ID NO: 6; 2-590 of SEQ ID NO: 6; 3-590 of SEQ ID NO: 6; 4-590 of SEQ ID NO: 6; 5-590 of SEQ ID NO: 6; 6-590 of SEQ ID NO: 6; 7-590 of SEQ ID NO: 6; 8-590 of SEQ ID NO: 6; 9-590 of SEQ ID NO: 6; 10-590 of SEQ ID NO: 6; 11-590 of SEQ ID NO: 6; 12-590 of SEQ ID NO: 6; 13-590 of SEQ ID NO: 6; 14-590 of SEQ ID NO: 6; 15-590 of SEQ ID NO: 6; 16-590 of SEQ ID NO: 6; 17-590 of SEQ ID NO: 6; 18-590 of SEQ ID NO: 6; 19-590 of SEQ ID NO: 6; and a combination of two or more of said amino acid sequences.

The methods of the present invention further include a Sema6A polypeptide comprising, consisting essentially of, or consisting of an amino acid sequence at least 60%, 70%, 80%, 85%, 90%, 95%, 99% or 100% identical to a reference amino acid sequence, wherein said reference amino acid sequence is selected from the group consisting of amino acids 56-580 of SEQ ID NO: 8; 56-581 of SEQ ID NO: 8; 56-583 of SEQ ID NO: 8; 56-584 of SEQ ID NO: 8; 56-585 of SEQ ID NO: 8; 56-586 of SEQ ID NO: 8; 56-587 of SEQ ID NO: 8; 56-588 of SEQ ID NO: 8; 56-589 of SEQ ID NO: 8; 56-590 of SEQ ID NO: 8; 56-591 of SEQ ID NO: 8; 56-592 of SEQ ID NO: 8; 56-593 of SEQ ID NO: 8; 56-594 of SEQ ID NO: 8; 56-595 of SEQ ID NO: 8; 56-596 of SEQ ID NO: 8; 56-597 of SEQ ID NO: 8; 56-598 of SEQ ID NO: 8; 56-599 of SEQ ID NO: 8; 56-600 of SEQ ID NO: 8; 56-601 of SEQ ID NO: 8; 56-602 of SEQ ID NO: 8; 56-603 of SEQ ID NO: 8; 56-604 of SEQ ID NO: 8; 56-605 of SEQ ID NO: 8; 45-595 of SEQ ID NO: 8; 46-595 of SEQ ID NO: 8; 47-595 of SEQ ID NO: 8; 48-595 of SEQ ID NO: 8; 49-595 of SEQ ID NO: 8; 50-595 of SEQ ID NO: 8; 51-595 of SEQ ID NO: 8; 52-595 of SEQ ID NO: 8; 53-595 of SEQ ID NO: 8; 54-595 of SEQ ID NO: 8; 55-595 of SEQ ID NO: 8; and a combination of two or more of said amino acid sequences.

The methods of the present invention further include a Sema6A polypeptide comprising, consisting essentially of, or consisting of an amino acid sequence at least 60%, 70%, 80%, 85%, 90%, 95%, 99% or 100% identical to a reference amino acid sequence, wherein the reference amino acid sequence is selected from the group consisting of amino acids 1-580 of SEQ ID NO: 8; 1-581 of SEQ ID NO: 8; 1-583 of SEQ ID NO: 8; 1-584 of SEQ ID NO: 8; 1-585 of SEQ ID NO: 8; 1-586 of SEQ ID NO: 8; 1-587 of SEQ ID NO: 8; 1-588 of SEQ ID NO: 8; 1-589 of SEQ ID NO: 8; 1-590 of SEQ ID NO: 8; 1-591 of SEQ ID NO: 8; 1-592 of SEQ ID NO: 8; 1-593 of SEQ ID NO: 8; 1-594 of SEQ ID NO: 8; 1-595 of SEQ ID NO: 8; 1-596 of SEQ ID NO: 8; 1-597 of SEQ ID NO: 8; 1-598 of SEQ ID NO: 8; 1-599 of SEQ ID NO: 8; 1-600 of SEQ ID NO: 8; 1-601 of SEQ ID NO: 8; 1-602 of SEQ ID NO: 8; 1-603 of SEQ ID NO: 8; 1-604 of SEQ ID NO: 8; 1-605 of SEQ ID NO: 8; 2-595 of SEQ ID NO: 8; 3-595 of SEQ ID NO: 8; 4-595 of SEQ ID NO: 8; 5-595 of SEQ ID NO: 8; 6-595 of SEQ ID NO: 8; 7-595 of SEQ ID NO: 8; 8-595 of SEQ ID NO: 8; 9-595 of SEQ ID NO: 8; 10-595 of SEQ ID NO: 8; 11-595 of SEQ ID NO: 8; 12-595 of SEQ ID NO: 8; 13-595 of SEQ ID NO: 8; 14-595 of SEQ ID NO: 8; 15-595 of SEQ ID NO: 8; 16-595 of SEQ ID NO: 8; 17-595 of SEQ ID NO: 8; 18-595 of SEQ ID NO: 8; 19-595 of SEQ ID NO: 8; and a combination of two or more of said amino acid sequences.

In certain embodiments, the Sema6A polypeptide of the present invention binds to plexin-A subfamily polypeptides. For example, the Sema6A polypeptide binds to a plexin-A1 polypeptide, a plexin-A2 polypeptide, a plexin-A3 polypeptide or a plexin-A4 polypeptide. In other embodiments, the Sema6A polypeptide may be isolated.

By "a reference amino acid sequence" is meant the specified sequence without the introduction of any amino acid substitutions. As one of ordinary skill in the art would understand, if there are no substitutions, the "isolated polypeptide" of the invention comprises an amino acid sequence which is identical to the reference amino acid sequence.

Sema6A polypeptides described herein may have various alterations such as substitutions, insertions or deletions. Exemplary amino acids that can be substituted in the polypeptide include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

Corresponding fragments of Sema6A polypeptides at least 70%, 75%, 80%, 85%, 90%, or 95% identical to the polypeptides and reference polypeptides described herein are also contemplated.

As known in the art, "sequence identity" between two polypeptides is determined by comparing the amino acid sequence of one polypeptide to the sequence of a second polypeptide. When discussed herein, whether any particular polypeptide is at least about 70%, 75%, 80%, 85%, 90%, 95%, 99%, or 100% identical to another polypeptide can be determined using methods and computer programs/software known in the art such as, but not limited to, the BESTFIT program (Wisconsin Sequence Analysis Package, Version 8 for Unix, Genetics Computer Group, University Research Park, 575 Science Drive, Madison, Wis. 53711). BESTFIT uses the local homology algorithm of Smith and Waterman, Advances in Applied Mathematics 2:482-489 (1981), to find the best segment of homology between two sequences. When using BESTFIT or any other sequence alignment program to determine whether a particular sequence is, for example, 95% identical to a reference sequence according to the present invention, the parameters are set, of course, such that the percentage of identity is calculated over the full length of the reference polypeptide sequence and that gaps in homology of up to 5% of the total number of amino acids in the reference sequence are allowed.

In methods of the present invention, a Sema6A polypeptide or polypeptide fragment of the invention may be administered directly as a preformed polypeptide. As discussed elsewhere herein, a Sema6A polypeptide may also be administered as a polynucleotide to be taken up by cells and expressed therein. For example, a polynucleotide encoding Sema6A may be administered as a viral vector.

Treatment Methods Using Sema6A Polypeptides

One embodiment of the present invention provides methods for treating a disease, disorder or injury associated with dysmyelination or demyelination, e.g., multiple sclerosis, in an animal suffering from such disease, the method comprising, consisting essentially of, or consisting of administering to the animal an effective amount of a Sema6A polypeptide or fragment thereof, a soluble Sema6A polypeptide, or variants, derivatives or analogs thereof.

Additionally, the invention is directed to a method for promoting myelination of neurons in a mammal comprising, consisting essentially of, or consisting of administering a therapeutically effective amount of a Sema6A polypeptide or a fragment thereof, a soluble Sema6A polypeptide, and variants, derivatives, or analogs thereof.

An additional embodiment of the present invention provides methods for treating a disease, disorder or injury associated with oligodendrocyte death or lack of differentiation, e.g., multiple sclerosis, Pelizaeus Merzbacher disease or globoid cell leukodystrophy (Krabbe's disease), in an animal suffering from such disease, the method comprising, consisting essentially of, or consisting of administering to the animal an effective amount of a Sema6A polypeptide or a fragment thereof, a soluble Sema6A polypeptide, and variants, derivatives, or analogs thereof.

Another aspect of the invention includes a method for promoting proliferation, differentiation and survival of oligodendrocytes in a mammal comprising, consisting essentially of, or consisting of administering a therapeutically effective amount of a Sema6A polypeptide or a fragment thereof, a soluble Sema6A polypeptide, and variants, derivatives, or analogs thereof.

The present invention is directed to a method for promoting proliferation, differentiation, or survival of oligodendrocytes, comprising contacting the oligodendrocytes with an effective amount of a composition comprising a Sema6A polypeptide. The present invention is further directed to a method for promoting oligodendrocyte-mediated myelination of neurons, comprising contacting a mixture of neurons and oligodendrocytes with an effective amount of a composition comprising an isolated Sema6A polypeptide.

A Sema6A polypeptide to be used in treatment methods disclosed herein, can be prepared and used as a therapeutic agent that induce, promote, activate, or stimulate the ability of Sema6A to regulate myelination of neurons by oligodendrocytes. Additionally, the Sema6A polypeptide to be used in treatment methods disclosed herein can be prepared and used as a therapeutic agent that induces, promotes, activates, or stimulates the ability of Sema6A to regulate oligodendrocyte differentiation, proliferation and survival.

Further embodiments of the invention include a method of inducing oligodendrocyte proliferation or survival to, treat a disease, disorder or injury involving the destruction of oligodendrocytes or myelin comprising administering to a mammal, at or near the site of the disease, disorder or injury, in an amount sufficient to reduce inhibition of axonal extension and promote myelination.

In another embodiment, the invention is directed to a method for promoting proliferation, differentiation, or survival of oligodendrocytes in a mammal, comprising administering to a mammal in need thereof an effective amount of a composition comprising an isolated polynucleotide which encodes a Sema6A polypeptide disclosed herein or a method for promoting myelination of neurons in a mammal, comprising administering to a mammal thereof an effective amount of a composition comprising an isolated polynucleotide, which encodes a Sema6A polypeptide disclosed herein.

The invention also includes a method for treating a disease, disorder, or injury associated with destruction of myelin or dysmyelination or demyelination or a disease disorder, or injury associated with oligodendrocyte death or lack of differentiation in a mammal comprising administering to a mammal in need thereof a therapeutically effective amount of a composition comprising an isolated polynucleotide which encodes a Sema6A polypeptide.

In methods of the present invention, a Sema6A polypeptide can be administered via direct administration of a Sema6A polypeptide to the patient. Alternatively, the Sema6A polypeptide can be administered via an expression vector which produces the specific Sema6A polypeptide. In certain embodiments of the invention, a Sema6A polypeptide is administered in a treatment method that includes: (1) transforming or transfecting an implantable host cell with a nucleic acid, e.g., a vector, that expresses a Sema6A polypeptide; and (2) implanting the transformed host cell into a mammal, at the site of a disease, disorder or injury. For example, the transformed host cell can be implanted at the site of a chronic lesion of MS. In some embodiments of the invention, the implantable host cell is removed from a mammal, temporarily cultured, transformed or transfected with an isolated nucleic acid encoding a Sema6A polypeptide, and implanted back into the same mammal from which it was removed. The cell can be, but is not required to be, removed from the same site at which it is implanted. Such embodiments, sometimes known as ex vivo gene therapy, can provide a continuous supply of the Sema6A polypeptide, localized at the site of action, for a limited period of time.

Diseases or disorders which may be treated or ameliorated by the methods of the present invention include diseases, disorders or injuries which relate to dysmyelination or demyelination of mammalian neurons. Specifically, diseases and disorders in which the myelin which surrounds the neuron is either absent, incomplete, not formed properly or is deteriorating. Such diseases include, but are not limited to, multiple sclerosis (MS) including relapsing remitting, secondary progressive and primary progressive forms of MS; progressive multifocal leukoencephalopathy (PML), encephalomyelitis (EPL), central pontine myelolysis (CPM), adrenoleukodystrophy, Alexander's disease, Pelizaeus Merzbacher disease (PMZ), globoid cell leukodystrophy (Krabbe's disease), Wallerian Degeneration, optic neuritis and transvere myelitis.

Diseases or disorders which may be treated or ameliorated by the methods of the present invention include neurodegenerate disease or disorders. Such diseases include, but are not limited to, amyotrophic lateral sclerosis, Huntington's disease, Alzheimer's disease and Parkinson's disease.

Examples of additional diseases, disorders or injuries which may be treated or ameliorated by the methods of the present invention include, but are not limited to, spinal cord injuries, chronic myelopathy or rediculopathy, tramatic brain injury, motor neuron disease, axonal shearing, contusions, paralysis, post radiation damage or other neurological complications of chemotherapy, stroke, large lacunes, medium to large vessel occlusions, leukoariaosis, acute ischemic optic neuropathy, vitamin E deficiency (isolated deficiency syndrome, AR, Bassen-Kornzweig syndrome), B12, B6 (pyridoxine-pellagra), thiamine, folate, nicotinic acid deficiency, Marchiafava-Bignami syndrome, Metachromatic Leukodystrophy, Trigeminal neuralgia, Bell's palsy, or any neural injury which would require axonal regeneration, remyelination or oligodendrocyte survival or differentiation/proliferation.

Fusion Proteins and Conjugated Polypeptides

Some embodiments of the invention involve the use of a Sema6A polypeptide fused to a heterologous polypeptide moiety to form a fusion protein. Such fusion proteins can be used to accomplish various objectives, e.g., increased serum half-life, improved bioavailability, in vivo targeting to a specific organ or tissue type, improved recombinant expression efficiency, improved host cell secretion, ease of purification, and higher avidity. Depending on the objective(s) to be achieved, the heterologous moiety can be inert or biologically active. Also, it can be chosen to be stably fused to the Sema6A polypeptide moiety of the invention or to be cleavable, in vitro or in vivo. Heterologous moieties to accomplish these other objectives are known in the art.

As an alternative to expression of a fusion protein, a chosen heterologous moiety can be preformed and chemically conjugated to the Sema6A polypeptide moiety of the invention. In most cases, a chosen heterologous moiety will function similarly, whether fused or conjugated to the Sema6A polypeptide moiety. Therefore, in the following discussion of heterologous amino acid sequences, unless otherwise noted, it is to be understood that the heterologous sequence can be joined the Sema6A polypeptide moiety in the form of a fusion protein or as a chemical conjugate (including covalent and non-covalent conjugations) to polypeptides or other compositions. For example, Sema6A polypeptides may be recombinantly fused or conjugated to molecules useful as labels in detection assays and effector molecules such as heterologous polypeptides, drugs, radionuclides, or toxins. See, e.g., PCT publications WO 92/08495; WO 91/14438; WO 89/12624; U.S. Pat. No. 5,314,995; and EP 396,387.

Sema6A polypeptides for use in the treatment methods disclosed herein include derivatives that are modified, i.e., by the covalent attachment of any type of molecule such that covalent attachment does not prevent the Sema6A polypeptide from inhibiting the biological function of Sema6A. For example, but not by way of limitation, the Sema6A polypeptides of the present invention may be modified e.g., by glycosylation, acetylation, pegylation, phosphylation, phosphorylation, amidation, derivatization by known protecting/blocking groups, proteolytic cleavage, linkage to a cellular ligand or other protein, etc. Any of numerous chemical modifications may be carried out by known techniques, including, but not limited to specific chemical cleavage, acetylation, formylation, metabolic synthesis of tunicamycin, etc. Additionally, the derivative may contain one or more non-classical amino acids.

Sema6A polypeptides for use in the treatment methods disclosed herein can be composed of amino acids joined to each other by peptide bonds or modified peptide bonds, i.e., peptide isosteres, and may contain amino acids other than the 20 gene-encoded amino acids. Sema6A polypeptides may be modified by natural processes, such as posttranslational processing, or by chemical modification techniques which are well known in the art. Such modifications are well described in basic texts and in more detailed monographs, as well as in a voluminous research literature. Modifications can occur anywhere in the Sema6A polypeptide, including the peptide backbone, the amino acid side-chains and the amino or carboxyl termini, or on moieties such as carbohydrates. It will be appreciated that the same type of modification may be present in the same or varying degrees at several sites in a given Sema6A polypeptide. Also, a given Sema6A polypeptide may contain many types of modifications. Sema6A polypeptides may be branched, for example, as a result of ubiquitination, and they may be cyclic, with or without branching. Cyclic, branched, and branched cyclic Sema6A polypeptides may result from posttranslation natural processes or may be made by synthetic methods. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristoylation, oxidation, pegylation, proteolytic processing, phosphorylation, prenylation, racemization, selenoylation, sulfation, transfer-RNA mediated addition of amino acids to proteins such as arginylation, and ubiquitination. (See, for instance, *Proteins—Structure And Molecular Properties*, T. E. Creighton, W. H. Freeman and Company, New York 2nd Ed., (1993); *Posttranslational Covalent Modification Of Proteins*, B. C. Johnson, Ed., Academic Press, New York, pgs. 1-12 (1983); Seifter et al., *Meth Enzymol* 182:626-646 (1990); Rattan et al., *Ann NY Acad Sci* 663:48-62 (1992)).

The present invention also provides for fusion proteins comprising, consisting essentially of, or consisting of a Sema6A polypeptide fusion. In certain embodiments, the Sema6A fusion polypeptide binds to plexin-A2 or plexin-A4. In certain embodiments of the invention, a Sema6A polypeptide, e.g., a Sema6A polypeptide comprising the Sema domains and PSI domain or the entire extracellular domain (corresponding to amino acids 1 to 649 of SEQ ID NO: 2), is fused to a heterologous polypeptide moiety to form a Sema6A fusion polypeptide Pharmacologically active polypeptides may exhibit rapid in vivo clearance, necessitating large doses to achieve therapeutically effective concentrations in the body. In addition, polypeptides smaller than about 60 kDa potentially undergo glomerular filtration, which sometimes leads to nephrotoxicity. Fusion or conjugation of polypeptide fragments can be employed to reduce or avoid the risk of such nephrotoxicity. Various heterologous amino acid sequences, i.e., polypeptide moieties or "carriers," for increasing the in vivo stability, i.e., serum half-life, of therapeutic polypeptides are known.

Due to its long half-life, wide in vivo distribution, and lack of enzymatic or immunological function, essentially full-length human serum albumin (HSA), or an HSA fragment, is commonly used as a heterologous moiety. Through application of methods and materials such as those taught in Yeh et al., *Proc. Natl. Acad. Sci. USA* 89:1904-08 (1992) and Syed et al., *Blood* 89:3243-52 (1997), HSA can be used to form a Sema6A fusion polypeptide that displays pharmacological activity by virtue of the Sema6A moiety while displaying significantly increased in vivo stability, e.g., 10-fold to 100-fold higher. The C-terminus of the HSA can be fused to the N-terminus of the Sema6A moiety. Since HSA is a naturally secreted protein, the HSA signal sequence can be exploited to obtain secretion of the Sema6A fusion protein into the cell culture medium when the fusion protein is produced in a eukaryotic, e.g., mammalian, expression system.

The signal sequence is a polynucleotide that encodes an amino acid sequence that initiates transport of a protein across the membrane of the endoplasmic reticulum. Signal sequences useful for constructing an immunofusion include antibody light chain signal sequences, e.g., antibody 14.18 (Gillies et al., *J. Immunol. Meth.* 125:191-202 (1989)), and antibody heavy chain signal sequences, e.g., the MOPC141 antibody heavy chain signal sequence (Sakano et al., *Nature* 286:5774 (1980)). Alternatively, other signal sequences can be used. See, e.g., Watson, *Nucl. Acids Res.* 12:5145 (1984). The signal peptide is usually cleaved in the lumen of the endoplasmic reticulum by signal peptidases. This results in the secretion of an immunofusin protein containing the Fc region and the Sema6A moiety.

In some embodiments, the DNA sequence may encode a proteolytic cleavage site between the secretion cassette and the Sema6A polypeptide. Such a cleavage site may provide, e.g., for the proteolytic cleavage of the encoded fusion protein, thus separating the Fc domain from the target protein. Useful proteolytic cleavage sites include amino acid sequences recognized by proteolytic enzymes such as trypsin, plasmin, thrombin, factor Xa, or enterokinase K.

The secretion cassette can be incorporated into a replicable expression vector. Useful vectors include linear nucleic acids, plasmids, phagemids, cosmids and the like. An exemplary expression vector is pdC, in which the transcription of the immunofusin DNA is placed under the control of the enhancer and promoter of the human cytomegalovirus. See, e.g., Lo et al., *Biochim. Biophys. Acta* 1088:712 (1991); and Lo et al., *Protein Engineering* 11:495-500 (1998). An appropriate host cell can be transformed or transfected with a DNA that encodes a Sema6A polypeptide and used for the expression and secretion of the Sema6A polypeptide. Host cells that are typically used include immortal hybridoma cells, myeloma cells, 293 cells, Chinese hamster ovary (CHO) cells, Hela cells, and COS cells.

In one embodiment, a Sema6A polypeptide is fused to a hinge and Fc region, i.e., the C-terminal portion of an Ig heavy chain constant region. Potential advantages of a Sema6A-Fc fusion include solubility, in vivo stability, and multivalency, e.g., dimerization. The Fc region used can be an IgA, IgD, or IgG Fc region (hinge-$C_H2$-$C_H3$). Alternatively, it can be an IgE or IgM Fe region (hinge-$C_H2$-$C_H3$-$C_H4$). An IgG Fc region is generally used, e.g., an $IgG_1$ Fc region or $IgG_4$ Fc region. In one embodiment, a sequence beginning in the hinge region just upstream of the papain cleavage site which defines IgG Fc chemically (i.e., residue 216, taking the first residue of heavy chain constant region to be 114 according to the Kabat system), or analogous sites of other immunoglobulins is used in the fusion. The precise site at which the fusion is made is not critical; particular sites are well known and may be selected in order to optimize the biological activity, secretion, or binding characteristics of the molecule. Materials and Methods for constructing and expressing DNA encoding Fc fusions are known in the art and can be applied to obtain Sema6A fusions without undue experimentation. Some embodiments of the invention employ a fusion protein such as those described in Capon et al., U.S. Pat. Nos. 5,428,130 and 5,565,335.

Fully intact, wild-type Fc regions display effector functions that may be unnecessary and undesired in an Fc fusion protein used in the methods of the present invention. Therefore, certain binding sites typically are deleted from the Fc region during the construction of the secretion cassette. For example, since coexpression with the light chain is unnecessary, the binding site for the heavy chain binding protein, Bip (Hendershot et al., *Immunol. Today* 8:111-14 (1987)), is deleted from the CH2 domain of the Fc region of IgE, such that this site does not interfere with the efficient secretion of the immunofusin. Transmembrane domain sequences, such as those present in IgM, also are generally deleted.

The IgG$_1$ Fc region is most often used. Alternatively, the Fc region of the other subclasses of immunoglobulin gamma (gamma-2, gamma-3 and gamma-4) can be used in the secretion cassette. The IgG$_1$ Fc region of immunoglobulin gamma-1 is generally used in the secretion cassette and includes at least part of the hinge region, the $C_H2$ region, and the $C_H3$ region. In some embodiments, the Fc region of immunoglobulin gamma-1 is a $C_H2$-deleted-Fc, which includes part of the hinge region and the $C_H3$ region, but not the $C_H2$ region. A $C_H2$-deleted-Fc has been described by Gillies et al., *Hum. Antibod. Hybridomas* 1:47 (1990). In some embodiments, the Fc region of one of IgA, IgD, IgE, or IgM, is used.

Sema6A-Fc fusion proteins can be constructed in several different configurations. In one configuration the C-terminus of the Sema6A moiety is fused directly to the N-terminus of the Fc hinge moiety. In a slightly different configuration, a short polypeptide, e.g., 2-10 amino acids, is incorporated into the fusion between the N-terminus of the Sema6A moiety and the C-terminus of the Fc moiety. Such a linker provides conformational flexibility, which may improve biological activity in some circumstances. If a sufficient portion of the hinge region is retained in the Fc moiety, the Sema6A-Fc fusion will dimerize, thus forming a divalent molecule. A homogeneous population of monomeric Fc fusions will yield monospecific, bivalent dimers. A mixture of two monomeric Fc fusions each having a different specificity will yield bispecific, bivalent dimers.

Any of a number of cross-linkers that contain a corresponding amino-reactive group and thiol-reactive group can be used to link Sema6A polypeptides to serum albumin or other heterologous polypeptides. Examples of suitable linkers include amine reactive cross-linkers that insert a thiol-reactive maleimide, e.g., SMCC, AMAS, BMPS, MBS, EMCS, SMPB, SMPH, KMUS, and GMBS. Other suitable linkers insert a thiol-reactive haloacetate group, e.g., SBAP, SIA, SIAB. Linkers that provide a protected or non-protected thiol for reaction with sulfhydryl groups to product a reducible linkage include SPDP, SMPT, SATA, and SATP. Such reagents are commercially available (e.g., Pierce Chemicals).

Conjugation does not have to involve the N-terminus of a Sema6A polypeptide or the thiol moiety on serum albumin. For example, Sema6A-albumin fusions can be obtained using genetic engineering techniques, wherein the Sema6A moiety is fused to the serum albumin gene at its N-terminus, C-terminus, or both.

Sema6A polypeptides can be fused to heterologous peptides to facilitate purification or identification of the Sema6A moiety. For example, a histidine tag can be fused to a Sema6A polypeptide to facilitate purification using commercially available chromatography media.

In some embodiments of the invention, a Sema6A fusion construct is used to enhance the production of a Sema6A moiety in bacteria. In such constructs a bacterial protein normally expressed and/or secreted at a high level is employed as the N-terminal fusion partner of a Sema6A polypeptide. See, e.g., Smith et al., *Gene* 67:31 (1988); Hopp et al., *Biotechnology* 6:1204 (1988); La Vallie et al., *Biotechnology* 11:187 (1993).

By fusing a Sema6A moiety at the amino and carboxy termini of a suitable fusion partner, bivalent or tetravalent forms of a Sema6A polypeptide can be obtained. For example, a Sema6A moiety can be fused to the amino and carboxy termini of an Ig moiety to produce a bivalent monomeric polypeptide containing two Sema6A moieties. Upon dimerization of two of these monomers, by virtue of the Ig moiety, a tetravalent form of a Sema6A protein is obtained. Such multivalent forms can be used to achieve increased binding affinity for the target. Multivalent forms of Sema6A also can be obtained by placing Sema6A moieties in tandem to form concatamers, which can be employed alone or fused to a fusion partner such as Ig or HSA.

In certain embodiments, Sema6A polypeptides for use in the methods of the present invention further comprise a targeting moiety. Targeting moieties include a protein or a peptide which directs localization to a certain part of the body, for example, to the brain or compartments therein. In certain embodiments, Sema6A polypeptides for use in the methods of the present invention are attached or fused to a brain targeting moiety. The brain targeting moieties are attached covalently (e.g., direct, translational fusion, or by chemical linkage either directly or through a spacer molecule, which can be optionally cleavable) or non-covalently attached (e.g., through reversible interactions such as avidin, biotin, protein A, IgG, etc.). In other embodiments, the Sema6A polypeptides for use in the methods of the present invention thereof are attached to one more brain targeting moieties. In additional embodiments, the brain targeting moiety is attached to a plurality of Sema6A polypeptides for use in the methods of the present invention.

A brain targeting moiety associated with a Sema6A polypeptide enhances brain delivery of such a Sema6A polypeptide. A number of polypeptides have been described which, when fused to a protein or therapeutic agent, delivers the protein or therapeutic agent through the blood brain barrier (BBB). Non-limiting examples include the single domain antibody FC5 (Abulrob et al., *J. Neurochem.* 95, 1201-1214 (2005)); mAB 83-14, a monoclonal antibody to the human insulin receptor (Pardridge et al., *Pharmacol. Res.* 12, 807-816 (1995)); the B2, B6 and B8 peptides binding to the human transferrin receptor (hTfR) (Xia et al., *J. Virol.* 74, 11359-11366 (2000)); the OX26 monoclonal antibody to the transferrin receptor (Pardridge et al., *J. Pharmacol. Exp. Ther.* 259, 66-70 (1991)); and SEQ ID NOs: 1-18 of U.S. Pat. No. 6,306,365. The contents of the above references are incorporated herein by reference in their entirety.

Enhanced brain delivery of a Sema6A composition is determined by a number of means well established in the art. For example, administering to an animal a radioactively labelled Sema6A polypeptide linked to a brain targeting moiety; determining brain localization; and comparing localization with an equivalent radioactively labelled Sema6A polypeptide that is not associated with a brain targeting moiety. Other means of determining enhanced targeting are described in the above references.

Conjugated Polymers (Other than Polypeptides)

Some embodiments of the invention involve a Sema6A polypeptide wherein one or more polymers are conjugated (covalently linked) to the Sema6A polypeptide. Examples of polymers suitable for such conjugation include polypeptides (discussed above), sugar polymers and polyalkylene glycol chains. Typically, but not necessarily, a polymer is conjugated to the Sema6A polypeptide for the purpose of improving one or more of the following: solubility, stability, or bioavailability.

The class of polymer generally used for conjugation to a Sema6A polypeptide is a polyalkylene glycol. Polyethylene glycol (PEG) is most frequently used. PEG moieties, e.g., 1, 2, 3, 4 or 5 PEG polymers, can be conjugated to each Sema6A polypeptide to increase serum half life, as compared to the Sema6A polypeptide alone. PEG moieties are non-antigenic and essentially biologically inert. PEG moieties used in the practice of the invention may be branched or unbranched.

The number of PEG moieties attached to the Sema6A polypeptide and the molecular weight of the individual PEG chains can vary. In general, the higher the molecular weight of the polymer, the fewer polymer chains attached to the polypeptide. Usually, the total polymer mass attached to the Sema6A polypeptide is from 20 kDa to 40 kDa. Thus, if one polymer chain is attached, the molecular weight of the chain is generally 20-40 kDa. If two chains are attached, the molecular weight of each chain is generally 10-20 kDa. If three chains are attached, the molecular weight is generally 7-14 kDa.

The polymer, e.g., PEG, can be linked to the Sema6A polypeptide through any suitable, exposed reactive group on the polypeptide. The exposed reactive group(s) can be, e.g., an N-terminal amino group or the epsilon amino group of an internal lysine residue, or both. An activated polymer can react and covalently link at any free amino group on the Sema6A polypeptide. Free carboxylic groups, suitably activated carbonyl groups, hydroxyl, guanidyl, imidazole, oxidized carbohydrate moieties and mercapto groups of the Sema6A polypeptide (if available) also can be used as reactive groups for polymer attachment.

In a conjugation reaction, from about 1.0 to about 10 moles of activated polymer per mole of polypeptide, depending on polypeptide concentration, is typically employed. Usually, the ratio chosen represents a balance between maximizing the reaction while minimizing side reactions (often non-specific) that can impair the desired pharmacological activity of the Sema6A polypeptide. Preferably, at least 50% of the biological activity (as demonstrated, e.g., in any of the assays described herein or known in the art) of the Sema6A polypeptide is retained, and most preferably nearly 100% is retained.

The polymer can be conjugated to the Sema6A polypeptide using conventional chemistry. For example, a polyalkylene glycol moiety can be coupled to a lysine epsilon amino group of the Sema6A polypeptide. Linkage to the lysine side chain can be performed with an N-hydroxylsuccinimide (NHS) active ester such as PEG succinimidyl succinate (SS-PEG) and succinimidyl propionate (SPA-PEG). Suitable polyalkylene glycol moieties include, e.g., carboxymethyl-NHS and norleucine-NHS, SC. These reagents are commercially available. Additional amine-reactive PEG linkers can be substituted for the succinimidyl moiety. These include, e.g., isothiocyanates, nitrophenylcarbonates (PNP), epoxides, benzotriazole carbonates, SC-PEG, tresylate, aldehyde, epoxide, carbonylimidazole and PNP carbonate. Conditions are usually optimized to maximize the selectivity and extent of reaction. Such optimization of reaction conditions is within ordinary skill in the art.

PEGylation can be carried out by any of the PEGylation reactions known in the art. See, e.g., *Focus on Growth Factors* 3:4-10 (1992), and European patent applications EP 0 154 316 and EP 0 401 384. PEGylation may be carried out using an acylation reaction or an alkylation reaction with a reactive polyethylene glycol molecule (or an analogous reactive water-soluble polymer).

PEGylation by acylation generally involves reacting an active ester derivative of polyethylene glycol. Any reactive PEG molecule can be employed in the PEGylation. PEG esterified to N-hydroxysuccinimide (NHS) is a frequently used activated PEG ester. As used herein, "acylation" includes without limitation the following types of linkages between the therapeutic protein and a water-soluble polymer such as PEG: amide, carbamate, urethane, and the like. See, e.g., *Bioconjugate Chem.* 5:133-140, 1994. Reaction parameters are generally selected to avoid temperature, solvent, and pH conditions that would damage or inactivate the Sema6A polypeptide.

Generally, the connecting linkage is an amide and typically at least 95% of the resulting product is mono-, di- or tri-PEGylated. However, some species with higher degrees of PEGylation may be formed in amounts depending on the specific reaction conditions used. Optionally, purified PEGylated species are separated from the mixture, particularly unreacted species, by conventional purification methods, including, e.g., dialysis, salting-out, ultrafiltration, ion-exchange chromatography, gel filtration chromatography, hydrophobic exchange chromatography, and electrophoresis.

PEGylation by alkylation generally involves reacting a terminal aldehyde derivative of PEG with Sema6A polypeptide in the presence of a reducing agent. In addition, one can manipulate the reaction conditions to favor PEGylation substantially only at the N-terminal amino group of Sema6A polypeptide, i.e. a mono-PEGylated protein. In either case of mono-PEGylation or poly-PEGylation, the PEG groups are typically attached to the protein via a $—C_H2\text{-}NH—$ group. With particular reference to the $—C_H2$-group, this type of linkage is known as an "alkyl" linkage.

Derivatization via reductive alkylation to produce an N-terminally targeted mono-PEGylated product exploits differential reactivity of different types of primary amino groups (lysine versus the N-terminal) available for derivatization. The reaction is performed at a pH that allows one to take advantage of the pKa differences between the epsilon-amino groups of the lysine residues and that of the N-terminal amino group of the protein. By such selective derivatization, attachment of a water-soluble polymer that contains a reactive group, such as an aldehyde, to a protein is controlled: the conjugation with the polymer takes place predominantly at the N-terminus of the protein and no significant modification of other reactive groups, such as the lysine side chain amino groups, occurs.

The polymer molecules used in both the acylation and alkylation approaches are selected from among water-soluble polymers. The polymer selected is typically modified to have a single reactive group, such as an active ester for acylation or an aldehyde for alkylation, so that the degree of polymerization may be controlled as provided for in the present methods. An exemplary reactive PEG aldehyde is polyethylene glycol propionaldehyde, which is water stable, or mono C1-C10 alkoxy or aryloxy derivatives thereof (see, e.g., Harris et al., U.S. Pat. No. 5,252,714). The polymer may be branched or unbranched. For the acylation reactions, the polymer(s) selected typically have a single reactive ester group. For reductive alkylation, the polymer(s) selected typically have a single reactive aldehyde group. Generally, the water-soluble polymer will not be selected from naturally occurring glycosyl residues, because these are usually made more conveniently by mammalian recombinant expression systems.

Methods for preparing a PEGylated Sema6A polypeptide generally includes the steps of (a) reacting a Sema6A polypeptide with polyethylene glycol (such as a reactive ester or aldehyde derivative of PEG) under conditions whereby the molecule becomes attached to one or more PEG groups, and (b) obtaining the reaction product(s). In general, the optimal reaction conditions for the acylation reactions will be determined case-by-case based on known parameters and the desired result. For example, a larger the ratio of PEG to protein, generally leads to a greater the percentage of poly-PEGylated product.

Reductive alkylation to produce a substantially homogeneous population of mono-polymer/Sema6A polypeptide generally includes the steps of: (a) reacting a Sema6A protein or polypeptide with a reactive PEG molecule under reductive alkylation conditions, at a pH suitable to pen-nit selective modification of the N-terminal amino group of the polypeptide; and (b) obtaining the reaction product(s).

For a substantially homogeneous population of mono-polymer/Sema6A polypeptide, the reductive alkylation reaction conditions are those that permit the selective attachment of the water-soluble polymer moiety to the N-terminus of the polypeptide. Such reaction conditions generally provide for pKa differences between the lysine side chain amino groups and the N-terminal amino group. For purposes of the present invention, the pH is generally in the range of 3-9, typically 3-6.

Sema6A polypeptides can include a tag, e.g., a moiety that can be subsequently released by proteolysis. Thus, the lysine moiety can be selectively modified by first reacting a His-tag modified with a low-molecular-weight linker such as Traut's reagent (Pierce) which will react with both the lysine and N-terminus, and then releasing the His tag. The polypeptide will then contain a free SH group that can be selectively modified with a PEG containing a thiol-reactive head group such as a maleimide group, a vinylsulfone group, a haloacetate group, or a free or protected SH.

Traut's reagent can be replaced with any linker that will set up a specific site for PEG attachment. For example, Traut's reagent can be replaced with SPDP, SMPT, SATA, or SATP (Pierce). Similarly one could react the protein with an amine-reactive linker that inserts a maleimide (for example SMCC, AMAS, BMPS, MBS, EMCS, SMPB, SMPH, KMUS, or GMBS), a haloacetate group (SBAP, SIA, STAB), or a vinylsulfone group and react the resulting product with a PEG that contains a free SH.

In some embodiments, the polyalkylene glycol moiety is coupled to a cysteine group of the Sema6A polypeptide. Coupling can be effected using, e.g., a maleimide group, a vinylsulfone group, a haloacetate group, or a thiol group.

Optionally, the Sema6A polypeptide is conjugated to the polyethylene-glycol moiety through a labile bond. The labile bond can be cleaved in, e.g., biochemical hydrolysis, proteolysis, or sulfhydryl cleavage. For example, the bond can be cleaved under in vivo (physiological) conditions.

The reactions may take place by any suitable method used for reacting biologically active materials with inert polymers, generally at about pH 5-8, e.g., pH 5, 6, 7, or 8, if the reactive groups are on the alpha amino group at the N-terminus. Generally the process involves preparing an activated polymer and thereafter reacting the protein with the activated polymer to produce the protein suitable for formulation.

Vectors

Vectors comprising nucleic acids encoding Sema6A polypeptides may also be used for the methods of the invention. The choice of vector and expression control sequences to which such nucleic acids are operably linked depends on the functional properties desired, e.g., protein expression, and the host cell to be transformed.

Expression control elements useful for regulating the expression of an operably linked coding sequence are known in the art. Examples include, but are not limited to, inducible promoters, constitutive promoters, secretion signals, and other regulatory elements. When an inducible promoter is used, it can be controlled, e.g., by a change in nutrient status, or a change in temperature, in the host cell medium.

The vector can include a prokaryotic replicon, i.e., a DNA sequence having the ability to direct autonomous replication and maintenance of the recombinant DNA molecule extrachromosomally in a bacterial host cell. Such replicons are well known in the art. In addition, vectors that include a prokaryotic replicon may also include a gene whose expression confers a detectable marker such as a drug resistance. Examples of bacterial drug-resistance genes are those that confer resistance to ampicillin or tetracycline.

Vectors that include a prokaryotic replicon can also include a prokaryotic or bacteriophage promoter for directing expression of the coding gene sequences in a bacterial host cell. Promoter sequences compatible with bacterial hosts are typically provided in plasmid vectors containing convenient restriction sites for insertion of a DNA segment to be expressed. Examples of such plasmid vectors are pUC8, pUC9, pBR322 and pBR329 (BioRad), pPL and pKK223 (Pharmacia). Any suitable prokaryotic host can be used to express a recombinant DNA molecule encoding a protein used in the methods of the invention.

For the purposes of this invention, numerous expression vector systems may be employed. For example, one class of vector utilizes DNA elements which are derived from animal viruses such as bovine papilloma virus, polyoma virus, adenovirus, vaccinia virus, baculovirus, retroviruses (RSV, MMTV or MOMLV) or SV40 virus. Others involve the use of polycistronic systems with internal ribosome binding sites. Additionally, cells which have integrated the DNA into their chromosomes may be selected by introducing one or more markers which allow selection of transfected host cells. The marker may provide for prototrophy to an auxotrophic host, biocide resistance (e.g., antibiotics) or resistance to heavy metals such as copper. The selectable marker gene can either be directly linked to the DNA sequences to be expressed, or introduced into the same cell by cotransformation. The neomycin phosphotransferase (neo) gene is an example of a selectable marker gene (Southern et al., *J. Mol. Anal. Genet.* 1:327-341 (1982)). Additional elements may also be needed for optimal synthesis of mRNA. These elements may include signal sequences, splice signals, as well as transcriptional promoters, enhancers, and termination signals.

In one embodiment, a proprietary expression vector of Biogen IDEC, Inc., referred to as NEOSPLA (U.S. Pat. No. 6,159,730) may be used. This vector contains the cytomegalovirus promoter/enhancer, the mouse beta globin major promoter, the SV40 origin of replication, the bovine growth hormone polyadenylation sequence, neomycin phosphotransferase exon 1 and exon 2, the dihydrofolate reductase gene and leader sequence. This vector has been found to result in very high level expression upon transfection in CHO cells, followed by selection in G418 containing medium and methotrexate amplification. Of course, any expression vector which is capable of eliciting expression in eukaryotic cells may be used in the present invention. Examples of suitable vectors include, but are not limited to plasmids pcDNA3, pHCMV/Zeo, pCR3.1, pEF1/His, pIND/GS, pRc/HCMV2, pSV40/Zeo2, pTRACER-HCMV, pUB6/V5-His, pVAX1, and pZeoSV2 (available from Invitrogen, San Diego, Calif.), and plasmid pCI (available from Promega, Madison, Wis.). Additional eukaryotic cell expression vectors are known in the art and are commercially available. Typically, such vectors contain convenient restriction sites for insertion of the desired DNA segment. Exemplary vectors include pSVL and pKSV-10 (Pharmacia), pBPV-1, pml2d (International Biotechnologies), pTDT1 (ATCC 31255), retroviral expression vector pMIG and pLL3.7, adenovirus shuttle vector pDC315, and AAV vectors. Other exemplary vector systems are disclosed e.g., in U.S. Pat. No. 6,413,777.

In general, screening large numbers of transformed cells for those which express suitably high levels of the polypeptide is routine experimentation which can be carried out, for example, by robotic systems.

Frequently used regulatory sequences for mammalian host cell expression include viral elements that direct high levels of protein expression in mammalian cells, such as promoters and enhancers derived from retroviral LTRs, cytomegalovirus (CMV) (such as the CMV promoter/enhancer), Simian Virus 40 (SV40) (such as the SV40 promoter/enhancer), adenovirus, (e.g., the adenovirus major late promoter (Adm1P)), polyoma and strong mammalian promoters such as native immunoglobulin and actin promoters. For further description of viral regulatory elements, and sequences thereof, see e.g., Stinski, U.S. Pat. No. 5,168,062; Bell, U.S. Pat. No. 4,510,245; and Schaffner, U.S. Pat. No. 4,968,615.

The recombinant expression vectors may carry sequences that regulate replication of the vector in host cells (e.g., origins of replication) and selectable marker genes. The selectable marker gene facilitates selection of host cells into which the vector has been introduced (see, e.g., Axel, U.S. Pat. Nos. 4,399,216; 4,634,665 and 5,179,017). For example, typically the selectable marker gene confers resistance to a drug, such as G418, hygromycin or methotrexate, on a host cell into which the vector has been introduced. Frequently used selectable marker genes include the dihydrofolate reductase (DHFR) gene (for use in dhfr-host cells with methotrexate selection/amplification) and the neo gene (for G418 selection).

Vectors encoding Sema6A polypeptides can be used for transformation of a suitable host cell. Transformation can be by any suitable method. Methods for introduction of exogenous DNA into mammalian cells are well known in the art and include dextran-mediated transfection, calcium phosphate precipitation, polybrene-mediated transfection, protoplast fusion, electroporation, encapsulation of the polynucleotide(s) in liposomes, and direct microinjection of the DNA into nuclei. In addition, nucleic acid molecules may be introduced into mammalian cells by viral vectors.

Transformation of host cells can be accomplished by conventional methods suited to the vector and host cell employed. For transformation of prokaryotic host cells, electroporation and salt treatment methods can be employed (Cohen et al., *Proc. Natl. Acad. Sci. USA* 69:2110-14 (1972)). For transformation of vertebrate cells, electroporation, cationic lipid or salt treatment methods can be employed. See, e.g., Graham et al., *Virology* 52:456-467 (1973); Wigler et al., *Proc. Natl. Acad. Sci. USA* 76:1373-76 (1979).

The host cell line used for protein expression can be of mammalian origin; those skilled in the art are credited with ability to preferentially determine particular host cell lines which are best suited for the desired gene product to be expressed therein. Exemplary host cell lines include, but are not limited to NSO, SP2 cells, baby hamster kidney (BHK) cells, monkey kidney cells (COS), human hepatocellular carcinoma cells (e.g., Hep G2), A549 cells DG44 and DUXB11 (Chinese Hamster Ovary lines, DHFR minus), HELA (human cervical carcinoma), CV1 (monkey kidney line), COS (a derivative of CV1 with SV40 T antigen), R1610 (Chinese hamster fibroblast) BALBC/3T3 (mouse fibroblast), HAK (hamster kidney line), SP2/0 (mouse myeloma), P3×63-Ag3.653 (mouse myeloma), BFA-1c1BPT (bovine endothelial cells), RAJI (human lymphocyte) and 293 (human kidney). Host cell lines are typically available from commercial services, the American Tissue Culture Collection or from published literature.

Expression of polypeptides from production cell lines can be enhanced using known techniques. For example, the glutamine synthetase (GS) system is commonly used for enhancing expression under certain conditions. See, e.g., European Patent Nos. 0 216 846, 0 256 055, and 0 323 997 and European Patent Application No. 89303964.4.

Host Cells

Host cells for expression of a Sema6A polypeptide for use in a method of the invention may be prokaryotic or eukaryotic. Exemplary eukaryotic host cells include, but are not limited to, yeast and mammalian cells, e.g., Chinese hamster ovary (CHO) cells (ATCC Accession No. CCL61), NIH Swiss mouse embryo cells NIH-3T3 (ATCC Accession No. CRL1658), and baby hamster kidney cells (BHK). Other useful eukaryotic host cells include insect cells and plant cells. Exemplary prokaryotic host cells are *E. coli* and *Streptomyces*.

Gene Therapy

A Sema6A polypeptide can be produced in vivo in a mammal, e.g., a human patient, using a gene-therapy approach to treatment of a nervous-system disease, disorder or injury in which promoting survival, proliferation and/or differentiation of oligodendrocytes or promoting myelination of neurons would be therapeutically beneficial. This involves administration of a suitable Sema6A polypeptide-encoding nucleic acid operably linked to suitable expression control sequences. Generally, these sequences are incorporated into a viral vector. Suitable viral vectors for such gene therapy include an adenoviral vector, an alphavirus vector, an enterovirus vector, a pestivirus vector, a lentiviral vector, a baculoviral vector, a herpesvirus vector, an Epstein Barr viral vector, a papovaviral vector, a poxvirus vector, a vaccinia viral vector, an adeno-associated viral vector and a herpes simplex viral vector. The viral vector can be a replication-defective viral vector. Adenoviral vectors that have a deletion in its E1 gene or E3 gene are typically used. When an adenoviral vector is used, the vector usually does not have a selectable marker gene.

Pharmaceutical Compositions

The Sema6A polypeptides used in the methods of the invention may be formulated into pharmaceutical compositions for administration to mammals, including humans. The pharmaceutical compositions used in the methods of this invention comprise pharmaceutically acceptable carriers, including, e.g., ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The compositions used in the methods of the present invention may be administered by any suitable method, e.g., parenterally, intraventricularly, orally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques.

As described previously, Sema6A polypeptides used in the methods of the invention act in the nervous system to promote survival, proliferation and differentiation of oligodendrocytes and myelination of neurons. Accordingly, in the methods of the invention, the Sema6A polypeptides are administered in such a way that they cross the blood-brain barrier. This crossing can result from the physico-chemical properties inherent in the Sema6A polypeptide molecule itself, from other components in a pharmaceutical formulation, or from the use of a mechanical device such as a needle, cannula or surgical instruments to breach the blood-brain barrier. Where the Sema6A polypeptide is a molecule that does not inherently cross the blood-brain barrier, e.g., a fusion to a moiety that facilitates the crossing, suitable routes of administration are, e.g., intrathecal or intracranial, e.g., directly into a chronic lesion of MS. Where the Sema6A polypeptide is a molecule that inherently crosses the blood-brain barrier, the route of administration may be by one or more of the various routes described below.

Sterile injectable forms of the compositions used in the methods of this invention may be aqueous or oleaginous suspension. These suspensions may be formulated according to techniques known in the art using suitable dispersing or wetting agents and suspending agents. The sterile, injectable preparation may also be a sterile, injectable solution or suspension in a non-toxic parenterally acceptable diluent or solvent, for example as a suspension in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically acceptable oils, such as olive oil or castor oil, especially in their polyoxyethylated versions. These oil solutions or suspensions may also contain a long-chain alcohol diluent or dispersant, such as carboxymethyl cellulose or similar dispersing agents which are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

Parenteral formulations may be a single bolus dose, an infusion or a loading bolus dose followed with a maintenance dose. These compositions may be administered at specific fixed or variable intervals, e.g., once a day, or on an "as needed" basis.

Certain pharmaceutical compositions used in the methods of this invention may be orally administered in an acceptable dosage form including, e.g., capsules, tablets, aqueous suspensions or solutions. Certain pharmaceutical compositions also may be administered by nasal aerosol or inhalation. Such compositions may be prepared as solutions in saline, employing benzyl alcohol or other suitable preservatives, absorption promoters to enhance bioavailability, and/or other conventional solubilizing or dispersing agents.

The amount of a Sema6A polypeptide that may be combined with the carrier materials to produce a single dosage form will vary depending upon the host treated, the type of polypeptide used and the particular mode of administration. The composition may be administered as a single dose, multiple doses or over an established period of time in an infusion. Dosage regimens also may be adjusted to provide the optimum desired response (e.g., a therapeutic or prophylactic response).

The methods of the invention use a "therapeutically effective amount" or a "prophylactically effective amount" of a Sema6A polypeptide. Such a therapeutically or prophylactically effective amount may vary according to factors such as the disease state, age, sex, and weight of the individual. A therapeutically or prophylactically effective amount is also one in which any toxic or detrimental effects are outweighed by the therapeutically beneficial effects.

A specific dosage and treatment regimen for any particular patient will depend upon a variety of factors, including the particular Sema6A polypeptide used, the patient's age, body weight, general health, sex, and diet, and the time of administration, rate of excretion, drug combination, and the severity of the particular disease being treated. Judgment of such factors by medical caregivers is within the ordinary skill in the art. The amount will also depend on the individual patient to be treated, the route of administration, the type of formulation, the characteristics of the compound used, the severity of the disease, and the desired effect. The amount used can be determined by pharmacological and pharmacokinetic principles well known in the art.

In the methods of the invention the Sema6A polypeptides are generally administered directly to the nervous system, intracerebroventricularly, or intrathecally, e.g. into a chronic lesion of MS. Compositions for administration according to the methods of the invention can be formulated so that a dosage of 0.001-10 mg/kg body weight per day of the Sema6A polypeptide is administered. In some embodiments of the invention, the dosage is 0.01-1.0 mg/kg body weight per day. In some embodiments, the dosage is 0.001-0.5 mg/kg body weight per day. In certain embodiments, the dosage is 5 mg/kg-100 mg/kg body weight per day. In further embodiments of the invention, the dosage is 50 mg/kg-500 mg/kg body weight per day. The present invention also includes the dosage of 100 mg/kg-1 g/kg body weight per day. Non-limiting examples of the dosage used in the methods of the present invention is selected from the group consisting of 0.5, 1, 2, 3, 4, 5, 6, 7, 8, 9, 10, 11, 12, 13, 14, 15, 16, 17, 18 19, 20, 25, 30, 35, 40, 50, 60 70, 80 90, 100, 150, 200, 250, 300, 400, 500, 600, 700, 800, 900, or 1000 mg/kg body weight per day. The dosage used in the present invention may be 1 g/kg-5 g/kg body weight per day. Doses intermediate in the above ranges are also intended to be within the scope of the invention. Subjects can be administered such doses daily, on alternative days, weekly or according to any other schedule determined by empirical analysis. An exemplary treatment entails administration in multiple dosages over a prolonged period, for example, of at least six months. Additional exemplary treatment regimes entail administration once per every two weeks or once a month or once every 3 to 6 months. Exemplary dosage schedules include, but are not limited to, 1-10 mg/kg or 15 mg/kg on consecutive days, 30 mg/kg on alternate days or 60 mg/kg weekly.

In certain embodiments, a subject can be treated with a nucleic acid molecule encoding a Sema6A polypeptide. Doses for nucleic acids range from about 10 ng to 1 g, 100 ng to 100 mg, 1 μg to 10 mg, or 30-300 μg mDNA per patient. Doses for infectious viral vectors vary from 10-100, or more, virions per dose.

Supplementary active compounds also can be incorporated into the compositions used in the methods of the invention. For example, a Sema6A polypeptide or a fusion protein may be coformulated with and/or coadministered with one or more additional therapeutic agents.

The invention encompasses any suitable delivery method for a Sema6A polypeptide to a selected target tissue, including bolus injection of an aqueous solution or implantation of a controlled-release system. Use of a controlled-release implant reduces the need for repeat injections.

The Sema6A polypeptides used in the methods of the invention may be directly infused into the brain Various implants for direct brain infusion of compounds are known and are effective in the delivery of therapeutic compounds to human patients suffering from neurological disorders. These include chronic infusion into the brain using a pump, stereotactically implanted, temporary interstitial catheters, permanent intracranial catheter implants, and surgically implanted biodegradable implants. See, e.g., Gill et al., supra; Scharfen et al., "High Activity Iodine-125 Interstitial Implant For Gliomas," *Int. J. Radiation Oncology Biol. Phys.* 24(4):583-591 (1992); Gaspar et al., "Permanent 1251 Implants for Recurrent Malignant Gliomas," *Int. J. Radiation Oncology Biol. Phys.* 43(5):977-982 (1999); chapter 66, pages 577-580, Bellezza et al., "Stereotactic Interstitial Brachytherapy," in Gildenberg et al., *Textbook of Stereotactic and Functional Neurosurgery*, McGraw-Hill (1998); and Brem et al., "The Safety of Interstitial Chemotherapy with BCNU-Loaded Polymer Followed by Radiation Therapy in the Treatment of Newly Diagnosed Malignant Gliomas: Phase I Trial," *J. Neuro-Oncology* 26:111-23 (1995).

The compositions may also comprise a Sema6A polypeptide dispersed in a biocompatible carrier material that functions as a suitable delivery or support system for the compounds. Suitable examples of sustained release carriers include semipermeable polymer matrices in the form of shaped articles such as suppositories or capsules. Implantable or microcapsular sustained release matrices include polylactides (U.S. Pat. No. 3,773,319; EP 58,481), copolymers of L-glutamic acid and gamma-ethyl-L-glutamate (Sidman et al., *Biopolymers* 22:547-56 (1985)); poly(2-hydroxyethyl-methacrylate), ethylene vinyl acetate (Langer et al., *J. Biomed. Mater. Res.* 15:167-277 (1981); Langer, *Chem. Tech.* 12:98-105 (1982)) or poly-D-(–)-3hydroxybutyric acid (EP 133,988).

In some embodiments of the invention, a Sema6A polypeptide is administered to a patient by direct infusion into an appropriate region of the brain. See, e.g., Gill et al., "Direct brain infusion of glial cell line-derived neurotrophic factor in Parkinson disease," *Nature Med.* 9: 589-95 (2003). Alternative techniques are available and may be applied to administer a Sema6A polypeptide according to the invention. For example, stereotactic placement of a catheter or implant can be accomplished using the Riechert-Mundinger unit and the ZD (Zamorano-Dujovny) multipurpose localizing unit. A contrast-enhanced computerized tomography (CT) scan, injecting 120 ml of omnipaque, 350 mg iodine/ml, with 2 mm slice thickness can allow three-dimensional multiplanar treatment planning (STP, Fischer, Freiburg, Germany). This equipment permits planning on the basis of magnetic resonance imaging studies, merging the CT and MM target information for clear target confirmation.

The Leksell stereotactic system (Downs Surgical, Inc., Decatur, Ga.) modified for use with a GE CT scanner (General Electric Company, Milwaukee, Wis.) as well as the Brown-Roberts-Wells (BRW) stereotactic system (Radionics, Burlington, Mass.) can be used for this purpose. Thus, on the morning of the implant, the annular base ring of the BRW stereotactic frame can be attached to the patient's skull. Serial CT sections can be obtained at 3 mm intervals though the (target tissue) region with a graphite rod localizer frame clamped to the base plate. A computerized treatment planning program can be run on a VAX 11/780 computer (Digital Equipment Corporation, Maynard, Mass.) using CT coordinates of the graphite rod images to map between CT space and BRW space.

The methods of treatment of demyelination or dysmyelination disorders as described herein are typically tested in vitro, and then in vivo in an acceptable animal model, for the desired therapeutic or prophylactic activity, prior to use in humans. Suitable animal models, including transgenic animals, are will known to those of ordinary skill in the art. For example, in vitro assays to demonstrate the differentiation and survival effect of the Sema6A polypeptides are described herein. The effect of the Sema6A polypeptides on myelination of axons or oligodendrocyte differentiation can be tested in vitro as described in the Examples. Finally, in vivo tests can be performed by creating transgenic mice which express the Sema6A polypeptide or by administering the Sema6A polypeptide to mice or rats in models.

Diagnosis or Monitoring of Neurodegenerative Disease

Some embodiments of the present invention are directed to a method for diagnosing or monitoring a neurological disease or condition in a subject by (a) obtaining a specimen such as a tissue or a biological fluid sample, e.g., blood or CSF, from the subject to be diagnosed or monitored, (b) measuring the level of Sema6A polypeptide in the specimen, and (c) comparing the level of Sema6A polypeptide to a reference specimen.

By the term "diagnose" is meant to identify an individual as having a particular disease or condition. By the term "monitor" is meant to check constantly and/or periodically on a given condition or phenomenon. In one embodiment, the method for monitoring a neurodegenerative disease includes obtaining biological fluid samples at several time points at intervals as part of the monitoring of the patient during the treatment for neurodegenerative disease. In another embodiment, the method for monitoring a neurodegenerative disease includes obtaining biological fluid samples at several time points at intervals as part of the monitoring of the patient during the treatment for MS.

In one embodiment, the disease or condition that is to be diagnosed or monitored multiple sclerosis (MS). In other embodiments, the diseasr or condition may be selected from the group consisting of progressive multifocal leukoencephalopathy (PML), encephalomyelitis (EPL), central pontine myelolysis (CPM), adrenoleukodystrophy, Alexander's disease, Pelizaeus Merzbacher disease (PMZ), Globoid cell Leucodystrophy (Krabbe's disease), Wallerian Degeneration, optic neuritis, transverse myelitis, amylotrophic lateral sclerosis (ALS), Huntington's disease, Alzheimer's disease, Parkinson's disease, spinal cord injury, traumatic brain injury, post radiation injury, neurologic complications of chemotherapy, stroke, acute ischemic optic neuropathy, vitamin E deficiency, isolated vitamin E deficiency syndrome, AR, Bassen-Kornzweig syndrome, Marchiafava-Bignami syndrome, metachromatic leukodystrophy, trigeminal neuralgia, and Bell's palsy.

Biological fluid samples include, but are not limited to, blood, urine and cerebrospinal fluid (CSF). Methods by which biological fluid samples may be obtained include, but are not limited to, tissue biopsy, venipuncture, urine collection and spinal tap. In one embodiment, the biological fluid sample is CSF or blood.

Tissues include, but are not limited to, epithelium, muscle tissue, connective tissue, or nervous tissue. In one embodiment, the tissue is an epithelium, e.g., a part of skin tissue. Ln another embodiment, dendritic cells collected from a tissue or a biological fluid such as CSF or blood are used to detect the Sema6A expression.

The biological fluid sample is obtained from a subject. In some embodiments, the subject is a vertebrate. Vertebrates include but are not limited to humans, mice, rats, sheep, goats, pigs, cattle, horses, reptiles, fishes, amphibians, and in eggs of birds, reptiles and fish. In one embodiment, the subject is a human. In another embodiment, the subject is a human that has or is suspected of having a neurological disease selected from the list consisting of MS, progressive multifocal leukoencephalopathy (PML), encephalomyelitis (EPL), central pontine myelolysis (CPM), adrenoleukodystrophy, Alexander's disease, Pelizaeus Merzbacher disease (PMZ), Globoid cell Leucodystrophy (Krabbe's disease), Wallerian Degeneration, optic neuritis, transverse myelitis, amylotrophic lateral sclerosis (ALS), Huntington's disease, Alzheimer's disease, Parkinson's disease, spinal cord injury, traumatic brain injury, post radiation injury, neurologic complications of chemotherapy, stroke, acute ischemic optic neuropathy, vitamin E deficiency, isolated vitamin E deficiency syndrome, AR, Bassen-Kornzweig syndrome, Marchiafava-Bignami syndrome, metachromatic leukodystrophy, trigeminal neuralgia, and Bell's palsy. In one particular embodiment, the subject is an MS patient who has recently suffered at least one condition selected from the group consisting of numbness, weakness, visual impairment, loss of balance, dizziness, urinary bladder urgency, fatigue, and depression. As used herein, "recently" can be within 3, 5, 7, 10, 14 or 21 days.

Levels of Sema6A expression in the specimen can be indicative of a diseased state, e.g., the severity of the disease or condition, the propensity of the subject to contract the disease, the prognosis for the subject, or the efficacy of therapies against the disease.

The present invention further provides for methods to detect the presence of the Sema6A polypeptide in a specimen obtained from a subject. Any method known in the art for detecting proteins or mRNA can be used. Such methods include, but are not limited to Coomassie Blue staining, immunodiffusion, immunoelectrophoresis, immunochemical methods, binder-ligand assays, immunohistochemical techniques, agglutination, and complement assays. [Basic and Clinical Immunology, 217-262, Sites and Terr, eds., Appleton & Lange, Norwalk, Conn., (1991), which is incorporated by reference]. The method to detect Sema6A mRNA is well known in the art. Tuan Rocky, Recombinant Protein Protocols: Detection and Isolation (Methods in Molecular Biology) (Methods in Molecular Biology) ($1^{st}$ ed. Humana Press, PA 1997). Non-limiting examples of such methods are Northern blotting, nuclease protection assays, in situ hybridization, or an RT-PCR.

Numerous competitive and non-competitive protein binding immunoassays are well known in the art. Antibodies employed in such assays may be unlabeled, for example as used in agglutination tests, or labeled for use in a wide variety of assay methods. Labels that can be used include radionuclides, enzymes, fluorescers, chemiluminescers, enzyme substrates or co-factors, enzyme inhibitors, particles, dyes and the like for use in radioimmunoassay (RIA), enzyme immunoassays, e.g., enzyme-linked immunosorbent assay (ELISA), fluorescent immunoassays, Western blot analysis and the like.

In diagnosing or monitoring a neurological disease in a subject, the level of Sema6A polypeptide in the specimen can be compared to the level of Sema6A polypeptide in a reference specimen. A suitable reference specimen can include, but is not limited to, a tissue or a biological fluid sample from a neurologically normal individual. In one embodiment, the reference specimen is from a subject not afflicted with a neurodegenerative disease. In another embodiment, the reference specimen is from a subject not afflicted with MS. In addition, a known protein produced by the subject, such as albumin if measuring from serum or total protein may act as an internal standard or control.

Diagnostic Kits

Diagnostic kits are also contemplated by the present invention. These kits allow for the detection, diagnosis or monitoring of neurodegenerative diseases. The single-test approach adopted by these diagnostic kits will reduce the time required to diagnose a neurodegenerative disease in an individual and/or reduce the time required to detect differentially expressed proteins in a patient's biological fluid sample when he/she is being monitored for disease progression and/or effects of disease treatment.

One embodiment of the present invention is directed to diagnostic kits for the detection, diagnosis or monitoring of a neurodegenerative disease in a patient using an antibody or antigen binding fragment that specifically binds to a Sema6A polypeptide described herein and a detectable label. In another embodiment, the invention is directed to a diagnostic kit for the detection, diagnosis or monitoring of MS in a patient using an antibody or antigen binding fragment that specifically binds to a Sema6A polypeptide and a detectable label.

In some embodiments, the antibody is labeled with enzymes that are useful for detection, such as horseradish peroxidase, β-galactosidase, luciferase, alkaline phosphatase, glucose oxidase and the like. In embodiments that are labeled with a detectable enzyme, the antibody is detected by adding additional reagents that the enzyme uses to produce a detectable reaction product. For example, horseradish peroxidase with hydrogen peroxide and diaminobenzidine. An antibody also may be labeled with biotin, and detected through indirect measurement of avidin or streptavidin binding. An antibody may also be labeled with a predetermined polypeptide epitopes recognized by a secondary reporter (e.g., leucine zipper pair sequences, binding sites for secondary antibodies, metal binding domains, epitope tags).

The kits contemplated by the invention are intended to detect, diagnose or monitor neurodegenerative diseases in vertebrates including but not limited to humans, mice, rats, sheep, goats, pigs, cattle, horses, reptiles, fishes, amphibians, and in eggs of birds, reptiles and fish.

The diagnostic kits of the present invention comprise some or all of the essential reagents required to perform a desired immunoassay according to the present invention. The diagnostic kit may be presented in a commercially packaged form as a combination of one or more containers holding the necessary reagents. Such a kit may comprise an antibody of the present invention, in combination with several conventional kit components. Conventional kit components will be readily apparent to those skilled in the art and are disclosed in numerous publications, including, for example, Harlow and Lane; *Antibodies A Laboratory Manual*, Cold Spring Harbor Laboratory Press, Cold Spring Harbor, N.Y. 1988) which is incorporated herein by reference in its entirety. Conventional kit components may include such items as, for example, microtiter plates, buffers to maintain the pH of the assay mixture (such as, but not limited to Tris, HEPES, phosphate, carbonate etc.), conjugated second antibodies, such as peroxidase conjugated anti-mouse IgG (or any anti-IgG to the animal from which the first antibody was derived), stabilizers, biocides, inert proteins, e.g., bovine serum albumin, or the like, and other standard reagents.

The diagnostic kits of the present invention also can include kits which are suitable for use in the home as well as the clinic, doctor's office or laboratory. Examples of home testing kits can be found for example in U.S. Pat. No. 5,602,040, which is incorporated by reference herein.

The term "detection" as used herein in the context of detecting the presence of protein in a patient is intended to include the determining of the amount of protein or the ability to express an amount of protein in a patient, the estimation of prognosis in terms of probable outcome of a disease and prospect for recovery, the monitoring of the protein levels over a period of time as a measure of status of the condition, and the monitoring of protein levels for determining a preferred therapeutic regimen for the patient, e.g. one with neurodegenerative disease.

EXAMPLES

Example 1

Sema6A is Involved in Oligodendrocyte Biology

Oligodendrocytes mature through several developmental stages from oligodendrocyte progenitor cells (which express NG2), differentiating into pre-myelinating oligodendrocytes (which express O1 and O4) and finally into mature myelinating oligodendrocytes (which express O1, O4, myelin basic protein (MBP), and anti-proteolipid protein (PLP)). Thus, by monitoring the presence and absence of the NG2, O1, O4, MBP, and PLP markers it is possible to determine a given cell's developmental stage and to evaluate the role of Sema6A polypeptides in oligodendrocyte biology. Oligodendrocyte transcription factor-2 (Olig-2) is also known to be expressed in oligodendrocyte lineage and thus is used as a marker to detect oligodendrocytes. See Yokoo et al. *Amer. J. of Path.* 164: 1717-1725 (2004) (For a general review of oligodendrocyte biology, see, e.g., Baumann and Pham-Dinh, *Physiol. Rev.* 81: 871-927 (2001); Bras et al., *Int. J. Dev. Biol.* 49: 209-220 (2005).

Monoclonal antibodies against O4 and MBP were from Chemicon. Monoclonal antibody against PLP) (clone AA3, 1:10) was a gift from Pr. C. Luberzki. Yamamura et al., *J. Neurochem.* 57(5):1671-80 (1991). Monoclonal antibody against Astrocyte precursor cell (APC) was from VWR international (Fontenay Sous Bois, France). Antibody against CNPase was from Sigma. Antibody against NG2 (AB5320) was from Chemicon. Antibody against human Sema6A was from R&D Systems (Minneapolis, Minn.). Antibodies against $Na^{2+}$ and paranodine were from Sigma. Anti-myc antibody (9E10, 1:100) was from Santa Cruz Biotechnology (SC-40).

Sema6A mRNA is Expressed in Oligodendrocytes

The expression of Sema6A mRNA was analyzed by in situ hybridization in fresh frozen brain (sagittal sections) or spinal cord (coronal sections) of P1 and P15 mice. Swiss mice (Janvier, Le Genest Saint Isle, France) were anesthetized by inhalation of isofluorane foren (Abbott) and decapitated. Brains and optic nerves were frozen immediately in isopentane (−50° C.) and stored at −80° C. before hybridization. Tissue sections were postfixed for 10 min in 4% PFA, washed in PBS, pH 7.4, treated with proteinase K (10 µg/ml; Invitrogen, Carlsbad, Calif.) for 3-5 min, postfixed for 5 min in 4% PFA, washed in PBS, acetylated, and washed in PBS1% Triton X-100. Slides were incubated for 2 hr at room temperature in hybridization buffer (50% formamide, 5×SSC, 1×Denhardt's, 250 µg/ml yeast tRNA, and 500 µg/ml herring sperm, pH 7.4), and then tissue sections were hybridized overnight at 72° C. with digoxigenin-labeled Sema6A riboprobes (0.5 ng/µl). After hybridization, sections were rinsed for 2 hr in 2×SSC at 72° C. and blocked in 0.1 M Tris, pH 7.5, 0.15 M NaCl (B1) containing 10% normal goat serum (NGS) for 1 hr at room temperature. After blocking, slides were incubated overnight at room temperature with anti-digoxigenin antibody conjugated with the alkaline phosphatase (1:5000; Roche Diagnostics) in B1 containing 1% NGS. After additional washes, the alkaline phosphatase activity was detected using nitroblue tetrazolium chloride (NBT) (337.5 µg/ml) and 5-bromo-4-chloro-3-indolyl phosphate (BCIP) (175 µg/ml) (Roche Diagnostics). Sections were mounted in Mowiol (Calbiochem/Merck, Carlstadt, Germany). As shown in FIG. 3, Sema6A mRNA is widely expressed in the P15 mouse CNS white matter by oligodendrocytes during postnatal development.

Sema6A Protein is Expressed in Oligodendrocytes

The expression of Sema6A protein in oligodendrocytes on P15 mouse brain sections (from 4% PFA fixed brain) was confirmed by double immunostaining of Sema6A and PLP, Sema6A and APC (a marker for oligodendrocyte), and Sema6A and CNPase (a marker for oligodendrocyte and Schwann Cell). The sections were blocked for 1 hr at room temperature (RT) in PBS containing 0.2% gelatin (Prolabo, Fontenay-sous-Bois, France) and 0.25% Triton X-100 (PBS-G-T), and then incubated overnight at RT with primary antibodies, i.e., anti-mouse Sema6A antibody, anti-PLP antibody, anti-APC antibody, and anti-CNPase antibody. Cultures were then fixed with 4% PFA at room temperature for 10 min, rinsed, and then saturated and permeabilized in PBS buffer containing 10% NGS and 0.2% Triton-X100 for 30 min. Secondary antibodies, i.e., CY3-conjugated antibody for Sema6A and FITC-conjugated antibody for PLP, APC, and CNPase were diluted in PBS containing 10% NGS and 0.1% Triton X-100 for 1 h and, after washing, incubated for 1 h at RT with the secondary antibodies. After rinsing, cultures are mounted in Mowiol (Calbiochem/Merck, Carlstadt, Germany).

The double immunostaining showed that all Sema6A expressing cells also expressed APC, CNPase, or PLP in the white matter (data not shown.) However, some cells expressing PLP, APC, and CNPase do not express Sema6A. Thus Sema6A protein seems to be expressed in a subset of cells of the oligodendrocyte lineage or in oligodendrocytes at a specific precise stage of maturation. Therefore, co-immunolabelling obtained from Sema6A combined with oligodendrocyte markers, PLP, APC, or CNPase, confirmed the expression of Sema6A by oligodendrocytes cells in vivo.

On the same P15 brain sections (cerebellum, cortex), immunostaining with oligodendroglial specific proteins, e.g., PLP, was combined with Sema6A in situ hybridization. The standard in situ hybridization was performed as shown above except shortened proteinase K digestion (10 µg/ml) to 2 min. After in situ hybridization with a Sema6A riboprobe, sections were rinsed in PBS-T, blocked for 1 hr at RT in PBS-G-T and incubated overnight at RT with the anti-PLP antibody (clone AA3) and were then incubated in a biotinylated rabbit anti-rat antibody (1:200; Dako, Glostrup, Denmark) and an HRP-conjugated streptavidin (1:400; Amersham). The sections were developed with a diaminobenzidine reaction (brown precipitate). All cells expressing Sema6A transcript appeared in purple and were also surrounded by a brown precipitate indicating PLP expression (data not shown).

The Expression of Sema6A Protein is Developmentally Regulated.

The expression of Sema6A and APC on forebrain coronal sections from P15, P30 and P45 mice was also analyzed by double immunostaining, using anti-mouse Sema6A and anti-APC antibodies as described above. Strong APC expression was observed at all the different ages but the maximal co-labelling of APC/Sema6A cells was observed at P15, where 65% of the oligodendrocytes (APC+ cells) expressed Sema6A (data not shown). The proportion of APC-positive cells also expressing Sema6A in the white matter decreased to 14% at P30 and fell to 8% at P45 (data not shown). This showed that Sema6A expression is developmentally regulated, reaching a maximum at P15, during the peak of myelination.

Example 2

Sema6A Expression at Various Stages of Oligodendrocyte Differentiation

The expression of Sema6A was also shown in vitro in purified oligodendrocyte cultures. The cortex hemispheres of P0 to P5 mice were dissected and transferred to a culture medium consisting of DMEM supplemented with 10% calf serum. The tissue was dissociated by sieving through a 70 μm mesh nylon sieve in the culture medium. The cell suspension was dispensed in 100 mm diameter plastic tissue culture dishes coated with polyornithine. Oligodendrocyte precursor cells were detached selectively by gentle syringing the culture medium on the cell layer. Dislodged cells were then submitted to two successive preplating over a 12 hr period in non-coated plastic culture dishes to allow adhesion of remaining astrocytes and microglia. The non- and loosely adherent cells (oligodendrocytes) were subcultured in 60 mm plastic culture dishes. The cultures were stained either with anti-mouse Sema6A antibodies and anti-NG2 (a marker for oligodendrocyte progenitor cells) or anti-O4 (a marker of the oligodendrocyte lineage expressed from the pre-oligodendrocyte stage) and anti-MBP antibodies (a marker for mature oligodendrocytes). CY3 conjugated antibody were used as a secondary antibody to visualize Sema6A expression and FITC-conjugated ones for NG2, O4 and MBP. After 24 hours in vitro, different types of cells express NG2: some cells with a very undifferentiated morphology were only FITC-labelled (NG2+) and thus negative for Sema6A, others more differentiated ones (more processes) expressed NG2 and low level of Sema6A in the cell body but not in the cell processes (data not shown). After 48 hours in vitro O4-positive cells highly expressed Sema6A (data not shown). After 72 hours in vitro, MBP-positive cells highly expressed Sema6A (data not shown). This shows that Sema6A is more highly expressed in differentiated (O4 and MBP+) oligodendrocytes (as observed in vivo).

Example 3

Sema6A-Knockout Mice Exhibit a Decrease in Myelinated Axons

In order to generate Sema6A-knockout mice, a cassette encoding CD4 transmembrane domain-β-galactosidase-neomycin phosphotransferase (TM-β-geo) and human placental alkaline phosphatase (PLAP), separated by an internal ribosome entry site (IRES), was inserted in the 17$^{th}$ intron of Sema6A as described in Leighton et al., Nature, 410: 174-179. The remaining N-terminal portion of the Sema6A protein up to amino acid 623 (and thus lacking the transmembrane and cytoplasmic domains) was fused to β-galactosidase and trapped in the endoplasmic reticulum.

In order to analyze delay in myelination, the nodes of Ranvier in Sema6A-deficient mice have been studied. The nodes of Ranvier express several well identified proteins that have a characteristic expression and function at the node. Antibodies raised against the proteins involved in the formation of the node of Ranvier, such as paranodin, were used to detect the expression of the proteins. Nodes are well organized structures, closely interacting between the axon to be myelinated and the oligodendrocytes. Due to the characteristic expression of the proteins on the nodes, different regions can be visualized: $Na^{2+}$ voltage gated channels to visualize the central region of the node and paranodin to visualize two domains surrounding the central region of the node, which is called paranodin/$Na^{2+}$ channel cluster. The expression of $Na^{2+}$ channels and paranodin were visualized by immunohistochemistry in P16 mice optic nerves using anti-$Na^{2+}$ channels and paranodin antibodies (data not shown). The immunohistochemistry showed that a significant decrease in the number of paranodin/$Na^{2+}$ channel clusters (−40.54%; n=3) in Sema6A-deficient mice (data not shown). This result suggests that P16 Sema6A-deficient mice have less myelinated axons than the wild-type.

Sema6A-Knockout Mice Exhibit Reduced PLP Expression in Oligodendrocytes

Figure 4:
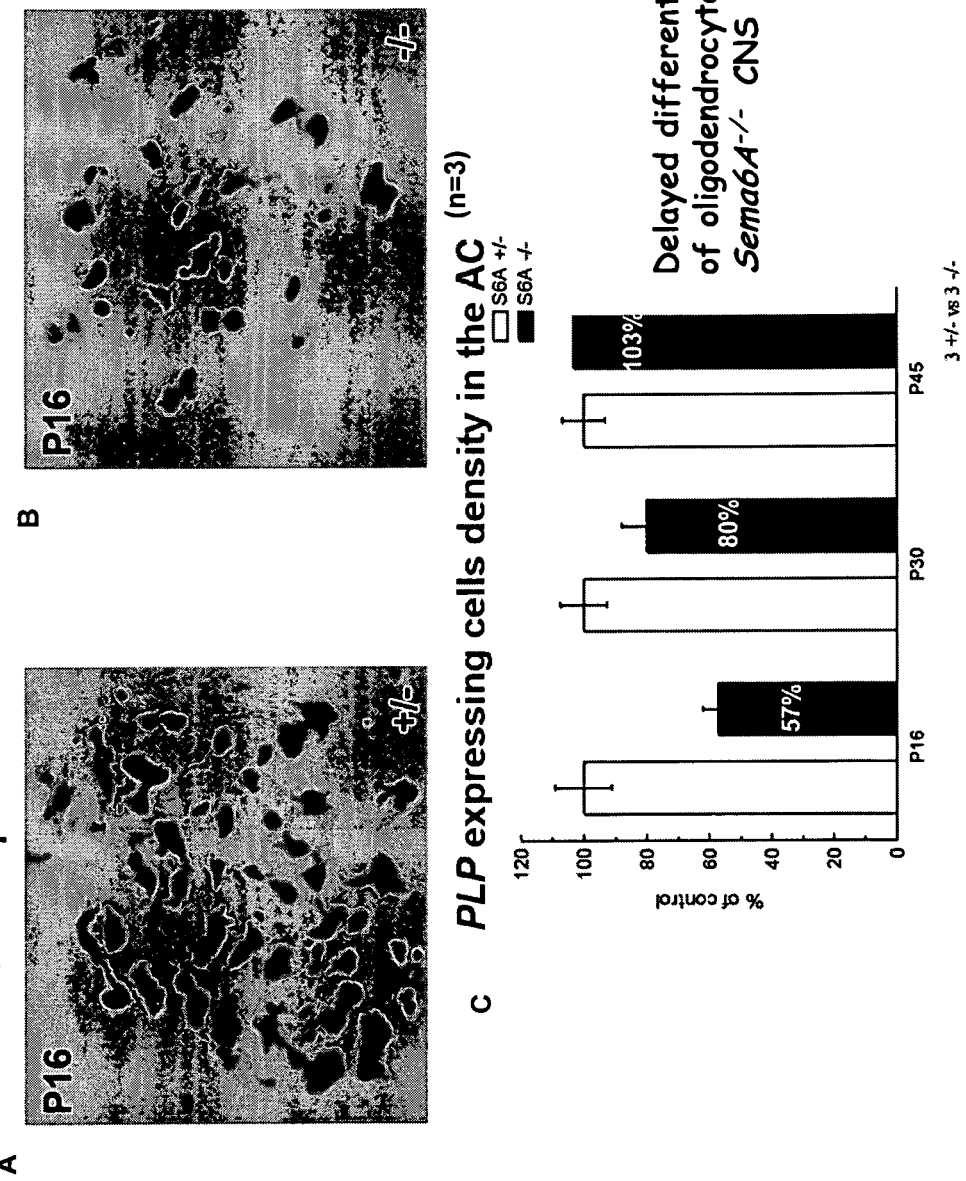

To determine if the differentiation or proliferation of oligodendrocytes was normal in Sema6A-deficient mice, three major axonal tracts, the anterior commissure (AC), the corpus callosum (CC) and the optic nerves (ON), were labeled by non radioactive in situ hybridization, and the number of PLP expressing cells were quantified. Three ages were analyzed for AC and CC, P16, P30 and P45 (3 animals for each) and P16 for the ON. No significant changes in the expression of PLP were observed in the CC at any ages (data not shown). However, the number of PLP expressing cells were decreased at P16 in the AC of Sema−/− mice (−43%) compared to wild-type littermate (FIG. 4). This reduction at P16 is explained by a major reduction of the number of PLP expressing cells (−60%), but also accompanied by a 30% reduction of the surface of the AC. The reduction is less pronounced in the AC at P30 (−20%) and goes back to normal in adults as shown in FIG. 4. Likewise, the expression of PLP in the P16 optic nerve also showed a similar reduction (−26%) (data not shown). However, no significant change was observed in the number of oligodendrocyte transcription factor 2 (Olig2) expressing cells, which belongs to the oligodendrocyte lineage, in the AC (data not shown). These results suggest a possible role for Sema6A in either the differentiation of oligodendrocytes in vivo or their ability to migrate and colonize axonal tracts.

Sema6A-Deficient Oligodendrocytes Exhibit Delayed Differentiation.

Oligodendrocytes were purified from Sema6A−/− newborn mice and analyzed for their ability to differentiate by the method described in Bernard et al., J. Neurosc. Res. 65: 439-445, 2001. Briefly, whole brain hemispheres of P0-P10 mouse or rat were dissected in phosphate buffered saline and transferred to culture medium composed of DMEM (Invitrogen 31966047) supplemented with penicillin (50 units/ml), streptomycin (50 μg/ml) (Invitrogen 15140), calf serum (10%) (Gibco 16030074), 5 ng/ml PDGFBB (Sigma P3201) and 5 ng/ml bFGF (Sigma F0291). The dissociation was performed by sieving the tissue through a 70 M mesh nylon (BD Biosciences) sieve in the culture medium. The cell suspension was dispensed in 100 mm diameter plastic tissue culture dishes coated with polyornithine (Sigma P3655). The cultures were incubated at 37° C. in a water saturated incubator equilibrated with 95% air-5% $CO_2$. Culture medium was changed 4 days after seeding and twice a week thereafter. After 8-10 days oligodendrocyte precursor cells were detached selectively by gentle syringing the culture medium on the cell layer. Dislodged cells were then submitted to two successive preplating over a 12 hr period in non coated plastic culture dishes to allow adhesion of remaining astrocytes and microglia. The non- and loosely adherent cells were subcultured in 60 mm plastic culture dishes coated with polyornithine in a chemically defined medium containing 0.5% fetal calf serum (FCS), 10 M insulin, 100 µg/ml transferrin, 0.5 µg/ml albumin, 2 µM progesterone, 100 µM putrescine, 40 ng/ml triiodothyronine, 40 ng/ml L-thyroxine, 40 nM d-biotin and 100 nM hydrocortisone. In the absence of additional mitogen, these subcultures give rise to an almost homogeneous cell population containing more than 90% Gal-C positive cells after 10 days. See Besnard et al., $Int.$ $J.$ $Dev.$ $Neurosci.$ 7(4): 401-409, 1989. To maintain these cells at the oligodendrocyte progenitor cell (OPC) stage and to prevent premature differentiation before processing, PDGFAA (10 ng/ml) (rats) or PDGFBB (10 ng/ml) and bFGF (10 ng/ml for rats and 20 ng/ml for mice) were added to the culture medium. After mitogen withdrawal, OPC differentiation occurs within 24-72 hrs. Bogler et al., $Proc.$ $Natl.$ $Acad.$ $Sci.$ $U.S.A.$ 87(16): 6368-6372, 1990; Durand et al. $EMBO$ $J.$ 16(2): 306-317, 1997. Sema6A-Fc protein purchased from R&D system was also added to the chemically defined medium.

Figure 5:
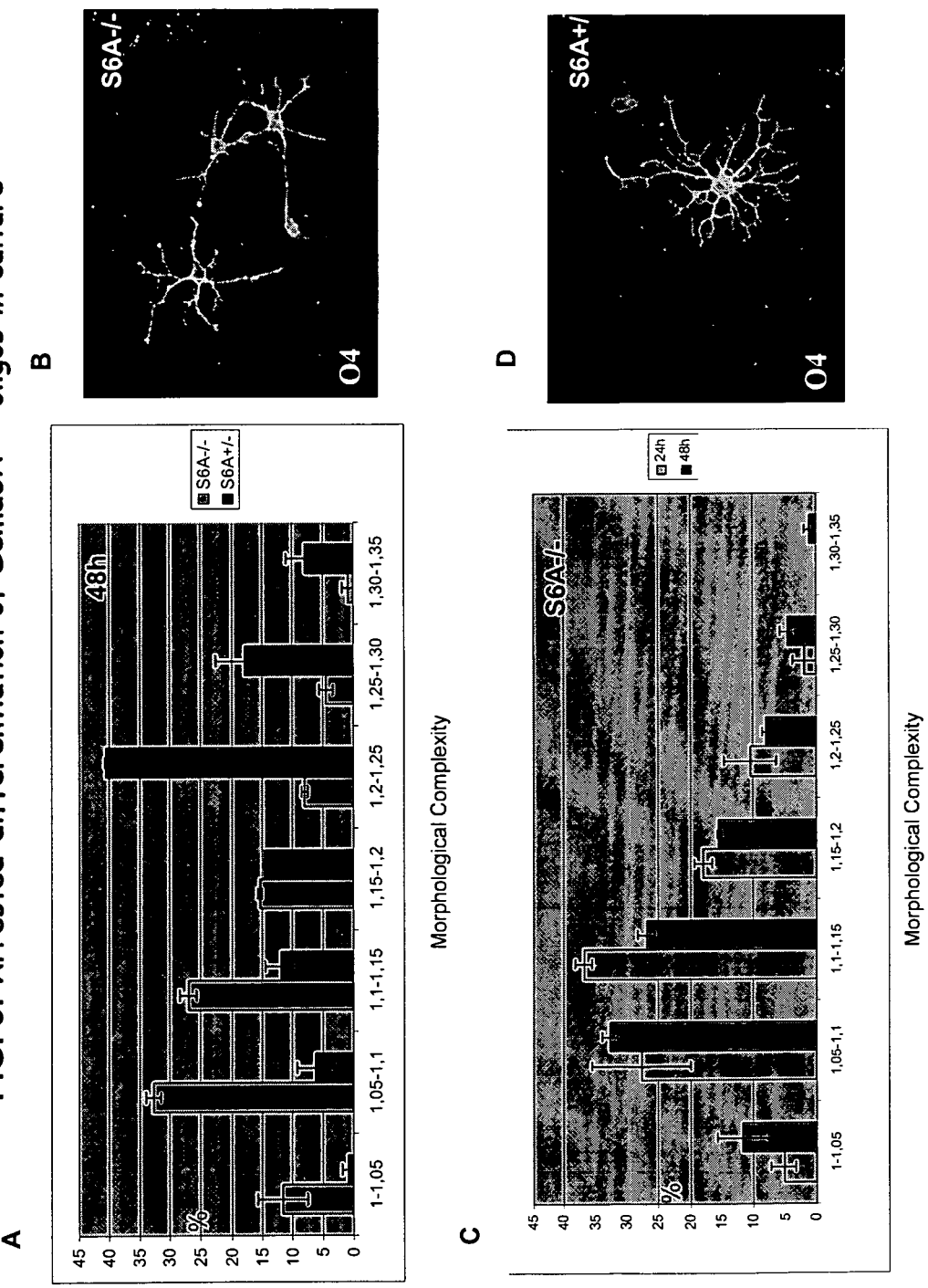

The maturation stage of oligodendrocyte can be measured by the morphological complexity of cultured oligodendrocytes, e.g., measuring the fractal dimension (FD) of the cell. Id. FIG. 5 shows the FD quantification of purified oligodendrocytes (visualized by phase contrast or labeled with anti-O4 antibody) from Sema6A+/- and Sema6A-/- mice, after 24 hr and 48 hr in vitro. This showed that while the majority of Sema6A+/- oligodendrocytes have a FD of 1.25 after 48 hr, most Sema6A-/- oligodendrocytes have an FD of only 1.05-1.15 (n=3) (FIG. 5A). The FD of Sema6A+/- and Sema6A-/- oligodendrocytes after 24 hr in vitro is similar to the FD of Sema6A-/- oligodendrocyte after 48 hr. (data not shown). These results demonstrate that oligodendrocyte differentiation is delayed in Sema6A-/- mice.

After 72 hr in culture, oligodendrocytes were immunostained with anti-O4 antibodies (a marker for differentiating oligodendrocytes) and anti-MBP antibody (a marker for differentiated oligodendrocytes) to measure the oligodendrocyte differentiation. As secondary antibodies, FITC-conjugated antibody for O4 and CY3-conjugated antibody for MBP were used. Under the microscope, randomly chosen fields were analyzed. After 72 hr, the number of O4+/MBP+ cells in Sema6A-/- were decreased 40.09% compared to that of wild-type (data not shown). The in vitro data supports the conclusion that oligodendrocyte differentiation is delayed in oligodendrocytes lacking Sema6A.

Example 4

Sema6A-Fc Promotes Myelination In Vitro

The role of Sema6A in myelination was examined in vitro by treating co-cultures of dorsal root ganglion (DRG) neurons and oligodendrocytes with Sema6A-Fc and testing for myelination by immunohistochemistry and western blot. For these studies, it was necessary to first generate primary cultures of DRG neurons and oligodendrocytes.

Sprague Dawley rats E14-E17 embryonic dorsal root ganglia were plated on coverslips coated with poly-L-lysine (100 µg/ml). They were grown for 2 weeks in Neurobasal medium (Invitrogen 21103049) supplemented with B27 (Invitrogen 17504). To remove proliferating glial cells, the cultures were pulsed twice with fluorodeoxyuridine (20 µM) for 1 week. Oligodendrocytes were prepared as described in Example 3.

For coculture studies, oligodendrocytes were added to DRG neuron drop cultures in the presence or absence of 100-300 ng/ml Sema6A-Fc (R&D systems, 1146-S6-025). The culture medium (Neurobasal medium supplemented with B27 and 100 ng/ml NGF) was changed, and fresh Sema6A-Fc was added to the cells every 3 days. To identify changes in myelination, 3-week-old cultures were labeled with anti-MBP antibody and were subjected to SDS-PAGE followed by western blot analysis.

Figure 6:
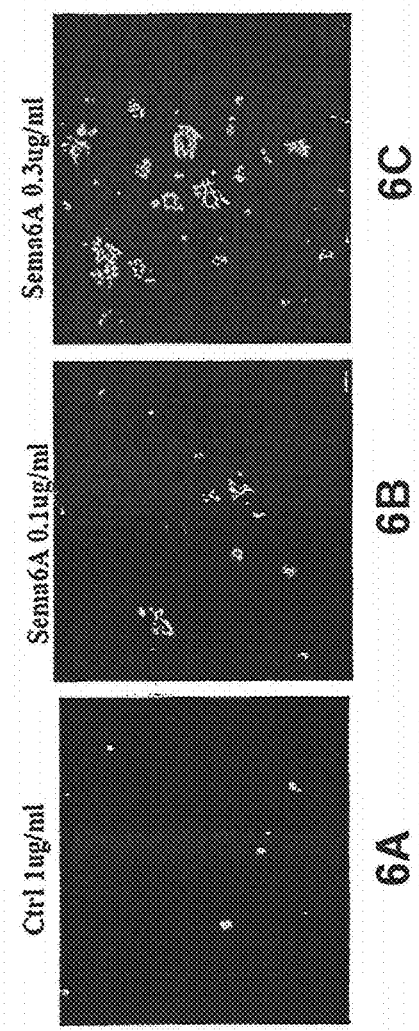

FIG. 6 shows that addition of Sema6A-Fc protein increased myelination in a dose dependent manner, from the negative control to 0.1 µg/ml and from 0.1 µg/ml to 0.3 µg/ml. Western blot also showed that MBP expression is increased by addition of Sema6A-Fc, i.e., 0.1 µg/ml to 0.3 µg/ml (data not shown). These data thus indicates that Sema6A polypeptides can promote or induce myelination.

Example 5

Sema6A-Fc Involved in Remyelination In Vivo

The exposure to cuprizone (a copper chelator) was used as an experimental model in which important demyelination can be reproducibly induced in large areas of the mouse brain. See Matsushima et al., $Brain$ $Pathol.$ 11 (1), 107-116, 2001. Eight week-old mice were fed with 0.2% cuprizone in their diet during 6 weeks, which causes mature oligodendrocytes to die by apoptosis. The cell death is closely followed by the recruitment of microglia and phagocytosis of myelin. At the termination of cuprizone treatment, or even after continued cuprizone exposure, oligodendrocyte precursor cells start to proliferate and invade demyelinated areas. If the cuprizone treatment is terminated, an almost complete remyelination takes place after a few weeks. Using the cuprizone model, Sema6A expression during demyelination and remyelination can be analyzed. After the cuprizone exposure and then termination, a significant increase of the number of Sema6A-expressing oligodendrocytes was observed in the corpus callosum of cuprizone-treated mice, starting 3 weeks after the administration of cuprizone, peaking at 4 weeks (+310%, n=3) and then returning to the basal level of expression at 6 weeks (FIG. 7). These Sema6A expressing cells in the lesion were all positive for olig-2. To characterize this upregulation of Sema6A-expression, BrdU was injected to cuprizone-treated animals one week prior to their sacrifice. Some of the Sema6A-expressing oligodendrocytes were BrdU positive, suggesting that they were recruited from progenitors that differentiated during the induction of demyelination by cuprizone.

Example 6

Sema6A May Play a Role in Experimental Allergic Encephalomyelitis (EAE)

To induce EAE, a 20-amino-acid peptide based on the mouse Myelin Oligodendrocyte Glycoprotein (MOG) sequence 35-55 was used. The day of initiation of EAE is referred as day 1 of the experiment, and starting from day 7, clinical assessment of EAE was performed daily, and mice were scored for the disease according to the following criteria: no disease (0); decreased tail tone (1); hind-limb weakness or partial paralysis (2); complete hind-limb paralysis (3); front- and hind-limb paralysis (4); and moribund state (5).

These scores reflect the evolution of the demyelinating disease. After the EAE inducement by the 20 amino acids peptide, Sema6A-/- mice developed less behavior defects than the control animals did. Mean scores of Sema6A-/- mice reached only a maximum of 0.5 while the mean scores of the control animals reached 3.5 (data not shown). Only 25% Sema6A-/- mice developed any signs of illness (data not shown). These experiments suggest that Sema6A may play a role in EAE induction and perhaps more widely auto-immune pathologies such as multiple sclerosis.

In addition, plexin A4-/- mice were tested for EAE induction. See Yamamoto et al., *Int. Immunol.* DOI: 10.1093/intimm/dxn006 (January 2008). While the Sema6A-/- mice showed EAE resistance as shown above, the plexin A4-/- mice showed increased sensitivity to the EAE induction. See id. Furthermore, an in vitro T cell proliferation assay was conducted in both Sema6A-/- and plexin A4-/- mice. See id. While plexin A4-/- mice showed significantly increased T cell proliferation, Sema6A-/- mice showed no difference in T cell proliferation. See id. This information suggests that the EAE resistance in Sema6A-/- mice may not be due to the abnormality of the immune response in the Sema6A-/- mice.

Example 7

Sema6A Polypeptide is Expressed in Human Multiple Scherosis Lesion Tissue

Figure 8A:
Figure 8B:
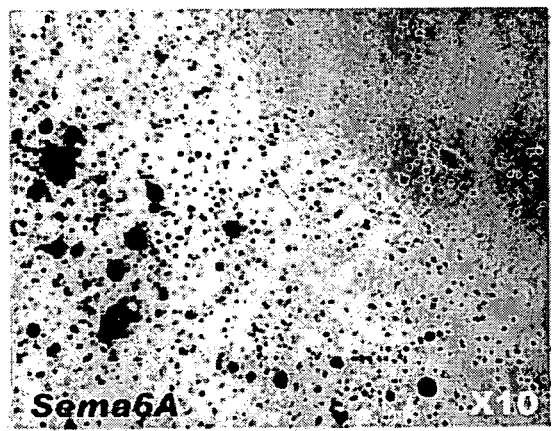

To determine whether Sema6A expression differs between human MS lesion tissues and non-lesion tissues, Sema6A expression was measured by a standard in situ hybridization and immunostaining in human MS tissues (neocortex samples). The MS tissues were obtained from the Federation de Neurologie at the Salpetriere Hospital, 75013 Paris. A standard in situ hybridization was performed. Tissues were fixed by immersion in 4% paraformaldehyde and embedded in paraffin. For in situ hybridization, tissue sections were first dewaxed in xylene (3×5 min) and then rehydrated by passing successively the slices through a decreasing gradient of ethanol (100%, 80%, 70%, 50%) and finally water and PBS. Tissue sections were postfixed for 10 min in 4% PFA, washed in PBS, pH 7.4, treated with proteinase K (50 µg/ml; Invitrogen, Carlsbad, Calif.) for 15 min at 37° C., postfixed for 5 min in 4% PFA, washed in PBS, acetylated, and dehydrated in successive bath of ethanol (50%, 70%, 80%, 100%). Slides were incubated for 2 hr at 68° C. in hybridization buffer and processes as shown in Example 1. Slides were incubated for 2 hr at room temperature in hybridization buffer (50% formamide, 5×SSC, 1×Denhardt's, 250 µg/ml yeast tRNA, and 500 µg/ml herring sperm, pH 7.4), and then tissue sections were hybridized overnight at 72° C. with digoxigenin-labeled Sema6A riboprobes (0.5 ng/µl). After hybridization, sections were rinsed for 2 hr in 2×SSC at 72° C. and blocked in 0.1 M Tris, pH 7.5, 0.15 M NaCl (B1) containing 10% normal goat serum (NGS) for 1 hr at room temperature. After blocking, slides were incubated overnight at room temperature with anti-digoxigenin antibody conjugated with the alkaline:phosphatase (1:5000; Roche Diagnostics) in B1 containing 1% NGS. After additional washes, the alkaline phosphatase activity was detected using nitroblue tetrazolium chloride (NBT) (337.5 µg/ml) and 5-bromo-4-chloro-3-indolyl phosphate (BCIP) (175 µg/ml) (Roche Diagnostics). As shown in FIGS. 8A and 8B, Sema6A mRNA is widely expressed in the human MS lesion tissue, but is not expressed in the non-lesion tissue.

Figure 8C:
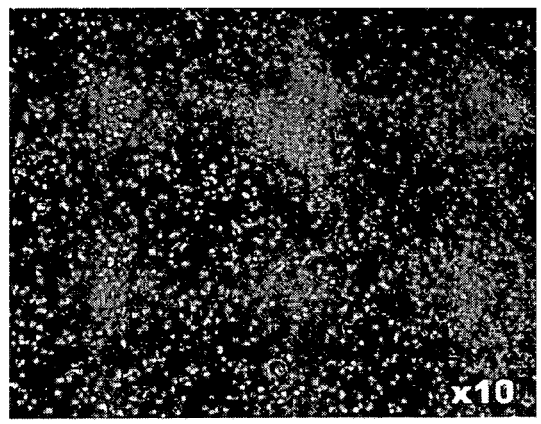

Immunostaining of the MS lesion tissue and non-lesion tissue was also conducted to show that the human MS lesion tissue highly expresses Sema6A. The tissue sections were blocked for 1 hr at room temperature (RT) in PBS containing 0.2% gelatin (Prolabo, Fontenay-sous-Bois, France) and 0.25% Triton X-100 (PBS-G-T), and then incubated overnight at RT with anti-human Sema6A antibody from R&D systems (Minneapolis, Minn.). Sections were then incubated for 1 hr at room temperature with CY3-conjugated antibody, (Jackson Immunoresearch] diluted in PBS-G-T. After rinsing in PBS-G-T (3×10 min), sections were mounted in Mowiol (Calbiochem/Merck, Carlstadt, Germany). As shown in FIG. 8C, the MS lesion tissue shows high level of Sema6A expression, where non-lesion tissue shows little or no Sema6A expression (FIGS. 8A and 8B).

In order to determine a possible use of Sema6A expression as a biomarker, the Sema6A expression was also measured in a tissue of non MS patients, and Sema6A was not expressed in non-MS patients (data not shown). It is well known that blood cells, e.g., dendritic cells, express Sema6A. See Gautier et al. *Immunopath. Infect. Dis.* 168(2): 453-465 (2006). The dendritic cells are also known to be present in cerebrospinal fluid (CSF). See Pashenkov et al. *Brain* 124(3): 480-492 (2001).

In view of the Sema6A expression on dendritic cells and differential Sema6A expression between MS lesion tissue and non lesion tissue, a specimen such as a tissue, e.g., skin tissue, or a body fluid, e.g., blood or CSF, is collected from a person to test for an MS disease state. The specimen is tested for expression of Sema6A by, e.g., ELISA. The presence in the fluid of a particular level may be indicative of possible MS, or the potential to develop MS. In additional embodiments, such an assay may be used to measure the effectiveness of a particular MS therapy. If the serum or CSF exhibits expression of Sema6A, the person from which the serum was drawn may be suspected of MS. Alternatively, dendritic cells from the collected specimen can be concentrated, and then the Sema6A in the specimen can be measured using, e.g., ELISA. According to this method, Sema6A detection can be used as a marker of actual or potential MS disease.

Example 8

Sema6A Polypeptide Interacts with Plexin-A2 Polypeptide

To determine the interaction between the Sema6A polypeptides and plexin-A2 polypeptides, a recombinant Fc-dimerized AP-tagged Sema6A ectodomain (extracellular domain) (AP-Sema6Aect-Fc) was added into mouse fibroblastic line cells (L cells) expressing full-length mouse plexin-A2 polypeptides as described in Suto et al., *J. Neurosci.* 25: 3628-3637 (2005). To make the recombinant Sema6A ectodomain, the sequence corresponding to the ectodomain of mouse Sema6A (Sema6Aect; amino acids 18-648) was amplified and inserted into the Aptag-4 vector (a gift from Dr. J. Flanagan, Harvard Medical School, Boston, Mass.) (AP-Sema6Aect). See Flanagan et al., *Methods Enzymol* 327: 17-35 (2000). To dimerize recombinant proteins, a fragment encoding AP-Sema6Aect was inserted into pEF-Fc (AP-Sema6Aect-Fc; AP-Sema6Bect-Fc; the pEF-Fc expression vector was a gift from Dr. S, Nagata, Osaka University). Human embryonic kidney 293T (HEK293T) cells were transfected with pEF-AP-Sema6Aect-Fc (the pCAGGS expression vector was a gift from Dr. J. Miyazaki, Osaka University) using Lipofectamine Plus (Invitrogen, Carlsbad, Calif.) and cultured in DMEM containing 10% fetal bovine serum (FBS) for 5-7 d in 5% $CO_2$ at 37° C. Culture supernatants were collected and filtered using 0.22 µm filters.

In order to generate plexin-A2 expressing L cells, the cDNA encoding the full-length mouse plexin-A2 protein was flanked with the signal sequence of mouse Sema3A, added the myc-tag (GGEQKLISEEDL: SEQ ID NO: 17) at the N-terminus, and then ligated into the expression vector pCAGGS. L cells were cotransfected with the plexin-A2-expression vector and pST-neoB (Katoh, et al., *Cell Struct. Funct.* 12: 575-580, 1987) according to the calcium phosphate method (Chen and Okayama, *Mol. Cell Biol.* 7: 2745-2752, 1987) and selected with GENETICIN (GIBCO). L cells were cultured with DH10 culture medium. Cell lines that stably expressed the plexin-A2 proteins were isolated by immunostaining with the anti-myc antibody 9E10. See Evan, et al., *Mol. Cell Biol.* 5: 3610-3616, 1985.

In order to show the binding of Sema6A to Plexin-A2, L-cells that stably express the full-length mouse plexin-A2 proteins were incubated with 250 µl of HBSS with 0.5 mg/ml BSA, 0.1% NaN$_3$, and 20 mM HEPES, pH 7.0 (HBHA solution) containing 1% FBS and the AP-Sema6Aect-Fc recombinant proteins (the culture supernatant) for 1 h on ice as described in Flanagan and Leder, *Cell* 63: 185-194 (1990). After removal of the HBHA solution, cells were treated with 250 µl of 10 mM Tris-HCl, pH 8.0, supplemented with 0.1% Triton X-100 to dissolve the recombinant proteins bound to the cell surface. The cell lysates were subjected to colorimetric analysis to measure AP activity as described in Flanagan and Leder, *Cell* 63: 185-194 (1990) and Flanagan et al., *Methods Enzymol* 327: 17-35 (2000).

It was shown that the Fc-dimerized recombinant AP-tagged ectodomain of Sema6A bound with a high affinity to plexin-A2 expressing L cells. The dissociation constant (Kd) value for the interaction of Sema6A with plexin-A2 was 3.21 nM (data not shown). The Kd value was comparable to the Kd value for the interaction of Sema6A with plexin-A4, i.e., 3.56 nM) described in Suto et al., *J. Neurosci.* 25: 3628-3637 (2005).

Example 9

A Single Mutation in Plexin-A2 can Ablate the Binding of Sema6A

In order to determine the binding site of plexin-A2/plexin-A4 to Sema6A, C57BL6/J mutant mice, i.e., NMF454, were examined. NMF454 mice (A gift of Dr S. Ackerman, Jackson Labs, Bar Harbor, USA) were identified in a recessive, genome-wide N-ethyl N-nitrosourea (ENU) mutagenesis screen of C57BL6/J mice. Histological analysis of NML454 mutant mice revealed a hypercellular molecular layer of the cerebellum which appeared strikingly similar to that of plexin-A2 and Sema6A null mice Renaud et al. *Nature Neuroscience,* in press (2008).

To determine whether the NMF454 mutation occurred in either the plexin-A2 or Sema6A gene, a gene mapping using microsatellite markers was conducted. F2 offspring (n=11), which showed the NMF454 phenotype were generated by an intercross of F1 progenies from a mapping cross (C57BL6/J X BALB/cBy), and the affected F2 offspring were identified histologically. The F2 offspring were then genotyped with the polymorphic microsatellite markers, D1Mit155 and D18Mit178, which are closely linked to the plexin-A2 and Sema6A genes, respectively. No linkage was found with D18Mit178 ($X^2$=1.2; P>0.5). However, tight linkage was observed with D1Mit155 ($X^2$=33.0; P<0.0001). This result, combined with the phenotypic analysis, suggested that the NMF454 mutation resided in the plexin-A2 gene (Plxna2).

To determine the exact location of the mutation, western blot analysis of plexin-A2 expression in the cerebellum and neocortex was conducted. The western blot analysis revealed that a band around 250 kDa was present in NMF454 homozygous mutants mice (n=2), wild type and NMF454 heterozygous controls (n=2) but not in the regular plexin-A2 knockout line as shown in FIG. 9A. This data suggests that the ENU mutation did not result in a null allele or a truncated plexin-A2 protein. To further localize the mutation, all exons of the plexin-A2 gene (Plxna2) were fully sequenced from genomic DNA of NMF454 homozygous mutants (n=3) and wild type controls (n=2). This revealed a single nucleotide substitution of the cytosine at position 1187 by an adenine resulting in the replacement of the alanine (396) by a glutamic acid residue. Furthermore, an alignment of vertebrate plexin-A sequences revealed that this alanine, localized in the semaphorin domain, is evolutionarily conserved in both Sema6A receptors, i.e., plexin-A2 and plexin-A4 proteins (FIG. 9B). However, the alignment showed that the alanine (396) was absent in plexin-A1 and plexin-A3, which are not known to bind Sema6A (FIG. 9B). See Suto et al. *J. Neurosci.* 25: 3628 (2005); See also Suto et al. *Neuron* 53: 535 (2007).

To determine whether the alanine (396) mutation in NMF454 homozygous mutants perturbs the plexin-A2 binding to Sema6A, a targeted mutagenesis was conducted to introduce into the plexin-A2 cDNA the same point mutation of the cytosine 1187 (GCG to GAG) using QuikChange II XL Site-Directed Mutagenesis Kit (Stratagene). The primers used for the mutagenesis were as follows:

```
Forward Primer
                                        (SEQ ID NO: 18)
5'-GCAGTGCACCAAGGAGCCTGTCCCAATCG-3'

Reverse Primer
                                        (SEQ ID NO: 19)
5'-CGATTGGGACAGGCTCCTTGGTGCACTGC-3'
```

The mutated construct (plexin-A2A396E) was fully sequenced, confirming that only the cytosine 1187 was replaced by adenine.

This plexin-A2A396E cDNA was then expressed in COS7 cells, and its ability to bind Sema6A-AP was tested using the same method shown in Example 8. See Suto et al. *Neuron* 53: 5354 (2007). The results of the binding assay showed that Sema6A-AP bound very strongly to COS7 cells expressing wild-type plexin-A2 (FIG. 9C). However, Sema6A-AP did not bind at all to cells expressing plexin-A2A396E (FIG. 9D) although both wildtype and mutant proteins appeared to be expressed at similar levels.

What is claimed is:

1. A method for promoting proliferation, differentiation, or survival of oligodendrocytes to a mammal in need thereof, comprising administering to the mammal an effective amount of a composition comprising an isolated mammalian semaphorin 6A ("Sema6A") polypeptide, which comprises amino acids 56 to 472 of SEQ ID NO: 2, wherein the administering is via intraocular, intrathecal, subdural, intracerebroventricular, intracranial or intralesional administration or is an administration directly into the central nervous system and wherein the administering promotes proliferation, differentiation, or survival of oligodendrocytes to the mammal.

2. A method for promoting oligodendrocyte-mediated myelination of neurons to a mammal in need thereof, comprising administering to the mammal an effective amount of a composition comprising an isolated mammalian Sema6A polypeptide, which comprises amino acids 56 to 472 of SEQ ID NO: 2, wherein the administering is via intraocular, intrathecal, subdural, intracerebroventricular, intracranial or intralesional administration or is an administration directly into the central nervous system and wherein the administering promotes oligodendrocyte-mediated myelination of neurons to the mammal.

3. The method of claim 1 or 2, wherein the administering treats a disease, disorder, or injury associated with dysmyelination or demyelination or destruction of myelin in said mammal.

4. The method of claim 1 or 2, wherein the administering treats a disease, disorder, or injury associated with oligodendrocyte death or lack of differentiation in said mammal.

5. The method of claim 1 or 2, wherein said Sema6A polypeptide binds to a plexin-A2 polypeptide.

6. The method of claim 5, wherein said Sema6A polypeptide is attached to a non-Sema6A moiety.

7. The method of claim 3, wherein said disease, disorder, or injury is selected from the group consisting of multiple sclerosis (MS), progressive multifocal leukoencephalopathy (PML), encephalomyelitis (EPL), central pontine myelolysis (CPM), adrenoleukodystrophy, Alexander's disease, Pelizaeus Merzbacher disease (PMZ), Wallerian Degeneration, optic neuritis, transverse myelitis, amylotrophic lateral sclerosis (ALS), Huntington's disease, Alzheimer's disease, Parkinson's disease, spinal cord injury, traumatic brain injury, post radiation injury, neurologic complications of chemotherapy, stroke, acute ischemic optic neuropathy, vitamin E deficiency, isolated vitamin E deficiency syndrome, Bassen-Kornzweig syndrome, Marchiafava-Bignami syndrome, metachromatic leukodystrophy, trigeminal neuralgia, and Bell's palsy.

8. The method of claim 3, wherein said disease, disorder, or injury is multiple sclerosis (MS).

9. The method of claim 6, wherein the non-Sema6A moiety is a heterologous polypeptide selected from c-myc, human placental alkaline phosphatase, an immunoglobulin hinge and Fc region and a combination of two or more of the heterologous polypeptides.

10. The method of claim 9, wherein the non-Sema6A moiety is a polymer.

11. The method of claim 1 or 2, wherein the composition is administered directly into the central nervous system.

12. The method of claim 1 or 2, wherein the isolated Sema6A polypeptide comprises, consists essentially of, or consists of an extracellular domain.

13. An in vitro method for promoting proliferation, differentiation, or survival of oligodendrocytes or oligodendrocyte-mediated myelination of neurons, comprising contacting the oligodendrocytes or a mixture of neurons and oligodendrocytes with an effective amount of a composition comprising an isolated Sema6A polypeptide, which comprises amino acids 56 to 472 of SEQ ID NO: 2.

14. The method of claim 13, wherein the Sema6A polypeptide binds to a plexin-A2 polypeptide.

* * * * *